(12) United States Patent
Kurosawa et al.

(10) Patent No.: US 8,580,097 B2
(45) Date of Patent: Nov. 12, 2013

(54) ISOTACHOPHORESIS OF BLOOD-DERIVED SAMPLES

(75) Inventors: Tatsuo Kurosawa, Amagasaki (JP);
Mitsuo Watanabe, Amagasaki (JP);
Takuma Ohtsubo, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 706 days.

(21) Appl. No.: 12/709,423

(22) Filed: Feb. 19, 2010

(65) Prior Publication Data

US 2010/0270157 A1  Oct. 28, 2010

(30) Foreign Application Priority Data

Apr. 27, 2009  (JP) ................ 2009-108355

(51) Int. Cl.
*G01N 27/447*  (2006.01)
*G01N 27/26*  (2006.01)

(52) U.S. Cl.
USPC .......................... 204/549; 435/6.1; 204/645

(58) Field of Classification Search
USPC ............... 204/450–452, 549, 645; 435/6.1
See application file for complete search history.

(56) References Cited

U.S. PATENT DOCUMENTS

2009/0152114 A1* 6/2009 Kawabata et al. ............ 204/451

FOREIGN PATENT DOCUMENTS

| JP | A-2000-516343 | 12/2000 |
| JP | A-2003-202322 | 7/2003 |
| JP | A-2004-325191 | 11/2004 |
| JP | A-2005-031070 | 2/2005 |
| JP | A-2006-317357 | 11/2006 |
| JP | A-2007-518977 | 7/2007 |
| JP | A-2010-512371 | 4/2010 |
| WO | WO-02/082083 A1 | 10/2002 |
| WO | WO 2007/027495 * | 3/2007 |
| WO | WO-2007/027495 A1 | 3/2007 |
| WO | WO-2007/121263 A2 | 10/2007 |

OTHER PUBLICATIONS

Kawabata et al. (Electrophoresis, 2008, 29, 1399-1406).*
Park et al. (Anal. Chem. 2008. 80, 808-814).*
Kagebayashi et al. (Analytical Biochemistry, 288, 2009, 306-311).*
Wang et al. (Electrophoresis, 2009, 30, 3250-3256).*
Oefner et al. (Electrophoresis 1985, 6, 538-544).*
Hruška et al., "Simul 5—Free dynamic simulator of electrophoresis," *Electrophoresis*, 27: 984-991 (2006).

* cited by examiner

*Primary Examiner* — J. Christopher Ball
*Assistant Examiner* — Jennifer Dieterle
(74) *Attorney, Agent, or Firm* — Finnegan, Henderson, Farabow, Garrett & Dunner, LLP

(57) ABSTRACT

Methods are provided for forming a complex comprising an analyte (or an analyte analogue) from a blood-derived sample and labeling substances, and separating the complex from excess labeling substances and coexisting substances from the blood-derived sample, in a rapid, simple, convenient, and highly precise isotachophoresis (ITP) process by adding 2-(N-morpholino)ethane sulfonate (MES) salt and/or glutamate salt to the ITP sample. Methods are also provided for measuring the analyte in blood-derived samples with high precision and high sensitivity, based on the amount of the complex separated or the amount of uncomplexed labeling substance-containing molecules.

28 Claims, 13 Drawing Sheets

Fig. 1
Purified terminal aminated DNA
├─ Sulfo-SMPB linker reaction
├─ Removal of un-reacted Linker by gel filtration
├─ Reaction with an anti-AFP antibody Fab' fragment
├─ Purification of DNA-antibody by a DEAE column
DNA-antibody
Fig. 2
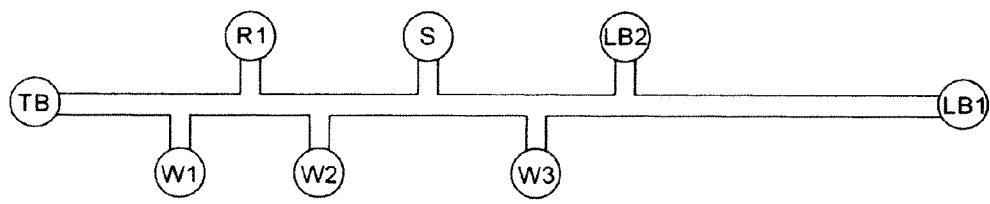
Fig. 3
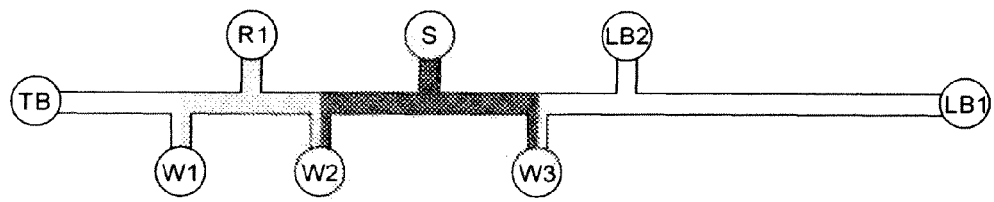

ISOTACHOPHORESIS OF BLOOD-DERIVED SAMPLES

RELATED APPLICATION

This application claims priority from Japanese Patent Application No. 2009-108355, filed Apr. 27, 2009, which is incorporated herein by reference in its entirety for all purposes.

TECHNICAL FIELD

The present invention relates to an isotachophoresis, in particular, a method for separating the following complex and coexisting materials in a blood-derived sample, while concentrating a complex containing an analyte in the blood-derived sample or an analogue thereof, a substance capable of forming complex with said analyte or the analogue thereof, a substance capable of changing electrophoretic mobility of said analyte or the analogue thereof, and a detectable labeling substance, by isotachophoresis; and a method for measuring the analyte in the sample, based on amount of the complex separated.

BACKGROUND ART

Electrophorestic separation using a capillary or a microfluidics chip has been used widely as an analysis method capable of analyzing a small amount of a sample in a short time and in high precision. However, there is a problem of insufficient sensitivity caused by small amount of the sample which can be injected at the inside of the capillary.

To resolve this problem, there has been proposed a method for preliminary separating and concentrating (an on-line pre-concentration method) a sample by isotachophoresis (ITP) etc., and then for providing thus separated and concentrated sample to capillary electrophoresis (CZE) or capillary gel electrophoresis (CGE) (Patent Literature 1, Patent Literature 2 etc.).

ITP is based on principle that, by applying a voltage in a state that a sample including the analyte is sandwiched between an electrophoresis medium (a leading buffer: LB) including a leading ion having faster (larger) electrophoretic mobility than that of the analyte in the sample, and an electrophoresis medium including a trailing ion having slower (smaller) electrophoretic speed than that of the analyte in the sample (a trailing buffer: TB), the analyte is concentrated, while the analyte can be separated from other components in the sample.

On the other hand, there has been proposed a method for enhancing separation efficiency between the analyte and other components, by using a spacer ion having intermediate electrophoretic mobility between electrophoretic mobility of the analyte and electrophoretic mobility of other components to be separated, in ITP, and thus by distributing the analyte and components to be separated, before and after said spacer ion; and various spacer ions to be used (Patent Literature 3, Non-Patent Literature 1 etc.).

PRIOR ARTS

Patent Literature
[Patent Literature 1] JP-A-2004-325191
[Patent Literature 2] JP-A-2006-317357
[Patent Literature 3] JP-A-2007-518977

Non-Patent Literature
[Non-Patent Literature 1] Electrophoresis 2006, 27, 984-991.

SUMMARY OF INVENTION

Problem to be Solved by the Invention

However, it has been found that, in the case of separating the following complex and the coexisting materials in the blood-derived sample, while concentrating the complex containing the analyte in said blood-derived sample or the analogue thereof, the substance capable of forming complex with said analyte or the analogue thereof (Complex Forming Substance; hereafter abbreviated as CFS), the substance capable of changing electrophoretic mobility of said analyte or the analogue thereof (hereafter abbreviated as the mobility-changing substance), and the detectable labeling substance, using the blood-derived sample as the sample, by ITP, there is the case where said complex and the coexisting materials in the blood-derived sample cannot be separated sufficiently.

Therefore, the present invention relates to a method of separating said complex and the coexisting materials in the blood-derived sample rapidly, simply and conveniently and in high precision, while concentrating the complex containing the analyte in the blood-derived sample or the analogue thereof, the CFS, the mobility-changing substance, and the detectable labeling substance, by ITP; and a method for measuring the analyte in the sample, based on amount of the complex separated or amount of the free labeling substance-containing molecule not involved in formation of said complex.

Means for Solving the Problem

The present invention is composed of the following constitutions:

1.

(A) A method for separating complex, which comprises,
concentrating the following complex A, the following complex A' or the following complex A", while carrying out any separation of the following [A-1] to [A-3] by isotachophoresis (ITP), in the presence of an 2-(N-morpholino)ethane sulfonate (MES) ion and/or a glutamate ion:

[A-1] separation of (i) the complex A comprising (a) an analyte in a blood-derived sample, (b) one or more kinds of substances (CFS) capable of forming the complex with said analyte bound with a substance (a mobility-changing substance) capable of changing an electrophoretic mobility of the analyte (a mobility-changing CFS) and (c) one or more kinds of CFSs bound with a labeling substance (labeled CFSs) from (ii) the free labeled CFS not involved in formation of said complex A, and (iii) coexisting substances in the blood-derived sample;

[A-2] separation of (i) the complex A' comprising (a') an analogue (a labeled analogue) of the analyte bound with the labeling substance and (b) one or more kinds of the mobility-changing CFSs from (ii) the free labeled analogue not involved in formation of said complex A', and (iii) the coexisting substances in the blood-derived sample;

[A-3] separation of (i) the complex A" comprising (a") the analogue (the mobility-changing analogue) of the analyte bound with the mobility-changing substance and (c) one or more kinds of the labeled CFSs from (ii) the free labeled CFS not involved in formation of said complex A" and/or the complex B" comprising the analyte and the labeled CFSs, and (iii) the coexisting substances in the blood-derived sample.

2.

The method for separating the complex according to the above mentioned 1, the method further comprising (B) further separating any one of the following [B-1] to [B-3], which were separated as a result of the step (A), by capillary zone electrophoresis (CZE) or capillary gel electrophoresis (CGE), in the presence of the MES ion and/or the glutamate ion:

[B-1] (i) said complex A and (iii) the coexisting substances in the blood-derived sample;

[B-2] (i) said complex A' and (iii) the coexisting substances in the blood-derived sample;

[B-3] (i) said complex A" and (iii) the coexisting substances in the blood-derived sample.

3.

A method for measuring an analyte, which comprises, measuring [C-1] amounts of said complex A or amounts of the free labeled CFS not involved in forming of said complex A, [C-2] amounts of said complex A' or amounts of the free labeled analogue not involved in forming of said complex A', or [C-3] amounts of said complex A" or amounts of the free labeled CFS not involved in forming of said complex A" and/or amounts of the complex B" containing the analyte and the labeled CFS, which were separated by the method according to claim 1, and determining amounts of the analyte on the basis of the measured amount; or measuring amounts of said complex A, amounts of said complex A', or amounts of said complex A", which were separated by the method according to claim 14, and determining amounts of the analyte on the basis of the measured amount.

That is, the present inventors have found that, in the case of separating the following complex and the coexisting materials in the blood-derived sample, while concentrating the complex containing the analyte in said blood-derived sample or the analogue thereof, the CFS, the mobility-changing substance, and the detectable labeling substance, using the blood-derived sample as the sample, by ITP, only the MES ion and/or the glutamate ion, among various ions conventionally known as a spacer ion in ITP, are capable of separating said complex and the coexisting materials in the blood-derived sample (in other words, in such a case, only the MES ion and/or the glutamate ion can be the spacer ion between said complex and the coexisting materials in the blood-derived sample), and have thus completed the present invention.

Effects of the Invention

According to the method of the present invention, it is possible to separate the following complex (Namely, the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analogue and one or more kinds of the labeled CFSs) and the coexisting materials in the blood-derived sample rapidly, simply and conveniently, and in high precision, while concentrating the complex containing the analyte in said blood-derived sample or the analogue thereof, the CFS, the mobility-changing substance, and the detectable labeling substance, by using ITP. As a result, the analyte in the sample can be measured in high precision, based on amount etc. of the complex separated. Further, by providing said complex separated and concentrated by ITP to CZE or CGE, the analyte in the blood-derived sample can be measured in high precision and in high sensitivity.

BRIEF DESCRIPTION OF THE DRAWINGS

FIG. 1 shows a preparation scheme of a DNA labeled antibody [an anti-AFP antibody WA1Fab' fragment bound with a 250 by DNA fragment (the mobility-changing CFS)], prepared in Example 1.

FIG. 2 shows a layout of the capillary chip prepared in Example 1.

FIG. 3 shows arrangement relation between an electrophoresis sample and reagent solution introduced at the inside of the capillary, in Example 1.

MODE FOR CARRYING OUT THE INVENTION

1. Isotachophoresis (ITP)

Figure 4:
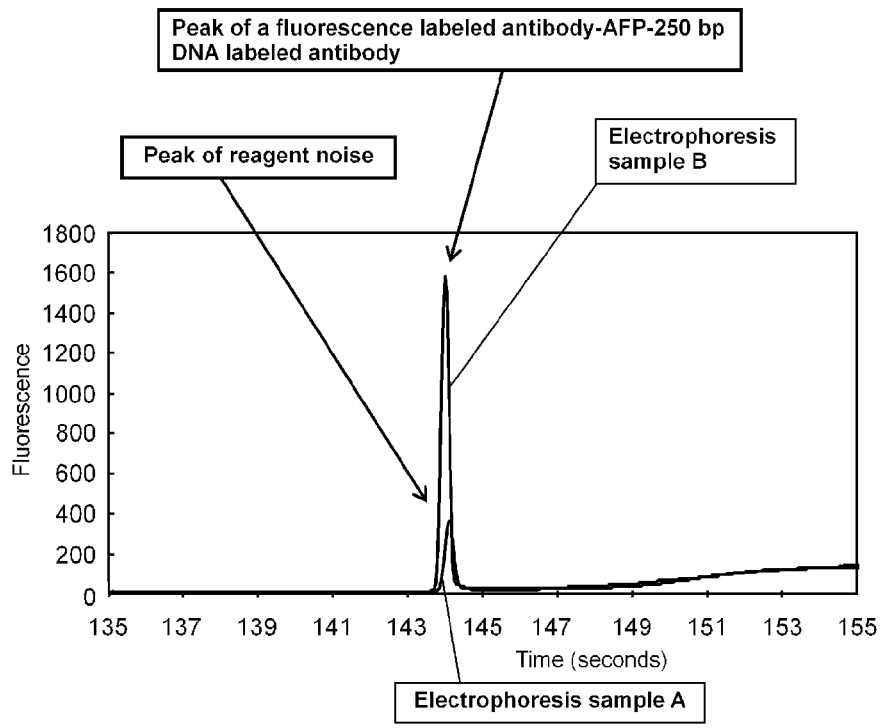
FIG. 4 shows an electropherogram in the case of using an electrophoresis sample A (a serum free sample) [Experiment No. 1-1] (ITP), and in the case of using an electrophoresis sample B (a sample added with AFP) [Experiment No. 1-2] (ITP), obtained in Example 1.

ITP is based on phenomenon that, by applying a voltage in a state that a sample including an analysis objective substance is sandwiched between an electrophoresis medium (a leading buffer; hereafter abbreviated as LB) including an ion (a leading ion) having faster (larger) electrophoretic mobility than that of the analysis objective substance (ion) in the sample, and an electrophoresis medium (a trailing buffer; hereafter abbreviated as TB) including an ion (a trailing ion) having slower (smaller) electrophoretic mobility than that of the analysis objective substance in the sample, in the capillary, the analysis objective substance (ion) and other components (ions) are separated in each different zone, and also, in the case where concentration of the analysis objective substance (ion) is lower than concentration of the leading ion, the analysis objective substance (ion) is concentrated, and after reaching a steady state, all of the components (ions) show isotachophoresis.

The present invention can be applied to a method for separating the following complex and the coexisting materials in the blood-derived sample, while concentrating the complex containing the analyte in said blood-derived sample or the analogue thereof, the CFS, the mobility-changing substance, and the detectable labeling substance (Namely, the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analogue and one or more kinds of the labeled CFSs) (hereafter may be abbreviated as the complex relevant to the present invention), by ITP,; in particular, as will be described later, can be applied to a method for preliminarily separating and concentrating (an online pre-concentration method) a sample (Namely, the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analogue and one or more kinds of the labeled CFSs) to provide to CZE or CGE etc, by ITP.

ITP in the present invention includes the following methods:

(A): A Non-Competitive Method:

A method for separating (i) the following complex A from (ii) the free labeled CFS not involved in formation of said complex A and (iii) the coexisting materials in the blood-derived sample, while concentrating said complex A including the analyte in the blood-derived sample, one or more kinds of the mobility-changing CFSs and one or more kinds of the labeled CFSs, which made existed between the LB zone and the TB zone at the inside of the capillary for carrying out ITP, at the downstream side of the TB zone, by ITP, by applying a voltage at the both sides of the capillary.

(B): A Competitive Method:

A method for separating (i') the following complex A' from (ii') the free labeled analogue not involved in formation of said complex A' and (iii') the coexisting materials in the blood-derived sample, while concentrating said complex A'including the labeled analogue bound with the detectable labeling substance and one or more kinds of the mobility-changing CFSs, which made existed between the LB zone and the TB zone at the inside of the capillary for carrying out ITP, at the downstream side of the TB zone, by ITP, by applying a voltage at the both sides of the capillary, or a method for separating (i") the following complex A"from (ii") the free labeled CFS not involved in formation of said complex A" and/or the complex B" including the analyte and the labeled CFS, and (iii") the coexisting materials in the blood-derived sample, while concentrating said complex A"including the mobility-changing analogue and one or more kinds of the labeled CFSs, which made existed between the LB zone and the TB zone at the inside of the capillary for carrying out ITP, at the downstream side of the TB zone, by ITP, by applying a voltage at the both sides of the capillary.

2. The Separation Method of the Present Invention

The present invention is characterized by carrying out the above ITP, in the presence of the MES ion and/or the glutamate ion, in other words, by applying the blood-derived sample to ITP, in the presence of the MES ion and/or the glutamate ion.

By carrying out ITP, in the presence of the MES ion and/or the glutamate ion, the complex (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analogue and one or more kinds of the labeled CFSs) relevant to the present invention and the coexisting materials in the blood-derived sample can be separated more efficiently.

That is, in the absence of the MES ion and/or the glutamate ion, because the complex relevant to the present invention and the coexisting materials in the blood-derived sample have nearly the same degree of electrophoretic mobility, they are not separated sufficiently. However, because the MES ion and/or the glutamate ion have intermediate electrophoretic mobility between those of the complex relevant to the present invention and the coexisting materials in the blood-derived sample, in the presence of the MES ion and/or the glutamate ion, as a result thereof, a zone (plug) of the MES ion or the glutamate ion is inserted between a zone (plug) of the complex relevant to the present invention, and a zone (plug) of the coexisting materials in the blood-derived sample, by which said complex and said coexisting materials can be separated sufficiently.

As described above, various ions including the MES ion and the glutamate ion have been known as a spacer ion in ITP.

However, in the case of separating the following complex and the coexisting materials in the blood-derived sample, while concentrating the complex containing the analyte in said blood-derived sample or the analogue thereof, the CFS, the mobility-changing substance, and the detectable labeling substance, using the blood-derived sample as the sample, by ITP, only the MES ion and/or the glutamate ion, among various ions conventionally known as a spacer ion in ITP, are capable of separating said complex and the coexisting materials in the blood-derived sample (in other words, in such a case, only the MES ion and/or the glutamate ion can be the spacer ion between said complex and the coexisting materials in the blood-derived sample).

This fact has not been known at all up to now, and the present inventors found out for the first time.

That is, the separation method of the present invention is characterized by concentrating the following complex A, the following complex A' or the following complex A", while (A) carrying out any separation of the following [A-1] to [A-3] by isotachophoresis (ITP), in the presence of an MES ion and/or a glutamate ion:

[A-1] separation of (i) the complex A comprising (a) an analyte in a blood-derived sample, (b) one or more kinds of substances (CFS) capable of forming the complex with said analyte bound with a substance (a mobility-changing substance) capable of changing an electrophoretic mobility of the analyte (a mobility-changing CFS) and (c) one or more kinds of CFSs bound with a labeling substance (labeled CFSs) from (ii) the free labeled CFS not involved in formation of said complex A, and (iii) coexisting substances in the blood-derived sample.

[A-2] separation of (i) the complex A' comprising (a') an analogue (a labeled analogue) of the analyte bound with the labeling substance and (b) one or more kinds of the mobility-changing CFSs from (ii) the free labeled analogue not involved in formation of said complex A', and (iii) the coexisting substances in the blood-derived sample.

[A-3] separation of (i) the complex A" comprising (a") the analogue (the mobility-changing analogue) of the analyte bound with the mobility-changing substance and (c) one or more kinds of the labeled CFSs from (ii) the free labeled CFS not involved in formation of said complex A" and/or the complex B" comprising the analyte and the labeled CFSs, and (iii) the coexisting substances in the blood-derived sample.

As described above, the separation method of the present invention relates to a method for concentrating the complex relevant to the present invention, while separating the complex relevant to the present invention from the free labeling substance-containing molecules (the labeled CFS, the labeled analogue, the complex between the analyte and the labeled CFS) not involved in formation of said complex and the coexisting materials in the blood-derived sample, by ITP, in the presence of the MES ion and/or the glutamate ion, and largely classified to the following two methods:

(1) A method for forming the complex relevant to the present invention, in advance, before carrying out ITP, to separate and concentrate the complex relevant to the present invention thus formed, by ITP (the separation method 1 of the present invention)

(2) A method for and separating and concentrating the complex relevant to the present invention, while forming the complex relevant to the present invention by ITP (while carrying out ITP) (the separation method 2 of the present invention)

2-1. The Separation Method 1 of the Present Invention

In this method, it is necessary to form, in advance, the complex (the complex A including the analyte, one or more kinds of mobility-changing CFSs and one or more kinds of the labeled CFSs, the complex A' including the labeled analogue and one or more kinds of the mobility-changing CFSs, and the complex A"including the mobility-changing analogue and one or more kinds of the labeled CFSs) relevant to the present invention, before carrying out the separation method (ITP) of the present invention. Then, ITP is carried out, in the presence of the MES ion and/or the glutamate ion, by making existed (introduced) a solution containing the complex formed, between the LB zone and the TB zone of inside of the capillary (hereafter may be abbreviated as the capillary for ITP) for carrying out ITP.

(1) Formation of the Complex

As a method for forming the complex relevant to the present invention, any method may be used as long as it is capable of forming the complex eventually, and, for example, there can be used a method for forming the complex known in itself (1-1) a method for forming the complex at the outside of the capillary (for example, JP-A-10-512371, WO2002/08208 etc.), (1-2) a method for forming the complex at the inside of the capillary (for example, JP-A-2005-31070, JP-A-2000-516343, JP-A-2003-202322 etc.), etc.

Among these, it is preferable to use the method for forming the complex at the inside of the capillary.

(1-1) The Method for Forming the Complex at the Outside of the Capillary

This may be carried out as follows in accordance with methods described in, for example, JP-A-10-512371, WO2002/082083 etc. (A method for forming the complex 1-1).

That is, in the case of the non-competitive method, by directly adding (a) the analyte in the blood-derived sample, (b) one or more kinds of the mobility-changing CFSs and (c) one or more kinds of the labeled CFSs, for example, into water or a buffer solution used in this field (for example, a buffer solution used in a hybridization method, an immune method, etc., such as Iris buffer, a phosphate buffer, Veronal buffer, a borate buffer, Good's buffer, SSC buffer, TBE buffer, TAE buffer) to dissolve, disperse or suspend and to make them contacted each other, a solution containing the complex A including these (a) to (c), and the free (c) labeled CFS not involved in formation of said complex A is obtained; or by once adding each of the above (a) to (c) into the above described water or the buffer solution, to dissolve, disperse or suspend and to prepare solutions, and by mixing these solutions each other and making the above (a) to (c) contacted, a solution containing the complex A including these (a) to (c), and the free (c) labeled CFS not involved in formation of said complex A is obtained.

In addition, in the case of the competitive method using the labeled analogue, by directly adding (a') the labeled analogue, (b) one or more kinds of the mobility-changing CFSs and (a)

the analyte in the blood-derived sample, for example, into water or the buffer solution as above-described, to dissolve, disperse or suspend and to make them contacted each other [contact of (a') the labeled analogue and (b) one or more kinds of the mobility-changing CFSs, and contact of (a) the analyte in the blood-derived sample and (b) one or more kinds of the mobility-changing CFSs], a solution containing the complex A' including (a') and (b), the complex B' including (a) and (b), and the free (a') labeled analogue not involved in formation of said complex A' (and B') is obtained; or by once adding each of the above (a), (a') and (b) into the water or the buffer solution as above-described to dissolve, disperse or suspend and to prepare solutions, and by mixing these solutions each other, or by mixing the solution including (a) and the solution including (a'), and then mixing this with the solution including (b), to make these contacted [contact of (a') the labeled analogue and (b) one or more kinds of the mobility-changing CFSs, and contact of (a) the analyte in the blood-derived sample and (b) one or more kinds of the mobility-changing CFSs], a solution containing the complex A'including (a') and (b), the complex B' including (a) and (b), and the free (a') labeled analogue not involved in formation of said complex A' (and B') is obtained.

Further, in the case of the competitive method using the mobility-changing analogue, by directly adding (a") the mobility-changing analogue, (c) one or more kinds of the labeled CFSs and (a) the analyte in the blood-derived sample, for example, into water or the buffer solution as above-described to dissolve, disperse or suspend and to make them contacted each other [contact of (a") the mobility-changing analogue and (c) one or more kinds of the labeled CFSs, and contact of (a) the analyte in the blood-derived sample and (c) one or more kinds of the labeled CFSs], a solution containing the complex A" including (a") and (c), the complex B" including (a) and (c), and the free (a") mobility-changing analogue not involved in formation of said complex A" (and B") is obtained; or by once adding for dissolving, dispersing or suspending each of the above (a), (a") and (c), into the above described water or the buffer solution, to prepare solutions, and by mixing these solutions each other, or by mixing the solution including (a) and the solution including (a"), and then mixing this with the solution including (c), to make these contacted [contact of (a") the mobility-changing analogue and (c) one or more kinds of the labeled CFSs, and contact of (a) the analyte in the blood-derived sample and (c) one or more kinds of the labeled CFSs], a solution containing the complex A" including (a") and (c), the complex B" including (a) and (c), and the free (c) labeled analogue not involved in formation of said complex A" (and B") is obtained.

(1-2) The Method for Forming the Complex at the Inside of the Capillary

This may be carried out as follows in accordance with a method described, for example, in JP-A-2005-31070 etc. (A method for forming the complex 1-2-1).

That is, in the case of the non-competitive method, by introducing the above solution including (a) the blood-derived sample including the analyte (or the above solution including the sample), the above solution including (b) one or more kinds of the mobility-changing CFSs, and the above solution including (c) one or more kinds of the labeled CFSs, to the inside of the capillary for mixing from a different capillary (channel), respectively, to be subjected these to mixing and reaction at the inside of said capillary for mixing, a solution containing the complex A including these (a) to (c) and the free (c) labeled CFS not involved in formation of said complex A is obtained; or by introducing the solution including two kinds among the above (a) to (c) and the solution including the residual one kind, to the inside of the capillary for mixing, to be subjected these to mixing and reaction at the inside from a different capillary (channel) of said capillary for mixing, respectively, a solution containing the complex A including these (a) to (c) and the free (c) labeled CFS not involved in formation of said complex A is obtained.

In addition, in the case of the competitive method using the labeled analogue, by introducing the above solution including (a') the labeled analogue, the above solution including (b) one or more kinds of the mobility-changing CFSs, and (a) the blood-derived sample including the analyte (or the above solution including the sample), to the inside of the capillary for mixing from a different capillary (channel), respectively, to be subjected these to mixing and reaction [by a reaction between (a') the labeled analogue and (b) one or more kinds of the mobility-changing CFSs, and by a reaction between (a) the analyte in the blood-derived sample and (b) one or more kinds of the mobility-changing CFSs] at the inside of said capillary for mixing, a solution containing the complex A'including (a') and (b), the complex B' including (a) and (b), and the free (a') labeled CFS not involved in formation of said complex A' (and B') is obtained; or by introducing the solution including two kinds among the above (a), (a') and (b), and the solution including the residual one kind, (channel) to the inside of the capillary for mixing from a different capillary, respectively, to be subjected these to mixing and reaction [by a reaction between (a') the labeled analogue and (b) one or more kinds of the mobility-changing CFSs, and by a reaction between (a) the analyte in the blood-derived sample and (b) one or more kinds of the mobility-changing CFSs] at the inside of said capillary for mixing, a solution containing the complex A'including (a') and (b), the complex B' including (a) and (b), and the free (a') labeled analogue not involved in formation of said complex A' (and B') is obtained.

Further, in the case of the competitive method using the mobility-changing analogue, by introducing (a") the above solution including the mobility-changing analogue, (c) the above solution including one or more kinds of the labeled CFSs, and (a) the blood-derived sample including analyte (or the above solution including the sample), to the inside of the capillary for mixing from a different capillary (channel), respectively, to be subjected these to mixing and reaction [by a reaction between (a") the mobility-changing analogue and (c) one or more kinds of the labeled CFSs, and by a reaction between (a) the analyte in the blood-derived sample and (c) one or more kinds of the labeled CFSs] at the inside of said capillary for mixing, a solution containing the complex A" including (a") and (c), the complex B" including (a) and (c), and the free (a") the mobility-changing analogue not involved in formation of said complex A" (and B") is obtained; or by introducing the solution including two kinds among the above (a), (a") and (c), and the solution including the residual one kind, to the inside of the capillary for mixing from a different capillary (channel), respectively, to be subjected these to mixing and reaction [by a reaction between (a") the mobility-changing analogue and (c) one or more kinds of the labeled CFSs, and by a reaction between (a) the analyte in the blood-derived sample and (c) one or more kinds of the labeled CFSs] at the inside of said capillary for mixing, a solution containing the complex A" including (a") and (c), the complex B" including (a) and (c), and the free (c) labeled analogue not involved in formation of said complex A" (and B") is obtained.

In addition, this may also be carried out as follows in accordance with methods described, for example, in JP-A-2000-516343, JP-A-2003-202322 etc. (A method for forming the complex 1-2-2).

That is, in the case of the non-competitive method, after arranging (a) the blood-derived sample including the analyte (or the above solution including the sample), (b) the above solution including one or more kinds of the mobility-changing CFSs, and (c) the above solution including one or more kinds of the labeled CFSs, at the inside of the capillary for analysis, so that a sample or a solution containing a substance having higher electrophoretic mobility (faster electrophoretic mobility), among the analyte, the mobility-changing CFSs and the labeled CFSs, is located at the upstream of a sample or a solution containing a substance having lower electrophoretic mobility (slower electrophoretic mobility), a solution containing the complex A including these (a) to (c) and the free (c) labeled CFS not involved in formation of said complex A is obtained by making them contacted and reacted electrophoretically, in a manner that the substance having higher electrophoretic mobility overtakes the substance having lower electrophoretic mobility by applying electric field (by an electrophoresis method other than ITP); or after arranging a solution including the two kinds among the above (a) to (c) [a solution including (a) and (b) (a solution including the analyte—the mobility-changing CFS intermediate complex), a solution including (a) and (c) (a solution including the analyte—the labeled CFS intermediate complex) or a solution including (b) and (c)] and a solution including the residual one kind, at the inside of the capillary for analysis, so that a sample or a solution containing a substance having higher electrophoretic mobility (faster electrophoretic mobility), among the analyte, the mobility-changing CFSs, the labeled CFSs, the analyte—the mobility-changing CFS intermediate complex and the analyte—the labeled CFS intermediate complex, is located at the upstream of a sample or a solution containing a substance having lower electrophoretic mobility (slower electrophoretic mobility), a solution containing the complex A including these (a) to (c) and the free (c) labeled CFS not involved in formation of said complex A is obtained by making them contacted and reacted electrophoretically, in a manner that the substance having higher electrophoretic mobility overtakes the substance having lower electrophoretic mobility by applying electric field (by an electrophoresis method other than ITP)

In addition, in the case of the competitive method using the labeled analogue, after arranging, (a') the above solution including the labeled analogue, (b) the above solution including one or more kinds of the mobility-changing CFSs, and (a) the blood-derived sample including the analyte (or the above solution including the sample), at the inside of the capillary for analysis, so that a sample or a solution containing a substance having higher electrophoretic mobility (faster electrophoretic mobility), among the labeled analogue, the mobility-changing CFSs and the analyte, is located at the upstream of a sample or a solution containing a substance having lower electrophoretic mobility (slower electrophoretic mobility), a solution containing the complex A' including (a') and (b), the complex B' including these (a) and (b), and the free (a') labeled analogue not involved in formation of said complex A' (and B') is obtained by making them contacted and reacted electrophoretically [by a reaction between (a') the labeled analogue and (b) one or more kinds of the mobility-changing CFSs, and by a reaction between (a) the analyte in the blood-derived sample and (b) one or more kinds of the mobility-changing CFSs] in a manner that the substance having higher electrophoretic mobility overtakes the substance having lower electrophoretic mobility, by applying electric field (by an electrophoresis method other than ITP); or after arranging, a solution including the two kinds among the above (a), (a') and (b) [a solution including (a') and (a), a solution including (a') and (b) (a solution including the labeled analogue—the mobility-changing CFS complex), or a solution including (a) and (b) (a solution including the analyte—the mobility-changing CFS complex)] and a solution including the residual one kind, at the inside of the capillary for analysis, so that a sample or a solution containing a substance having higher electrophoretic mobility (faster electrophoretic mobility), among the analyte, the labeled analogue, the mobility-changing CFSs, the labeled analogue—the mobility-changing CFS complex, and the analyte—the mobility-changing CFS complex, is located at the upstream of a sample or a solution containing a substance having lower electrophoretic mobility (slower electrophoretic mobility), a solution containing the complex A' including (a') and (b), the complex B' including (a) and (b), and the free (a') labeled analogue not involved in formation of said complex A' (and B') is obtained by making them contacted and reacted electrophoretically [by a reaction between (a') the labeled analogue and (b) one or more kinds of the mobility-changing CFSs, and by a reaction between (a) the analyte in the blood-derived sample and (b) one or more kinds of the mobility-changing CFSs], in a manner that the substance having higher electrophoretic mobility overtakes the substance having lower electrophoretic mobility, by applying electric field (by an electrophoresis method other than ITP).

Further, in the case of the competitive method using the mobility-changing analogue, after arranging, (a") the above solution including mobility-changing analogue, (c) the above solution including one or more kinds of the labeled CFSs, and (a) the blood-derived sample including the analyte (or the above solution including the sample), at the inside of the capillary for analysis, so that a sample or a solution containing a substance having higher electrophoretic mobility (faster electrophoretic mobility), among mobility-changing analogue, the labeled CFSs and the analyte, is located at the upstream of a sample or a solution containing a substance having lower electrophoretic mobility (slower electrophoretic mobility), a solution containing the complex A" including (a") and (c), the complex B" including (a) and (c), and the free (a") mobility-changing analogue not involved in formation of said complex A" (and B") is obtained by making them contacted and reacted electrophoretically [by a reaction between (a") mobility-changing analogue and (c) one or more kinds of the labeled CFSs, and by a reaction between (a) the analyte in the blood-derived sample and (c) one or more kinds of the labeled CFSs], in a manner that the substance having higher electrophoretic mobility overtakes the substance having lower electrophoretic mobility, by applying electric field (by an electrophoresis method other than ITP); or after arranging, a solution including the two kinds among the above (a), (a") and (c) [a solution including (a") and (a), a solution including (a) and (c) (a solution including the analyte-labeled CFS complex), or a solution including (a") and (c) (a solution including mobility-changing analogue—the labeled CFS complex)]and a solution including the residual one kind, at the inside of the capillary for analysis, so that a sample or a solution containing a substance having higher electrophoretic mobility (faster electrophoretic mobility), among the analyte, the mobility-changing analogue, the labeled CFS, the analyte—the labeled CFS complex, and the mobility-changing analogue—the labeled CFS complex, is located at the upstream of a sample or a solution containing a substance having lower electrophoretic mobility (slower electrophoretic mobility), a solution containing the complex A" including (a") and (c), the complex B" including these (a) and (c), and the free (c) labeled analogue not involved in formation of said complex A" (and B") is obtained by making contacted and reacted electrophoretically [by a reaction between (a") mobility-changing analogue and (c) one or more kinds of the labeled CFSs, and by a reaction between (a) the analyte in the blood-derived sample and (c) one or more kinds of the labeled CFSs], in a manner that the substance having higher electrophoretic mobility overtakes the substance having lower electrophoretic mobility, by applying electric field (by an electrophoresis method other than ITP).

(2) ITP

By making existed (introduced) a solution containing the complex relevant to the present invention formed as above [a solution containing the complex A and the free labeling CFS not involved in formation of said complex A, a solution containing the complex A', the complex B' and the free labeling CFS not involved in formation of said complex A' (and B'), or a solution containing the complex A", the complex B" and the free labeling CFS not involved in formation of said complex A" (and B")], between the LB zone and the TB zone at the inside of the capillary for ITP, to carry out ITP, in the presence of the MES ion and/or the glutamate ion, separation and concentration of the complex relevant to the present invention are carried out.

That is, the separation method 1 of the present invention includes specifically the following steps (1) and (2):

(1) A Step of Introducing any Solutions of the Following [I-1] to [I-3], between the LB Zone and the TB Zone at the inside of the Capillary for ITP (a Step of Introduction):

(1) a step of introducing any solutions of the following [I-1] to [I-3], between an LB zone and a TB zone at the inside of a capillary for carrying out ITP (a step of introduction):

[I-1] a solution containing the complex A comprising the following (a) to (c) obtained by contacting (a) the analyte in the blood-derived sample, (b) one or more kinds of the mobility-changing CFSs and (c) one or more kinds of the labeled CFCs, and the free (c) labeled CFS not involved in formation of said complex A;

[I-2] a solution containing the complex A' comprising the following (a') and (b), obtained by contacting (a') the labeled analogue and (b) one or more kinds of the mobility-changing CFSs, and the complex B' comprising the following (a) and (b), obtained by contacting (a) the analyte in the blood-derived sample and (b) one or more kinds of the mobility-changing CFSs, and the free (a') labeled analogue not involved in formation of said complex A';

[I-3] a solution containing the complex A" comprising the following (a") and (c), obtained by contacting (a") the mobility-changing analogue and (c) one or more kinds of the labeled CFSs, the complex B" comprising the following (a) and (c), obtained by contacting (a) the analyte in the blood-derived sample and (c) one or more kinds of the labeled CFSs, and the free (c) labeled CFS not involved in formation of said complex A"; and (2) a step of carrying out any separation of the following [A-1] to [A-3], while concentrating said complex A, said complex A' or said complex A" by ITP, by applying a voltage onto the capillary, in the presence of an MES ion and/or a glutamate ion, at the downstream side of the TB zone (a step of concentration and separation):

[A-1] separation of (i) said complex A from (ii) the free (c) labeled CFS not involved in formation of said complex A, and (iii) the coexisting substances in the blood-derived sample;

[A-2] separation of (i) said complex A' from (ii) the free (a') labeled analogue not involved in formation of said complex A', and (iii) the coexisting substances in the blood-derived sample;

[A-3] separation of (i) said complex A" from (ii) the free (c) labeled CFS not involved in formation of said complex A" and/or said complex B", and (iii) the coexisting substances in the blood-derived sample.

(2-1) The Step of Introduction

The step of introduction is a step (the step of introduction and arrangement) of making existed a solution containing the complex relevant to the present invention [a solution containing the complex A and the free labeling CFS not involved in formation of said complex A, a solution containing the complex A', the complex B' and the free labeling CFS not involved in formation of said complex A' (and B'), or a solution containing the complex A", the complex B" and the free labeling CFS not involved in formation of said complex A" (and B")] between the LB zone and the TB zone at the inside of the capillary for ITP, to carry out ITP, in the presence of the MES ion and/or the glutamate ion.

As a method for introducing the solution containing the complex relevant to the present invention to the inside of the capillary for ITP, in the step of introduction, any introduction method known itself may be used, as long as it is a method capable of making existed (introduced and arranged) said solution between the LB zone and the TB zone at the inside of the capillary for ITP.

In more specifically, in the case where a solution containing the complex relevant to the present invention [a solution containing the complex A and the free labeling CFS not involved in formation of said complex A, a solution containing the complex A', the complex B' and the free labeling CFS not involved in formation of said complex A' (and B'), or a solution containing the complex A", the complex B" and the free labeling CFS not involved in formation of said complex A" (and B")] was obtained by a method for forming the complex, for example, by the above (1-1) the method for forming the complex at the outside of capillary, for example, there can be used, a method for electrically introducing the solution to the inside of the capillary, by applying a voltage onto the capillary; a method for introducing the solution to the inside of the capillary, by pressurization and/or depressurization of the inside of the capillary; a method for introducing the solution to the inside of the capillary, by utilization of capillary phenomenon, etc.

In addition, as a method for introducing and arranging the solution containing the complex relevant to the present invention, between the LB zone and the TB zone at the inside of the capillary for ITP, any introducing and arranging method known itself can be used. As such an introducing and arranging method known itself, for example, there are included (1) a method for introducing firstly the LB (or the TB) from the tip of the capillary to the inside of the capillary by the above described introduction method, and then introducing similarly the solution containing the complex relevant to the present invention from the tip of the capillary by the above described introduction method, and after that, introducing similarly the TB (or the LB) from the tip of the capillary to the inside of the capillary to arrange all of the solutions at the inside of the capillary for ITP, (2) a method for dropping the LB (or the TB) firstly in a liquid reservoir (well) to introduce this to the inside of the capillary by the above introduction method, then, after replacing the solution in the liquid reservoir (well) with the solution containing the complex relevant to the present invention, introducing this similarly to the inside of the capillary by the above described introduction method, and further, after replacing the solution at the inside of the liquid reservoir (well) with the TB (or the LB), introducing this similarly by the above described introduction method, to arrange all of the solutions at the inside of the capillary for ITP, (3) a method for dropping the LB, the solution containing the complex relevant to the present invention and the TB, separately, into each of a plurality of liquid reservoirs (wells), and introducing these separately to the inside of the same capillary by the above described introduction method, to arrange all of the solutions at the inside of the capillary for ITP, etc.

In addition, in the case where the solution containing the complex relevant to the present invention [a solution including the complex A and the free labeling CFS not involved in formation of said complex A, a solution including the complex A', the complex B' and the free labeling analogue not involved in formation of said complex A' (and B'), or a solution including the complex A", the complex B" and the free labeling analogue not involved in formation of said complex A" (and B")] was obtained by, for example, the above (1-2) method for forming the complex at the inside of capillary, the solution containing the complex relevant to the present invention can be introduced and arranged between the LB zone and the TB zone at the inside of the capillary for ITP, by the same method as above.

In addition, in this case, for example, after forming the complex relevant to the present invention at the inside of the capillary, the solution (zone) containing the complex relevant to the present invention can be electrically moved to be introduced and arranged as well, between the LB zone and the TB zone at the inside of the capillary for ITP.

(2-2) A Step of Concentration and Separation

The step of concentration and separation in the separation method 1 of the present invention is a step of separating the following complex from the free labeling substance-containing molecule (the labeled CFS, the labeled analogue, and the analyte-labeled CFS complex) not involved in formation of said complex, and the coexisting materials in the blood-derived sample, while concentrating the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A"including the mobility-changing analogue and one or more kinds of the labeled CFSs) at the downstream side of the TB zone (in more specifically, the downstream side of the trailing ion), by applying a voltage onto the capillary for ITP, arranged so as to be the TB zone/the solution (zone) containing the complex relevant to the present invention/the LB zone by the above introduction step, in the presence of the MES ion and/or the glutamate ion, namely, by carrying out ITP, in the presence of the MES ion and/or the glutamate ion.

In the step of concentration and separation, "to concentrate the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A"including the mobility-changing analogue and one or more kinds of the labeled CFSs) by applying a voltage onto both sides of the capillary" means a state that the complex relevant to the present invention assemble band-likely (plug-likely), in applying a voltage onto both sides of the capillary for ITP (in carrying out ITP). In other words, it means that in applying a voltage onto both sides of the capillary for ITP (in carrying out ITP), said complex assemble to generate a portion having higher concentration of said complex than concentration of the complex in a zone arranged by the introduction step, namely, in applying a voltage onto both sides of the capillary for ITP (in carrying out ITP), the complex relevant to the present invention assemble to generate a portion having higher concentration of said complex than concentration of the complex relevant to the present invention in a solution zone containing the complex relevant to the present invention (a solution zone in the above [I-1], a solution zone in the above [I-2], and a solution zone in the above [I-3]), arranged by the introduction step.

In this connection, as rate (degree) of concentration in the present invention, concentration of said complex of the assembled portion (band-likely), in applying a voltage onto the capillary for ITP (in carrying out ITP), is usually equal to or higher than 1.5 time, preferably equal to or higher than 5 times, more preferably equal to or higher than 10 times and further preferably equal to or higher than 25 times, as the lower limit, and the upper limit is not especially limited, however, usually equal to or lower than $10^5$ times, preferably equal to or lower than $10^4$ times, and more preferably equal to or lower than 2000 times, relative to concentration of the complex relevant to the present invention in the zone arranged by the introduction step.

In the step of concentration and separation, the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analogue and one or more kinds of the labeled CFSs) obtained by the above formation of the complex is separated from the free labeling substance-containing molecule (the labeled CFS, the labeled analogue, and the analyte-labeled CFS complex) not involved in formation of said complex, and the coexisting materials in the blood-derived sample at the inside of the capillary for ITP while moving them electrically.

For example, in the case of the non-competitive method, it is enough to separate at least the complex A from the free labeled CFS, not involved in formation of said complex A, and the coexisting materials in the blood-derived sample, and it is not necessary to separate the mobility-changing CFS from said complex.

In addition, in the case of the competitive method using, for example, the labeled analogue, it is enough to separate at least the complex A' from the free labeled analogue not involved in formation of said complex A', and the coexisting materials in the blood-derived sample, and it is not necessary to separate the mobility-changing CFS or the complex B' (the complex of the analyte and the mobility-changing CFS) from said complex. In addition, in the case of the competitive method using the mobility-changing analogue, it is enough to separate at least the complex A" from the complex B" and the free labeled CFS not involved in formation of and said complex A" (and the complex B"), along with the coexisting materials in the blood-derived sample.

(2-2-1) The MES Ion and the Glutamate Ion

As the MES ion to be used in the present invention, for example, one derived from a hydrate such as a mono-hydrate; for example, one derived from an alkali metal salt such as a sodium salt, a potassium salt or a lithium salt can be used, and not especially limited, and MES itself can be used as well.

In addition, the glutamate ion is not especially limited and, for example, L-glutamic acid itself, D-glutamic acid itself, etc. can be used. In addition, one derived from an alkali metal salt such as sodium glutamate, or one derived from a hydrate thereof etc. can be used as well.

These MES ion and glutamate ion can be used alone, or both can be used in combination. In addition, among these, the MES ion is particularly preferable.

In the separation method 1 of the present invention, a method for making the MES ion and/or the glutamate ion existed in carrying out ITP is not especially limited, as long as it is capable of carrying out ITP, in the presence of the MES ion and/or the glutamate ion eventually.

As such a method, for example, in (1-1) the method for forming the complex at the outside of the capillary, there are included a method for making coexisted the MES ion and/or the glutamate ion, in advance, in a solution containing (a) the analyte in the blood-derived sample, (b) one or more kinds of the mobility-changing CFSs and (c) one or more kinds of the labeled CFSs, a solution containing (a') the labeled analogue, (b) one or more kinds of the mobility-changing CFSs and (a) the analyte in the blood-derived sample, or a solution containing (a'') the mobility-changing analogue, (c) one or more kinds of the labeled CFSs and (a) the analyte in the blood-derived sample; a method for making coexisted the MES ion and/or the glutamate ion, in advance, for example, in any one or more kinds of a solution containing (a), a solution containing (b) and a solution containing (c), in any one or more kinds of a solution containing (a'), a solution containing (b) and a solution containing (a), or in any one or more kinds of a solution containing (a''), a solution containing (c) and a solution containing (a); etc.

In addition, in (1-2) the method for forming the complex at the inside of the capillary, there are included a method for making coexisted the MES ion and/or the glutamate ion, in advance, in any one or more kinds of (a) the blood-derived sample including the analyte (or the above solution including the sample), (b) the above solution including one or more kinds of the mobility-changing CFSs and (c) the solution including one or more kinds of the labeled CFSs; a solution including two kinds among (a) to (c) and/or a solution including the residual one kind; any one or more kinds of (a') the above solution including the labeled analogue, (b) the above solution including one or more kinds of the mobility-changing CFSs, and (a) the blood-derived sample including the analyte (or the above solution including the sample); and the solution including two kinds among (a), (a') and (b), and/or the solution including the residual one kind; or one or more kinds of any of the above solution including (a'') the mobility-changing analogue, (c) the above solution including one or more kinds of the labeled CFSs, and (a) the above solution containing the blood-derived sample including the analyte (or the above solution including the sample); the solution including two kinds among (a), (a'') and (c), and/or the solution including the residual one kind.

In this connection, the MES ion and/or the glutamate ion may be made coexisted in the LB and/or the TB, however, it is preferable to be made coexisted in the solutions (the solutions as above) to be introduced and arranged between the LB zone and the TB zone at the inside of the capillary for ITP.

Among these, it is particularly preferable that the MES ion and/or the glutamate ion are made coexisted in the solution containing the blood-derived sample including the analyte [in the solution containing (a), (b) and (c), the solution containing (a'), (b) and (a), the solution containing (a''), (c) and (a), the solution containing (a) and (b) or (c), the solution containing (a) and (a') or (b), the solution including (a) and (a'') or (c), or the solution including (a)].

Use amount of the MES ion is, as concentration in a solution making contained the MES ion, usually equal to or higher than 0.005 mM, preferably equal to or higher than 0.05 mM, more preferably equal to or higher than 0.5 mM, and particularly preferably equal to or higher than 1 mM, as the lower limit; and as the upper limit, equal to or lower than 100 mM, preferably equal to or lower than 20 mM, and more preferably equal to or lower than 10 mM.

In addition, use amount of the glutamate ion is, as concentration in a solution making contained the glutamate ion, usually equal to or higher than 0.005 mM, preferably equal to or higher than 0.05 mM, more preferably equal to or higher than 0.5 mM, and particularly preferably equal to or higher than 1 mM, as the lower limit; and as the upper limit, equal to or lower than 100 mM, preferably equal to or lower than 20 mM, and more preferably equal to or lower than 10 mM.

(2-2-2) LB and TB

The LB to be used in the separation method 1 of the present invention is an electrophoresis medium including a leading ion having faster electrophoretic speed than that of at least the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A'' including the mobility-changing analogue and one or more kinds of the labeled CFSs). In this connection, the LB is arranged at the downstream side of the solution containing the complex relevant to the present invention.

In the above, as the leading ion, one selected from those to be used usually in this field, as appropriate, can be used, and includes, for example, a chlorine ion ($Cl^-$) etc. In addition, use concentration of the leading ion may be selected, as appropriate, from those to be used usually in this field and is, for example, usually 1 µM to 10 M, preferably 100 µM to 1 M, and more preferably 1 mM to 500 mM.

Also, the LB including such a leading ion is used by selecting, as appropriate, from those to be used usually in this field and for example, Tris buffer, Bis-tris buffer, borate buffer, phosphate buffer, histidine buffer, imidazole buffer, glycin buffer. Among these, Iris buffer and Bis-tris buffer are preferable, and Tris buffer is particularly preferable. Use amount and pH thereof may be selected, as appropriate, from a range to be used usually in this field, and the use amount is, for example, usually 1 µM to 10 M, preferably 100 µM to 1 M, and more preferably 1 mM to 500 mM, and the pH is usually 2 to 12, preferably 4 to 10 and more preferably 6 to 9.

In addition, the TB to be used in the separation method 1 of the present invention is an electrophoresis medium including the trailing ion having slower electrophoretic mobility than that of at least the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A''including the mobility-changing analogue and one or more kinds of the labeled CFSs). In this connection, the TB is arranged at the upstream side of the solution containing the complex relevant to the present invention.

In the above, as the trailing ion, one selected, as appropriate, from those to be used usually in this field can be used, including, for example, HEPES, TAPS, MOPS, glycin, threonine etc. Among these, HEPES and TAPS are preferable, and HEPES is particularly preferable. In addition, concentration of the trailing ion may also be selected, as appropriate, from those to be used usually in this field, and is, for example, usually 1 µM to 10 M, preferably 100 µM to 1 M, and more preferably 1 mM to 500 mM.

Also, the TB including such a trailing ion may be selected, as appropriate, from those to be used usually in this field, and for example, Tris buffer, bis-Tris buffer, a borate buffer, a phosphate buffer, a histidine buffer, an imidazole buffer, a glycine buffer etc. are included. Among these, Tris buffer, and bis-Tris buffer are preferable and Tris buffer is particularly preferable. Use amount and pH thereof may be selected, as appropriate, from ranges to be used usually in this field, and the use amount is, for example, usually 1 µM to 10 M, preferably 100 µM to 1 M, and more preferably 1 mM to 500 mM, and the pH is usually 2 to 12, preferably 4 to 10 and more preferably 6 to 9.

In addition, as a method for introducing and arranging the LB and the TB at the inside of the capillary for ITP, an introduction method known itself can be used, as long as it is a method capable of making said solution existed (making it introduced and arranged) at the LB zone and the TB zone at the inside of the capillary.

As such an introduction method known itself, an introduction and arrangement method for the solution containing the complex relevant to the present invention in the above introduction step etc. is included.

(2-2-3) ITP Conditions (Applied Voltage, pH, Temperature and Time)

As the step of concentration and separation in the separation method 1 of the present invention, it is enough to carry out ITP, in the presence of the MES ion and the glutamate ion, and any of ITP methods known themselves can be used [for example, Everaerts, F. M., Geurts, M. Mikkers, F. E. P., Verheggen, T. P. E. M J. Chromatagr. 1976, 119, 129-155; Mikkers, F. E. P., Everaerts, F. M., Peek, J. A. F. J. Chromatogr. 1979, 168, 293-315; Mikkers, F. E. P., Everaerts, F. M., Peek, J. A. F. J. Chromatogr. 1979, 168, 317-332; Hirokawa, T, Okamoto, H. Ikuta, N., and Gas, B., Analytical Sciences 2001, Vol. 17 Supplement il85 etc.].

In addition, also other reagents, operation methods and other conditions etc. can be selected, as appropriate, according to description of the above literature etc.

Applied voltage in the step of concentration and separation may be in a range where the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A"including the mobility-changing analogue and one or more kinds of the labeled CFSs) are sufficiently concentrated, and the complex relevant to the present invention can be separated from the free labeling substance-containing molecule (the labeled CFS, the labeled analogue, and the analyte-labeled CFS complex) not involved in formation of said complexes, and the coexisting materials in the blood-derived sample; and it may be selected, as appropriate, from those to be used usually in this field. In more specifically, voltage is applied so that there is attained an electric field intensity in a range of, as the lower limit, usually equal to or higher than 5 V/cm, preferably equal to or higher than 10 V/cm, more preferably equal to or higher than 50 V/cm, further preferably equal to or higher than 500 V/cm, and particularly preferably equal to or higher than 1000 V/cm, and as the upper limit, usually equal to or lower than 10000 V/cm, preferably equal to or lower than 5000 V/cm, and more preferably equal to or lower than 2000 V/cm.

In addition, other ITP conditions (for example, pH, temperature, time etc.) may be in a range not to disturb concentration of the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A"including the mobility-changing analogue and one or more kinds of the labeled CFSs), and separation of the complex relevant to the present invention from the free labeling substance-containing molecule (the labeled CFS, the labeled analogue, and the analyte-labeled CFS complex) not involved in formation of said complex, and the coexisting materials in the blood-derived sample.

Specifically, the pH is, as the lower limit, usually equal to or higher than 2, preferably equal to or higher than 5, and as the upper limit, usually equal to or lower than 10, preferably equal to or higher than 9, and the temperature is, as the lower limit, usually equal to or higher than 0° C., preferably equal to or higher than 5° C., more preferably equal to or higher than 10° C., and as the upper limit, usually equal to or lower than 50° C., preferably equal to or higher than 40° C. and more preferably equal to or lower than 30° C.

The ITP time differs depending on association constant of the CFS to be used to the analyte or the analogue thereof, and the case of lower association constant requires relatively longer reaction time, while the case of higher association constant requires relatively shorter reaction time. In more specifically, for example, the lower limit is usually equal to or longer than 10 seconds, preferably equal to or longer than 30 seconds, and more preferably equal to or longer than 1 minute, and the upper limit is usually equal to or shorter than 60 minutes, preferably equal to or shorter than 10 minutes, and more preferably equal to or shorter than 5 minutes.

2-2. The Separation Method 2 of the Present Invention

The separation method 2 of the present invention is characterized by separating the following labeling substance-containing complex (the complex A, the complex A' and the complex A" relevant to the present invention) from the free labeling substance-containing molecule (the labeled CFS, the labeled analogue, and the analyte-labeled CFS complex) not involved in formation of said labeling substance-containing complex, and the coexisting materials in the blood-derived sample, while concentrating the complex containing the labeling substance (the complex A, the complex A' and the complex A"relevant to the present invention) among the following complex, at the downstream of the TB zone (1) by introducing and arranging a plurality of solutions selected from a solution containing the analyte, a solution containing the analogue (the labeled analogue or the mobility-changing analogue), a solution containing the analyte and the analogue, a solution containing the CFS (the labeled CFS and/or the mobility-changing CFS) and a solution containing the analyte or analogue and the CFS, between the LB zone and the TB zone at the inside of the capillary for ITP, so as to form each separate zone without mixing these solutions, in advance, at the outside of the capillary for ITP, to form the complex including the analyte and/or the complex including the analogue; and then (2) by applying a voltage onto both sides of said capillary, in the presence of the MES ion and/or the glutamate ion, to make said analyte and the CFS (the labeled CFS and/or the mobility-changing CFS) contacted electrophoretically by ITP, before these solutions are uniformly mixed at the inside of said capillary, or to make said analyte, the analogue thereof (the labeled analogue and/or the mobility-changing analogue) and the CFS (the labeled CFS and/or the mobility-changing CFS) contacted electrophoretically, and forming the complex including the analyte and/or the complex including the analogue.

That is, the separation method 2 of the present invention based on the non-competitive method includes the following steps (1) and (2) specifically:

(1) a step of introducing a plurality of solutions comprising a combination described in any of the following [I-1]to [I-2], between the LB zone and the TB zone at the inside of the capillary for carrying out ITP, without mixing these solutions, in advance, and so that each of them forms a separate zone (a step of introduction):

[I-1] 1) a solution containing one or more kinds of the labeled CFSs, 2) a solution containing an blood-derived sample including an analyte, and 3) a solution containing one or more kinds of the mobility-changing CFSs;

[I-2] 1) a solution containing the blood-derived sample including the analyte and one or more kinds of the labeled CFSs, and 2) a solution containing one or more kinds of the mobility-changing CFSs, and (2) [A] a step of separating (i) the following complex A from (ii) the following free (c) labeled CFS not involved in formation of said complex A, and (iii) the coexisting substances in the blood-derived sample, while concentrating the following complex A formed by method of the following [II-1] or [II-2]by ITP, by applying a voltage onto said capillary, in the presence of the MES ion and/or the glutamate ion, at the downstream side of the TB zone (a step of concentration and separation):

[II-1] a method for forming the complex A comprising the following (a) to (c), by contacting (a) said analyte, (b) one or more kinds of the mobility-changing CFSs and (c) one or more kinds of the labeled CFSs;

[II-2] a method for forming the complex A comprising the following (a) to (c), by contacting a complex comprising (a) said analyte and (c) one or more kinds of the labeled CFSs, and (b) one or more kinds of the mobility-changing CFSs.

In addition, the separation method 2 of the present invention, based on the competitive method includes the following steps (1) and (2) specifically:

(1) a step of introducing a plurality of solutions comprising a combination as set forth in any of the following [I-1] to [I-7], between the LB zone and the TB zone at the inside of the capillary for carrying out ITP, without mixing these solutions, in advance, and so that each of them forms a separate zone (a step of introduction):

[I-1] 1) a solution containing the blood-derived sample including the analyte and the labeled analogue, and 2) a solution containing one or more kinds of the mobility-changing CFSs;

[I-2] 1) a solution containing the blood-derived sample including the analyte, and 2) a solution containing the labeled analogue and one or more kinds of the mobility-changing CFSs;

[I-3] 1) a solution containing the labeled analogue, and 2) a solution containing the blood-derived sample including the analyte and one or more kinds of the mobility-changing CFSs;

[I-4] 1) a solution containing the blood-derived sample including the analyte, 2) a solution containing the labeled analogue, and 3) a solution containing one or more kinds of the mobility-changing CFSs;

[I-5] 1) a solution containing the labeled analogue, 2) a solution containing the blood-derived sample including the analyte, and 3) a solution containing one or more kinds of the mobility-changing CFSs;

[I-6] 1) a solution containing the blood-derived sample including the analyte, and 2) a solution containing the mobility-changing analogue and one or more kinds of the labeled CFSs; and

[I-7] 1) a solution containing the blood-derived sample including the analyte and one or more kinds of the labeled CFSs, and 2) a solution containing the mobility-changing analogue; and (2) a step of carrying out separation of any of the following [A-1] or [A-2], while concentrating the following complex A' or the following complex A", which was formed by any methods of the following [II-1] to [II-7], by ITP, by applying a voltage onto said capillary, in the presence of the MES ion and/or the glutamate ion, at the downstream side of the TB zone (a step of concentration and separation):

[II-1] a method for forming the complex A' comprising the following (a') and (b), by contacting (a') the labeled analogue and (b) one or more kinds of the mobility-changing CFSs, and the complex B' comprising the following (a) and (b), by contacting (a) said analyte and (b) one or more kinds of the mobility-changing CFSs;

[II-2] a method for forming the complex B comprising the following (a) and (b), by contacting (a) said analyte, and the complex A' between (a') the labeled analogue and (b) one or more kinds of the mobility-changing CFSs, present in the solution of the [I-2] 2);

[II-3] a method for forming the complex A' comprising the following (a') and (b), by contacting (a') the labeled analogue, and the complex B' between (a) said analyte and (b) one or more kinds of the mobility-changing CFSs, present in the solution of the [I-3] 2), and/or by contacting (a') said labeled analogue, and (b) one or more kinds of the mobility-changing CFSs not involved in formation of the complex B';

[II-4] a method for forming the complex A' between the following (a') and (b), by contacting (a') the labeled analogue and (b) one or more kinds of the mobility-changing CFSs, and then for forming the complex B' comprising the following (a) and (b), by contacting (a) said analyte and said complex A';

[II-5] a method for forming the complex B' between the following (a) and (b), by contacting (a) said analyte and (b) one or more kinds of the mobility-changing CFSs, and then for forming the complex A' comprising the following (a') and (b), by contacting (a') the labeled analogue and said complex B'and/or by contacting (a') the labeled analogue and (b) one or more kinds of the mobility-changing CFSs not involved in formation of the complex B';

[II-6] a method for forming the complex B" comprising the following (a) and (c), by contacting (a) said analyte, and the complex A" between (a") the mobility-changing analogue and (c) one or more kinds of the labeled CFSs, present in the solution of the [I-6] 2); and

[II-7] a method for forming the complex A" comprising the following (a") and (c), by contacting (a") the mobility-changing analogue and the complex B" between (a) said analyte and (c) one or more kinds of the labeled CFSs, present in the solution of the [I-7] 1), and/or by contacting (a") the mobility-changing analogue and (c) one or more kinds of the labeled CFSs not involved in formation of the complex B";

[A-1] separation of (i) said complex A' from (ii) the free (a') labeled analogue not involved in formation of said complex A' and (iii) the coexisting substances in the blood-derived sample;

[A-2] separation of (i) said complex A" from (ii) the free (c) labeled CFS not involved in formation of said complex A" and/or the complex B" and (iii) the coexisting substances in the blood-derived sample.

(1) The Step of Introduction

The step of introduction is a step of introducing and arranging a plurality of solutions [a plurality of the solutions in any of [I-1] to [I-2] of the above non-competitive method, and a plurality of the solutions in any of [I-1] to [I-7] of the above competitive method] selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS to the inside of the capillary for ITP, so that the complex including the analyte and/or the complex including the analogue (the labeled analogue or the mobility-changing analogue) [the complex A in the above [II-1] and [II-2] of the above non-competitive method, the complex A'and the complex B' in the above [II-1] of the above competitive method, the complex B' in the above [II-2] of the above competitive method, the complex A' in the above [II-3] of the above competitive method, the complex A' and the complex B' in the above [II-4] and [II-5] of the above competitive method, the complex B" in the above [II-6] of the above competitive method, and the complex A" in the above [II-7] of the above competitive method] are formed by applying a voltage onto the both sides of said capillary, namely, in carrying out the step of concentration and separation to be described later by ITP, without mixing these solutions, in advance, at the outside the capillary for ITP.

Here, "so that the complex including the analyte and/or the complex including the analogue (the labeled analogue or the mobility-changing analogue) [the complex A in [II-1] and [II-2]of the above non-competitive method, the complex A' and the complex B' in [II-1] of the above competitive method, the complex B' in [II-2] of the above competitive method, the complex A'in [II-3] of the above competitive method, the complex A' and the complex B' in [II-4] and [II-5] of the above competitive method, the complex B" in [II-6] of the above competitive method, and the complex A" in [II-7] of the above competitive method] are formed, by applying a voltage onto the both sides of the capillary" means that in the case of carrying out electrophoresis by ITP, by arranging a solution containing a substance having higher electrophoretic mobility (faster electrophoretic mobility) at the upstream of a solution containing a substance having lower electrophoretic mobility (slower electrophoretic mobility), without by (not depending on) molecular diffusion, the complex including the analyte and/or the complex including the analogue (the labeled analogue or the mobility-changing analogue) [the complex A in the above [II-1] and [II-2] of the above non-competitive method, the complex A' and the complex B' in the above [II-1] of the above competitive method, the complex B' in the above [II-2] of the above competitive method, the complex A' in the above [II-3]of the above competitive method, the complex A' and the complex B' in the above [II-4] and [II-5] of the above competitive method, the complex B" in the above [II-6] of the above competitive method, and the complex A" in the above [II-7] of the above competitive method] is formed by ITP, by utilization of phenomenon that the substance having higher electrophoretic mobility overtakes the substance having lower electrophoretic mobility.

That is, the present invention is enough to form the complex of (1) the analyte or the analogue thereof, or the analyte or the analogue thereof and a certain labeled CFS or the mobility-changing CFS, and (2) at least one kind of labeled CFS and/or the mobility-changing CFS, at the inside of the capillary for ITP, by applying a voltage at the both sides of said capillary for ITP. In other words, the present invention encompasses not only the case where the complex of the analyte or the analogue thereof and all CFSs (the labeled CFS and the mobility-changing CFS) are formed only at the inside of said capillary, but also, for example, when two or more kinds of the CFSs (the labeled CFS and/or the mobility-changing CFS) are used, the case where after the complex (intermediate complex) of the analyte or the analogue thereof and a part of the CFS (the labeled CFS and/or the mobility-changing CFS) among two or more kinds of the CFSs (the labeled CFS and the mobility-changing CFS), is formed, in advance, at the outside of the capillary for ITP, or by a method other than ITP [at the outside of the capillary (complex forming method 1-1), at the inside of the capillary for mixing, without applying a voltage (complex forming method 1-2-1), or at the inside of the capillary for ITP, electrophoretically, by an electrophoresis method other than ITP (complex forming method 1-2-2)], said intermediate complex and the residual one or more kinds of the CFSs (the labeled CFS and the mobility-changing CFS) are contacted at the inside of the capillary for ITP, by applying a voltage at the both sides of said capillary for ITP, so as to form the complex of said intermediate complex, which were formed in advance, and the residual one or more kinds of the CFSs. In addition, for example, in the case of using the analogue (the labeled analogue or the mobility-changing analogue), the case is also encompassed where, after forming, in advance, either of the complex including the analogue [the complex of the labeled analogue or the mobility-changing CFS (the complex A'), the complex of the mobility-changing analogue and the labeled CFS (the complex A")] and the complex including the analyte [the complex of the analyte and the mobility-changing CFS (the complex B'), the complex of the analyte and the labeled CFS (the complex B")] at the outside of the capillary for ITP, or by a method other than ITP [at the place outside the capillary (a method for forming the complex 1-1), at the inside of the capillary for mixing without applying a voltage (a method for forming the complex 1-2-1), or at the inside of the capillary for ITP electrophoretically, by an electrophoresis method other than ITP (a method for forming the complex 1-2-2)], the residual complex is formed by contacting the complex formed and the analyte not contained in said complex or the analogue (the labeled analogue or the mobility-changing analogue), at the inside of the capillary for ITP by ITP, by applying a voltage at the both sides of said capillary for ITP.

Therefore, in the present invention, "without mixing the solutions, in advance" means that at least two kinds of the solutions selected from the solution containing the analyte, the solution containing the analogue (the labeled analogue or the mobility-changing analogue), the solution containing the analyte and the analogue, the solution containing at least one or kind of the CFS (the labeled CFS or the mobility-changing CFS), and the solution containing the analyte or the analogue and the CFS, which solutions relate to the objective reaction, [a plurality of the solutions in any of [I-1] to [I-2] of the above non-competitive method, and a plurality of the solutions in any of [I-1] to [I-7] of the above competitive method] are not mixed in advance, and should not mean that all of these solutions relating to the objective reaction are not mixed at all, in advance.

In the present invention, in the case of applying a voltage (in the case of carrying out ITP), direction in which the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs) move, is defined as the "downstream" side, and the opposite direction thereof is defined as the "upstream" side.

A arrangement order of a plurality of solutions [a plurality of the solutions in any of [I-1] to [I-2] of the above non-competitive method, and a plurality of the solutions in any of [I-1] to [I-7] of the above competitive method] selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, is not especially limited, as long as it is an order which is capable of forming the complex including the analyte and/or the complex including the analogue (the labeled analogue or the mobility-changing analogue) [the complex A in [II-1] and [II-2]of the above non-competitive method, the complex A' and the complex B' in [II-1] of the above competitive method, the complex B' in [II-2] of the above competitive method, the complex A'in [II-3] of the above competitive method, the complex A' and the complex B' in [II-4] and [II-5] of the above competitive method, the complex B'' in [II-6] of the above competitive method, and the complex A'' in [II-7] of the above competitive method]by applying a voltage onto both sides of the capillary for ITP to carry out ITP. It may be set, as appropriate, according to the methods described in, for example, WO2007/027495 and WO2007/121263.

In more specifically, in the case of the non-competitive method, it is preferable to set, for example, the following arrangement order:

[I-1]: in a direction from the downstream to the upstream, (the LB zone)/the solution (zone) containing one or more kinds of the labeled analogue/the solution (zone) containing the blood-derived sample including the analyte/the solution (zone) containing one or more kinds of the mobility-changing CFSs/(the TB zone).

[I-2]: in a direction from the downstream to the upstream, (the LB zone)/the solution (zone) containing the blood-derived sample including the analyte and one or more kinds of the labeled CFSs/the solution (zone) containing one or more kinds of the mobility-changing CFSs/(the TB zone).

In addition, in the case of the competitive method using the labeled analogue, it is preferable to set, for example, the following arrangement order:

[I-1]: in a direction from the downstream to the upstream, (the LB zone)/the solution (zone) containing the blood-derived sample including the analyte and the labeled CFSs/the solution (zone) containing one or more kinds of the mobility-changing CFSs/(the TB zone).

[I-2]: in a direction from the downstream to the upstream, (the LB zone)/the solution (zone) containing the blood-derived sample including the analyte/the solution (zone) containing the labeled analogue and one or more kinds of the mobility-changing CFSs/(the TB zone).

[I-3]: in a direction from the downstream to the upstream, (the LB zone)/the solution (zone) containing the labeled analogue/the solution (zone) containing the blood-derived sample including the analyte and one or more kinds of the mobility-changing CFSs/(the TB zone).

[I-4]: in a direction from the downstream to the upstream, (the LB zone)/the solution (zone) containing the blood-derived sample including the analyte/the solution (zone) containing the labeled analogue/the solution (zone) containing one or more kinds of the mobility-changing CFSs/(the TB zone).

[I-5]: in a direction from the downstream to the upstream, (the LB zone)/the solution (zone) containing the labeled analogue/the solution (zone) containing the blood-derived sample including the analyte/the solution (zone) containing one or more kinds of the mobility-changing CFSs/(the TB zone).

Further, in the case of the competitive method using the mobility-changing analogue, it is preferable to set, for example, the following arrangement order:

[I-6]: in a direction from the downstream to the upstream, (the LB zone)/(zone) of the blood-derived sample including the analyte (or the solution including the sample)/the solution (zone) containing one or more kinds of the labeled CFSs and the mobility-changing analogue/(the TB zone).

[I-7]: in a direction from the downstream to the upstream, (the LB zone)/the solution (zone) containing the blood-derived sample including the analyte and one or more kinds of the labeled CFSs/the solution (zone) containing the mobility-changing analogue/(the TB zone).

In this connection, it is needless to say that, the arrangement order at the inside of the above capillary for ITP is absolutely an order between the solution containing the analyte or the analogue thereof (the labeled analogue or the reaction improvement analogue) and the solution including one or more kinds of the CFSs (the labeled CFS and/or the reaction improvement CFS), and thus solutions other than said solutions may be arranged, at the further downstream side of said solution arranged at the most downstream side thereof, or at the further upstream side of said solution arranged at the most upstream side thereof.

In addition, a plurality of solutions [a plurality of the solutions in any of [I-1] to [I-2] of the above non-competitive method, and a plurality of the solutions in any of [I-1] to [I-7]of the above competitive method] selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, are not necessarily be adjacent, and for example, liquid such as water, a normal saline solution, various buffer solutions, organic solvents may be inserted among these solutions. In this connection, as such buffer solutions, any one not to disturb formation of the complex relevant to the present invention can be used, and there are included buffer solutions to be used usually in this field such as Tris buffer, Good's buffer, TE buffer, TAE buffer, TBE buffer, TBS buffer, a phosphate buffer, a borate buffer, etc.

In this connection, the solution containing the analyte or the analogue thereof (the labeled analogue or the reaction improvement analogue), and the solution including one or more kinds of the CFSs (the labeled CFS and/or the reaction improvement CFS) [a plurality of the solutions in any of [I-1]to [I-2] of the above non-competitive method, and a plurality of the solutions in any of [I-1] to [I-7] of the above competitive method], and if necessary said liquid, are formed and arranged as each separate zone at the inside of the capillary for ITP. In other words, between the solution containing the analyte or the analogue thereof (the labeled analogue or the reaction improvement analogue), and the solution including one or more kinds of the CFSs (the labeled CFS and/or the reaction improvement CFS) [between a plurality of the solutions in any of [I-1] to [I-2] of the above non-competitive method, and between a plurality of the solutions in any of [I-1] to [I-7]of the above competitive method], if necessary, between the solution containing the analyte or the analogue thereof (the labeled analogue or the reaction improvement analogue) and said liquid, or between the solution including one or more kinds of the CFSs and said liquid, liquid-liquid interface is formed and maintained at the timing when these solutions, and if necessary, said liquid are arranged.

In the step of introduction, a method for introducing a plurality of solutions [a plurality of the solutions in any of [I-1] to [I-2] of the above non-competitive method, and a plurality of the solutions in any of [I-1] to [I-7] of the above competitive method] selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, at the inside of the capillary for ITP, may be enough as long as the method is capable of forming the zones of these plurality of solutions separately at the inside of the capillary for ITP, so as to provide the above arrangement, in other words, the method is capable of forming liquid-liquid interface between the solution containing the analyte or the analogue thereof (the labeled analogue or the reaction improvement analogue), and the solution containing one or more kinds of the CFSs (the labeled CFS and/or the reaction improvement CFS) [between a plurality of the solutions in any of [I-1] to [I-2] of the above non-competitive method, and between a plurality of the solutions in any of [I-1] to [I-7]of the above competitive method], if necessary, between the solution containing the analyte or the analogue thereof (the labeled analogue or the reaction improvement analogue) and said liquid, or between the solution including one or more kinds of the CFSs and said liquid, and a method for introduction known itself can be used.

As such a method for introduction known itself, there are included a method for electrically introducing these solutions (and said liquid) to the inside of the capillary, by applying a voltage onto the capillary; a method for introducing these solutions (and said liquid) to the inside of the capillary, by pressurization and/or depressurization of the inside of the capillary; a method for introducing these solutions (and said liquid) to the inside of the capillary, by utilization of capillary phenomenon, etc.

In addition, as a method for introducing and arranging a plurality of solutions [a plurality of the solutions in any of [I-1] to [I-2] of the above non-competitive method, and a plurality of the solutions in any of [I-1] to [I-7] of the above competitive method], selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, at the inside of the capillary for ITP, a method for introduction and arrangement known itself can be used. As such a method for introduction and arrangement known itself, there are included, for example, (1) a method for firstly introducing one kind among a plurality of solutions [a plurality of the solutions in any of [I-1] to [I-2] of the above non-competitive method, and a plurality of the solutions in any of [I-1] to [I-7] of the above competitive method], selected from the solution containing the analyte, the solution containing the analogue thereof (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, from the end of the capillary to the inside of the capillary by the above introduction method, and then introducing one kind of residual solutions, from the end of the capillary to the inside of the capillary similarly by the above introduction method, and by repeating this to arrange all of the solutions at the inside of the capillary for ITP, (2) a method for firstly dropping one kind among a plurality of solutions [a plurality of the solutions in any of [I-1] to [I-2] of the above non-competitive method, and a plurality of the solutions in any of [I-1] to [I-7] of the above competitive method], selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, to the inside of the liquid reservoir (well), and introducing this to the inside of the capillary by the above introduction method, and then, after replacing the solution at the inside the liquid reservoir (well) with one kind of residual solutions, introducing this to the inside of the capillary similarly by the above introduction method, and by repeating this to arrange all of the solutions at the inside of the capillary for ITP and (3) a method for dropping separately one kind among a plurality of solutions [a plurality of the solutions in any of [I-1] to [I-2] of the above non-competitive method, and a plurality of the solutions in any of [I-1] to [I-7] of the above competitive method], selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, to each of a plurality of the liquid reservoirs (wells), and introducing these separately to the inside of the same capillary, by the above introduction method, to arrange all of the solutions at the inside of the capillary for ITP. In this connection, a method for introducing a plurality of solutions [a plurality of the solutions in any of [I-1] to [I-2] of the above non-competitive method, and a plurality of the solutions in any of [I-1] to [I-7] of the above competitive method], selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, to the inside of the capillary, and a method for introducing and arranging a plurality of solutions [a plurality of the solutions in any of [I-1] to [I-2]of the above non-competitive method, and a plurality of the solutions in any of [I-1] to [I-7] of the above competitive method], selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, to the inside of the capillary for ITP are not limited to the above methods.

(2) The Step of Concentration and Separation

The step of concentration and separation in the separation method 2 of the present invention is a step of separating the following labeling substance-containing complex (the complex A, the complex A' or the complex A" relevant to the present invention), the free labeling substance-containing molecule (the labeled CFS, the labeled analogue from the analyte-labeled CFS complex) not involved in formation of said labeling substance-containing complex, and the coexisting materials in the blood-derived sample, while concentrating the complex (the complex A, the complex A' or the complex A"" relevant to the present invention) including the labeling substance among the following complexes at the downstream side of the TB zone (in more specifically, at the downstream side of the trailing ion), by making contacted electrophoretically, said analyte and the CFS (the labeled CFS and/or the mobility-changing CFS), or by making contacted electrophoretically, said analyte, the analogue thereof (the labeled analogue or the mobility-changing analogue) and the CFS (the labeled CFS and/or the mobility-changing CFS), not by (not depending on) molecular diffusion, by applying a voltage onto both sides of the capillary for ITP arranged so as to be the TB zone/a plurality of solutions (zone)/the LB zone by the above introduction step, in the presence of the MES ion and/or the glutamate ion, namely, by carrying out ITP in the presence of the MES ion and/or the glutamate ion, to form the complex including the analyte and/or the complex including the analogue.

"before the solutions [a plurality of the solutions [a plurality of the solutions in any of [I-1] to [I-2] of the above non-competitive method, and a plurality of the solutions in any of [I-1] to [I-7] of the above competitive method] selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS] are uniformly mixed" means a state before all of each zone of (liquid-liquid surface) a plurality of the solutions [a plurality of the solutions in any of [I-1] to [I-2] of the above non-competitive method, and a plurality of the solutions in any of [I-1] to [I-7] of the above competitive method] selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, and if necessary said liquid, which were arranged at the inside of the capillary for ITP, by the step of introduction, is uniformly mixed by molecular diffusion.

In this connection, "interface" in the present invention means a boundary where a plurality of the solutions [a plurality of the solutions in any of [I-1] to [I-2] of the above non-competitive method, and a plurality of the solutions in any of [I-1] to [I-7] of the above competitive method] selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, are contacted, if necessary, a boundary where these solutions and liquid are contacted, and should not mean that, practically, said interface is not necessarily mixed at all by diffusion.

In addition, "to make contacted said analyte and the CFS (the labeled CFS and/or the mobility-changing CFS), or to make contacted said analyte, the analogue thereof (the labeled analogue or the mobility-changing analogue) and the CFS (the labeled CFS and/or the mobility-changing CFS)" means that contact between said analyte and the CFS (the labeled CFS and/or the mobility-changing CFS), or contact among said analyte, the analogue thereof (the labeled analogue or the mobility-changing analogue) and the CFS (the labeled CFS and/or the mobility-changing CFS) is generated, without to molecular diffusion (not depending on molecular diffusion) as described above, by utilization of the phenomenon that the substance having higher electrophoretic mobility (faster electrophoretic mobility) in the solution overtakes the substance having lower electrophoretic mobility (slower electrophoretic mobility), in the case of carrying out electrophoresis by ITP, by arranging a substance having higher electrophoretic mobility (faster electrophoretic mobility) at the downstream of a sample or a solution containing a substance having lower electrophoretic mobility (slower electrophoretic mobility), and by utilization of phenomenon that the substance having higher electrophoretic mobility (faster electrophoretic mobility) overtakes the substance having lower electrophoretic mobility (slower electrophoretic mobility) among said analyte, and the CFS (the labeled CFS and/or the mobility-changing CFS), by ITP; or the contact is generated by the phenomenon that the substance having higher electrophoretic mobility (faster electrophoretic mobility) overtakes the substance having lower electrophoretic mobility (slower electrophoretic mobility) among said analyte, the analogue thereof (the labeled analogue or the mobility-changing analogue) and one or more kinds of the CFS (the labeled CFS and/or the mobility-changing CFS). That is, in the step of concentration and separation, contact is attained, not by mixing by molecular diffusion (depending on molecular diffusion) caused by standing still a plurality of the solutions [a plurality of the solutions in any of [I-1] to [I-2] of the above non-competitive method, and a plurality of the solutions in any of [I-1] to [I-7] of the above competitive method] selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS, if necessary said liquid, which were arranged in the capillary for ITP, as well as not by mixing these solutions physically at the inside of the capillary, and further not by moving these solutions electrophoretically at the inside of the capillary for ITP, by electrophoresis other than ITP, but by moving the analyte and the CFS (the labeled CFS and/or the mobility-changing CFS) in the solution electrophoretically by ITP, or by moving the analyte, the analogue thereof (the labeled analogue or the mobility-changing analogue) and one or more kinds of the CFSs (the labeled CFS and/or the mobility-changing CFS) electrophoretically by ITP.

In the step of concentration and separation, "to concentrate the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A"including the mobility-changing analogue and one or more kinds of the labeled CFSs) by applying a voltage onto both sides of the capillary" means a state that the complex relevant to the present invention assemble band-likely (plug-likely), in applying a voltage onto both sides of the capillary for ITP (in carrying out ITP). In other words, it means that in applying a voltage onto both sides of the capillary for ITP (in carrying out ITP), said complex assemble to generate a portion having higher concentration of said complex than concentration of the analyte or the analogue (the labeled analogue or the mobility-changing analogue) corresponding to said complex in a zone arranged by the introduction step, namely, in applying a voltage onto both sides of the capillary for ITP (in carrying out ITP), the complex relevant to the present invention assemble to generate a portion having higher concentration of said complex than concentration of said complex than concentration of the analyte or the analogue (the labeled analogue or the mobility-changing analogue) corresponding to the complex relevant to the present invention, in a solution zone containing the analyte and/or the analogue (the labeled analogue or the mobility-changing analogue) corresponding to the complex relevant to the present invention arranged by the step of introduction (a solution zone containing the blood-derived sample including the analyte in [I-1], and a solution zone containing the blood-derived sample including the analyte and one or more kinds of the mobility-changing CFSs in [I-2], of the above non-competitive method; and a solution zone containing the blood-derived sample including the analyte and the labeled analogue in [I-1], a solution zone containing the labeled analogue and one or more kinds of the mobility-changing CFSs in [I-2], a solution zone containing the labeled analogue in [I-3], a solution zone containing the labeled analogue in [I-4], a solution zone containing the labeled analogue in [I-5], a solution zone containing the mobility-changing analogue and one or more kinds of the labeled CFSs in [I-6], a solution zone containing one or more kinds of the mobility-changing analogue in [I-7], of the above competitive method).

In this connection, as rate (degree) of concentration in the present invention, concentration of said complex of the assembled portion (band-likely) of said complex, in applying a voltage onto both side of the capillary for ITP (in carrying out ITP), is usually equal to or higher than 1.5 time, preferably equal to or higher than 5 times, more preferably equal to or higher than 10 times and further preferably equal to or higher than 25 times, as the lower limit; and the upper limit is not especially limited, however, usually equal to or lower than $10^5$ times, preferably equal to or lower than $10^4$ times, and more preferably equal to or lower than 2000 times, relative to concentration of the analyte or the analogue (the labeled analogue or the mobility-changing analogue) corresponding to the complex relevant to the present invention arranged by the step of introduction.

In the step of concentration and separation, the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analogue and one or more kinds of the labeled CFSs) obtained by the above formation of the complex is separated from the free labeling substance-containing molecule (the labeled CFS, the labeled analogue, and the analyte-labeled CFS complex) not involved in formation of said complex, and the coexisting materials in the blood-derived sample at the inside of the capillary for ITP while moving them electrically.

For example, in the case of the non-competitive method, it is enough to separate at least the complex A from the free labeled CFS, not involved in formation of said complex A, and the coexisting materials in the blood-derived sample, and it is not necessary to separate the mobility-changing CFS from said complex.

In addition, in the case of the competitive method using, for example, the labeled analogue, it is enough to separate at least the complex A' from the free labeled analogue not involved in formation of said complex A', and the coexisting materials in the blood-derived sample, and it is not necessary to separate the mobility-changing CFS or the complex B' (the complex of the analyte and the mobility-changing CFS) from said complex. In addition, in the case of the competitive method using the mobility-changing analogue, it is enough to separate at least the complex A" from the complex B" and the free labeled CFS not involved in formation of and said complex A" (and the complex B"), along with the coexisting materials in the blood-derived sample.

(2-1) The MES Ion and the Glutamate Ion

The MES ion and/or the glutamate ion to be used in the separation method 2 of the present invention are the same as the above-described separation method 1, and specific example and preferable embodiment thereof are as described above.

In the separation method 2 of the present invention, a method for making the MES ion and/or the glutamate ion existed in carrying out ITP is not especially limited, as long as it is capable of carrying out ITP, in the presence of the MES ion and/or the glutamate ion eventually.

As such a method, there is included, for example, a method for making the MES ion and/or the glutamate ion coexisted, in advance, in any one or more kinds of a plurality of solutions selected from the solution containing the analyte, the solution containing the analogue (the labeled analogue or the mobility-changing analogue), the solution containing the analyte and the analogue, the solution containing one or more kinds of the CFSs (the labeled CFS and/or the mobility-changing CFS), and the solution containing the analyte or the analogue and the CFS [any one or more kinds of (a) the solution containing the blood-derived sample including the analyte, (b) the solution containing one or more kinds of the mobility-changing CFSs and (c) the solution containing one or more kinds of the labeled CFSs; the solution containing two kinds among (a) to (c), and/or a solution containing the residual one kind; any one or more kinds of (a') the solution containing the labeled analogue, (b) the solution containing one or more kinds of the mobility-changing CFSs and (a) the solution containing the blood-derived sample including the analyte; the solution containing two kinds among the (a), (a') and (b), and/or the solution containing the residual one kind; or any one or more kinds of (a") the solution containing the mobility-changing analogue, (c) the solution containing one or more kinds of the labeled CFSs and (a) the solution containing the blood-derived sample including the analyte; the solution containing two kinds among the (a), (a") and (c), and/or the solution containing the residual one kind], which are introduced and arranged between the LB zone and the TB zone at the inside of the capillary for ITP, in the step of introduction, etc.

In more specifically, in the case of the non-competitive method, it is preferable that the MES ion and/or the glutamate ion are made coexisted, in advance, for example, in the solutions shown below:

[I-1]: Any one kind or all kinds of 1) the solution containing one or more kinds of the labeled CFSs, 2) the solution containing the blood-derived sample including the analyte and 3) the solution containing one or more kinds of the mobility-changing CFSs.

[I-2]: Any one kind or all kinds of 1) the solution containing the blood-derived sample including the analyte and one or more kinds of the labeled CFSs, and 2) the solution containing one or more kinds of the mobility-changing CFSs.

In addition, in the case of the competitive method using the labeled analogue, it is preferable that the MES ion and/or the glutamate ion are made coexisted, in advance, for example, in the solutions shown below:

[I-1] any one kind or all of 1) a solution containing the blood-derived sample including the analyte and the labeled analogue, and 2) a solution containing one or more kinds of the mobility-changing CFSs;

[I-2] any one kind or all of 1) a solution containing the blood-derived sample including the analyte, and 2) a solution containing the labeled analogue and one or more kinds of the mobility-changing CFSs;

[I-3] any one kind or all of 1) a solution containing the labeled analogue, and 2) a solution containing the blood-derived sample including the analyte and one or more kinds of the mobility-changing CFSs;

[I-4] any one kind or all of 1) a solution containing the blood-derived sample including the analyte, 2) a solution containing the labeled analogue, and 3) a solution containing one or more kinds of the mobility-changing CFSs;

[I-5] any one kind or all of 1) a solution containing the labeled analogue, 2) a solution containing the blood-derived sample including the analyte, and 3) a solution containing one or more kinds of the mobility-changing CFSs.

[I-1] is preferable among the above-described.

Further, in the case of the competitive method using the mobility-changing analogue, it is preferable that the MES ion and/or the glutamate ion are made coexisted, in advance, for example, in the solutions shown below:

[I-6] any one kind or all of 1) a solution containing the blood-derived sample including the analyte, and 2) a solution containing the mobility-changing analogue and one or more kinds of the labeled CFSs; and

[I-7] any one kind or all of 1) a solution containing the blood-derived sample including the analyte and one or more kinds of the labeled CFSs, and 2) a solution containing the mobility-changing analogue.

In this connection, the MES ion and/or the glutamate ion may be made coexisted in the LB and/or the TB, however, it is preferable that they are made coexisted in the solutions (for example, any one kind or all of a plurality of the solutions in any of [I-1] to [I-2] of the above non-competitive method, and any one kind or all of a plurality of the solutions in any of [I-1] to [I-7] of the above competitive method) which are introduced and arranged between the LB and the TB at the inside of the capillary for ITP.

Among these, it is particularly preferable that the MES ion and/or the glutamate ion are made coexisted in the solution containing the blood-derived sample including the analyte [for example, 2) the solution containing the blood-derived sample including the analyte in [I-1], and the solution containing 1) the blood-derived sample including the analyte and one or more kinds of the labeled CFSs in [I-2] of the non-competitive method; and 1) the solution containing the blood-derived sample including the analyte and the labeled analogue in [I-1], 1) the solution containing the blood-derived sample including the analyte in [I-2], 2) the solution containing the blood-derived sample including the analyte and one or more kinds of the mobility-changing CFSs in [I-3], 1) the solution containing the blood-derived sample including the analyte in [I-4], 2) the solution containing the blood-derived sample including the analyte in [I-5], 1) the solution containing the blood-derived sample including the analyte in [I-6], 1) the solution containing the blood-derived sample including the analyte and one or more kinds of the labeled CFSs in [I-7] of the competitive method].

Use amount of the MES ion is, as concentration in a solution containing the MES ion, usually equal to or higher than 0.005 mM, preferably equal to or higher than 0.05 mM, more preferably equal to or higher than 0.5 mM, and particularly preferably equal to or higher than 1 mM, as the lower limit; and as the upper limit, equal to or lower than 100 mM, preferably equal to or lower than 20 mM, and more preferably equal to or lower than 10 mM.

In addition, use amount of the glutamate ion is, as concentration in a solution containing the glutamate ion, usually equal to or higher than 0.005 mM, preferably equal to or higher than 0.05 mM, more preferably equal to or higher than 0.5 mM, and particularly preferably equal to or higher than 1 mM, as the lower limit; and as the upper limit, equal to or lower than 100 mM, preferably equal to or lower than 20 mM, and more preferably equal to or lower than 10 mM.

(2-2) LB and TB

The LB to be used in the separation method 2 of the present invention, the leading ion in the LB, the TB, and the trailing ion in the TB are the same as in the above separation method 1, and specific example, use concentration, pH and preferable embodiment of these are as described above.

In this connection, in the separation method 2, the LB is arranged at the further downstream side of the solution arranged at the most downstream side of the capillary, among the solution containing the analyte or the analogue thereof (the labeled analogue or the mobility-changing analogue), and the solution including one or more kinds of the CFSs (the labeled CFS and/or the mobility-changing CFS) [for example, a plurality of the solutions in any of [I-1] to [I-2] of the above non-competitive method, and a plurality of the solutions in any of [I-1] to [I-6]of the above competitive method]; and the TB is arranged at the further upstream side of the solution arranged at the most upstream side of the capillary, among the solution containing the analyte or the analogue thereof (the labeled analogue or the mobility-changing analogue), and the solution including one or more kinds of the CFSs (the labeled CFS and/or the mobility-changing CFS) [for example, a plurality of the solutions in any of [I-1] to [I-2] of the above non-competitive method, and a plurality of the solutions in any of [I-1] to [I-7]of the above competitive method].

In addition, as a method for introducing and arranging the LB and the TB to the inside of the capillary for ITP, an introduction method known itself can be used, as long as it is a method capable of making said solution existed (making it introduced and arranged) at the LB zone and the TB zone at the inside of the capillary.

As such a method for introduction known itself, there is included the method for introducing and arranging the solution containing the complex relevant to the present invention to the inside of the capillary, in the introduction step of the above-described separation method 1, etc.

(2-3) ITP Conditions (Applied Voltage, pH, Temperature and Time)

The step of concentration and separation in the separation method 2 of the present invention, similarly as in the separation method 1, is also enough to carry out ITP, in the presence of the MES ion and/or the glutamate ion, and any of ITP methods known themselves can be used [for example, Everaerts, F. M., Geurts, M. Mikkers, F. E. P., Verheggen, T. P. E. M J. Chromatagr. 1976, 119, 129-155; Mikkers, F. E. P., Everaerts, F. M., Peek, J. A. F. J. Chromatogr. 1979, 168, 293-315; Mikkers, F. E. P., Everaerts, F. M., Peek, J. A. F. J. Chromatogr. 1979, 168, 317-332; Hirokawa, T, Okamoto, H. Ikuta, N., and Gas, B., Analytical Sciences 2001, Vol. 17 Supplement i185; WO2007/027495; WO2007/121263 etc.].

In addition, other reagents, operation methods and other conditions etc. can also be selected, as appropriate, according to description of the above literature etc.

Applied voltage in the step of concentration and separation may be in a range where the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A"including the mobility-changing analog and one or more kinds of the labeled CFSs) are formed and the complex relevant to the present invention are sufficiently concentrated, and also, the complex relevant to the present invention can be separated from the free labeling substance-containing molecule (the labeled CFS, the labeled analogue, and the analyte-labeled CFS complex) not involved in formation of said complex, and the coexisting materials in the blood-derived sample; and it may be selected, as appropriate, from those to be used usually in this field. In more specifically, voltage is applied so that there is attained electric field intensity in a range of, as the lower limit, usually equal to or higher than 5 V/cm, preferably equal to or higher than 10 V/cm, more preferably equal to or higher than 50 V/cm, further preferably equal to or higher than 500 V/cm, and particularly preferably equal to or higher than 1000 V/cm, and as the upper limit, usually equal to or lower than 10000 V/cm, preferably equal to or lower than 5000 V/cm, and more preferably equal to or lower than 2000 V/cm.

In addition, other ITP conditions (for example, pH, temperature, time etc.) may be in a range not to disturb formation of the complex relevant to the present invention (the complex A including the analyte, one or more kinds of mobility-changing CFSs and one or more kinds of the labeled CFSs, the complex A'including the labeled analogue and one or more kinds of the mobility-changing CFSs, and the complex A" including the mobility-changing analog and one or more kinds of the labeled CFSs), concentration of said complex, and separation of the complex relevant to the present invention from the free labeling substance-containing molecule (the labeled CFS, the labeled analogue, and the analyte-labeled CFS complex) not involved in formation of said complex, and the coexisting materials in the blood-derived sample.

Specifically, the pH is, as the lower limit, usually equal to or higher than 2, preferably equal to or higher than 5, and as the upper limit, usually equal to or lower than 10, preferably equal to or higher than 9, and the temperature is, as the lower limit, usually equal to or higher than 0° C., preferably equal to or higher than 5° C., more preferably equal to or higher than 10° C., and as the upper limit, usually equal to or lower than 50° C., preferably equal to or higher than 40° C. and more preferably equal to or lower than 30° C.

The ITP time differs depending on association constant of the CFS to be used to the analyte or the analogue thereof, and the case of lower association constant requires relatively longer reaction time, while the case of higher association constant requires relatively shorter reaction time. In more specifically, for example, the lower limit is usually equal to or longer than 30 seconds, preferably equal to or longer than 1 minute, and more preferably equal to or longer than 90 seconds, and the upper limit is usually equal to or shorter than 1 hour, preferably equal to or shorter than 30 minutes, and more preferably equal to or shorter than 10 minutes and further preferably equal to or shorter than 5 minutes.

As described above, the step of concentration and separation in the separation method 2 of the present invention is one for separating the following labeling substance-containing complex (the complex relevant to the present invention) from the free labeling substance-containing molecule (the labeled CFS, the labeled analogue, and the analyte-labeled CFS complex) not involved in formation of said labeling substance-containing complex, and the coexisting materials in the blood-derived sample, while concentrating said complex containing the labeling substance relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs), by making contacted the analyte and the CFS (the labeled CFS and/or the mobility-changing CFS) in the solution while moving them electrophoretically by ITP; or by making contacted said analyte, the analogue thereof (the labeled analogue or the mobility-changing analogue) and the CFS (the labeled CFS and/or the mobility-changing CFS) while moving them electrophoretically by ITP, before uniformly mixing by molecular diffusion, the solutions containing said analyte or the analogue thereof (the labeled analogue or the mobility-changing analogue), and the solutions including one or more kinds of the CFSs (the labeled CFS and/or the mobility-changing CFS) [for example, a plurality of the solutions in any of [I-1] to [I-2] of the non-competitive method, and a plurality of the solutions in any of [I-1] to [I-7] of the competitive method], and if necessary, sid liquid, and further without mixing physically at the inside of the capillary for ITP, in other words, while maintaining these adjacent liquid-liquid interface, so as to form the complex including the analyte and/or the complex including the analogue (the labeled analogue or the mobility-changing analogue) [the complex A in [II-1] and [II-2] of the above non-competitive method, the complex A' and the complex B' in [II-1] of the above competitive method, the complex B' in [II-2] of the above competitive method, the complex A' in [II-3] of the above competitive method, the complex A' and the complex B' in [II-4]and [II-5] of the above competitive method, the complex B" in [II-6] of the above competitive method, and the complex A" in [II-7] of the above competitive method].

In the present invention, in view of capability of making operation simpler and more convenient, as well as making a structure of microfluidics devices having the capillary simpler, the separation method 2 is more preferable in the separation method 1 and the separation method 2.

2-3. The Capillary (Channel)

The capillary (channel) for ITP to be used in the present invention is any one to be used usually in this field, such as the capillary electrophoresis method, the capillary chip electrophoresis method, and not especially limited.

Materials of the capillary (channel) for ITP to be used in the present invention are any one to be used usually in this field, and not especially limited as long as they can eventually form the complex including the analyte and/or the complex including the analogue (the labeled analogue or the mobility-changing analogue) [the complex A in [II-1] and [II-2]of the above non-competitive method, the complex A' and the complex B' in [II-1] of the above competitive method, the complex B' in [II-2] of the above competitive method, the complex A' in [II-3] of the above competitive method, the complex A' and the complex B' in [II-4] and [II-5] of the above competitive method, the complex B" in [II-6] of the above competitive method, and the complex A" in [II-7] of the above competitive method], by making contacted the analyte and the CFS (the labeled CFS and/or the mobility-changing CFS) or by making contacted said analyte, the analogue (the labeled analogue or the mobility-changing analogue) and the CFS (the labeled CFS and/or the mobility-changing CFS). Specific examples of the materials of the capillary (channel) for ITP include, for example, silica-based compounds such as glass, quartz and silicon, for example, synthetic polymers such as a cyclic olefin copolymer (COC), a cyclic olefin polymer (COP), poly (methyl methacrylate), polymethylsiloxane, polyvinyl chloride, polyurethane, polystyrene, polysulfone, polycarbonate, polytetrafluoroethylene, etc. In addition, an inner diameter and a length of the capillary (channel) are not especially limited, as long as they are capable of concentrating the complex relevant to the present invention, and separating said complex from the free labeling substance-containing molecule (the labeled CFS, the labeled analogue, and the analyte-labeled CFS complex) not involved in formation of said complex, and the coexisting materials in the blood-derived sample, in the separation method 1 of the present invention; as well as capable of forming and concentrating the complex relevant to the present invention, and separating said complex from the free labeling substance-containing molecule (the labeled CFS, the labeled analogue, and the analyte-labeled CFS complex) not involved in formation of said complex, and the coexisting materials in the blood-derived sample, in the separation method 2 of the present invention. In more specifically, the inner diameter is usually 1 to 1000 µm, preferably 1 to 200 µm and more preferably 1 to 100 µm, and the length is usually 0.1 mm to 100 cm, preferably 0.1 mm to 20 cm and more preferably 0.1 mm to 10 cm.

In this connection, the capillary to be used in order to form the complex relevant to the present invention at the inside of the capillary before carrying out ITP, in the separation method 1 of the present invention, is also similar to the above capillary for ITP, and may be used, as appropriate, according to a method known itself.

Into the solutions to be introduced to the capillary for ITP [for example, various solutions (the solution containing any one or more kinds of the analyte, the analogue and CFS; the LB, the TB, liquid, etc.) to be introduced in the above separation method 1 or the separation method 2], fillers (polymers) may be contained; by which suppression of electroosmotic flow, or separation degree of the complex relevant to the present invention and other components, or shape of the electrophoresis peak is changed, and as a result, analysis precision or analysis time etc. can be varied.

The fillers are not especially limited as long as they are used usually in this field. Specific examples of the fillers (polymers) include, for example, polyethers such as polyethylene oxide (polyethylene glycol), polypropylene oxide; polyalkylene imines such as polyethylene imine; polyacrylic acid polymers such as polyacrylic acid, polyacrylate esters, and poly(methyl acrylate); polyamide-based polymers such as polyacrylamide, polymethacrylamide; poly(methacrylic acid)-based polymers such as polymethacrylic acid, polymethacrylate esters and poly(methyl methacrylate); polyvinyl-based polymers such as polyvinyl acetate, polyvinyl pyrrolidone and polyvinyl oxazolidone; water-soluble hydroxyl polymers such as pullulan, elsinan, xanthan, dextran and guar gum; water-soluble cellulosic compounds such as methyl cellulose, hydroxyethyl cellulose and hydroxypropyl cellulose; derivatives thereof, and copolymers having a plurality of kinds of monomer unites composing these polymers, etc. In this connection, these fillers may be used either as one kind or two or more kinds in combination.

These fillers (polymers) may be contained in any of the solutions introduced to the capillary for ITP [for example, various solutions (a solution containing any one or more kinds of the analyte, the analogue and CFS; the LB, the TB, liquid, etc.) introduced in the separating method 1 or the separating method 2], however, it is preferable to be contained in all of the solutions introduced to the capillary for ITP.

In addition, molecular weight of the fillers as described above is usually 500 Da to 6000 kDa, preferably 1 to 1000 kDa and more preferably 50 to 500 kDa.

Use concentration of the fillers as described above may be selected, as appropriate, from a range to be used usually in this field, and is usually 0.01 to 40% (w/v), preferably 0.01 to 20% (w/v), and more preferably 0.1 to 10% (w/v).

In this connection, viscosity of the solution when the above-described fillers are added thereto, is usually 1 to 1000 centipoises, preferably 1 to 200 centipoises, and more preferably 1 to 10 centipoises.

In addition, by using affinity substances having affinity to the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs), or the free labeling substance-containing molecules (the labeled CFS, the labeled analogue, the complex of the analyte and the labeled CFS) not involved in formation of said complex (the labeling substance-containing complex), separation degree of the complex relevant to the present invention and the free labeling substance-containing molecules can be changed, and analysis precision or analysis time etc. can be varied, as well.

Such affinity substances are those having such a weak binding force that complex formation of the complex relevant to the present invention or the complex of the free labeling substance-containing molecules and the affinity substance, and dissociation of the affinity substances from the complex formed are repeated, and are those, for example, whose association constant to the complex relevant to the present invention or the free labeling substance-containing molecule is, as the lower limit, usually equal to or higher than $10^{-2}$ M$^-$, preferably equal to or higher than $10^{-3}$ M$^-$, and more preferably equal to or higher than $10^{-4}$ M$^-$, and as the upper limit, usually equal to or lower than $10^{-8}$ M$^-$, preferably equal to or lower than $10^{-7}$ M$^-$, and more preferably equal to or lower than $10^{-6}$ M$^-$. Specifically, for example, lectin (for example, concanavalin A, lentil lectin, *phaseolus vulgaris* lectin, datura lectin, wheat germ lectin etc.); oligo nucleotide (for example, oligo DNA, oligo RNA etc.), etc. are included, and among these, lectin is preferable.

In using the affinity substances, it is enough to carry out the step of concentration and separation of the present invention, in the presence of the affinity substances.

As such a method, there are included a method for making the affinity substances coexisted, in advance, for example, in the solutions to be introduced to the capillary for ITP [for example, various solutions (the solution containing any one or more kinds of the analyte, the analogue and CFS; the LB, the TB, liquid, etc.) to be introduced in the above separation method 1 or the separation method 2]; a method for making the affinity substances bound to the fillers, in advance; or a method for making the affinity substances bound at the inner surface of the capillary for ITP, etc. In this connection, as a method for making the affinity substances bound at the fillers or the inner surface of the capillary for ITP, there are included methods known themselves, for example, described in JP-A-2005-24445, JP-A-2005-31070, JP-B-7-24768 etc.

Among the above methods, a method for making the affinity substances coexisted in the solution containing the analyte and/or the analogue or the LB, in advance, is preferable, and a method for making them coexisted only in the LB is more preferable.

In addition, use amount of the affinity substances cannot be said unconditionally depending on kinds or a use method of the affinity substances to be used, however, for example, in the case of making the affinity substances existed in a solution to be introduced in the capillary, usually, it is, as concentration in a solution containing the affinity substances, as the lower limit, equal to or higher than 0.01 mg/mL, preferably equal to or higher than 0.1 mg/mL, and more preferably equal to or higher than 1 mg/mL; and as the upper limit, equal to or lower than 20 mg/mL, preferably equal to or lower than 10 mg/mL, and more preferably equal to or lower than 5 mg/mL.

In particular, in the case of using lectin as the affinity substance, concentration of lectin is, as concentration in a solution before voltage is applied onto the capillary (for example, a solution containing two or more kinds of the complexes and the affinity substances, a buffer solution for electrophoresis etc.), as the lower limit, equal to or higher than 0.01 mg/mL, preferably equal to or higher than 0.1 mg/mL, and more preferably equal to or higher than 1 mg/mL; and as the upper limit, equal to or lower than 20 mg/mL, preferably equal to or lower than 10 mg/mL, and more preferably equal to or lower than 5 mg/mL.

2-4. Analyte, Blood-Derived Sample, Coexisting Materials, Analogue and the Solution Containing These (1) Analyte The analyte in the present invention is one capable of being present in the blood-derived sample, and specifically includes, for example, a nucleotide chain (an oligonucleotide chain and a polynucleotide chain, etc.); a chromosome; a peptide chain (C-peptide and angiotensin I, etc.), protein [procalcitonin, immunoglobulin A (IgA), immunoglobulin E (IgE), immunoglobulin G (IgG), immunoglobulin M (IgM), immunoglobulin D (IgD), $\beta_2$-microglobulin, albumin, decomposition product thereof, and serum protein such as ferritin, etc.]; enzyme [an amylase (pancreatic type, salivary gland type and X-type, etc.), an alkaline phosphatase (hepatic, osseous, placental and small intestinal, etc.), an acid phosphatase (PAP, etc.), a γ-glutamyl transferase (renal, pancreatic and hepatic, etc.), a lipase (pancreatic type and gastric type, etc.), a creatine kinase (CK-1, CK-2 and mCK, etc.), a lactate dehydrogenase (LDH1 to LDH5, etc.), a glutamate oxaloacetate transaminase (ASTm and ASTs, etc.), a glutamate-pyruvate transaminase (ALTm and ALTs, etc.), a choline esterase (ChE1 to ChE5, etc.), a leucine aminopeptidase (C-LAP, AA and CAP, etc.), renin, a protein kinase and a tyrosine kinase, etc.]; hormones (PTH, TSH, insulin, LH, FSH and prolactin, etc.); a receptor (receptor for estrogen and TSH, etc.); a ligand (estrogen and TSH, etc.); microorganism such as bacteria (tuberculosis bacteria, pneumococcal organisms, diphtheria organisms, meningococcus, gonococcus, *staphylococcus, streptococcus*, enteric bacteria, coliform bacillus and *Helicobacter pylori*, etc.), viruses (rubella virus, herpes virus, hepatitis virus, ATL virus, AIDS virus, influenza virus, adenovirus, enterovirus, poliovirus, EB virus, HAV, HBV, HCV, HIV and HTLV, etc.), fungus (*candida* and *Cryptococcus*, etc.), spirochete (leptospire, *Treponema pallidum*, etc.), chlamydia and mycoplasma; protein, a peptide or a carbohydrate antigen derived from said microorganisms; various allergen causative of bronchospasm, allergic rhinitis and atopic dermatitis, etc. (allergen derived from the house dust, mites such as *Dermatophagoides farinae* and *Dermatophagoides pteronyssinus*, etc., pollen from cedar, cypress, *Pasupalum thunbergii*, ragweed, timothy, sweet vernal grass and rye, etc., an animal such as a cat, a dog or a crab, etc., food such as rice and egg white, etc., fungus, insect, wood, drug or chemical substance, etc.); lipids (lipoprotein, etc.); protease (trypsin, plasmin and serine protease, etc.); protein antigen tumor marker (PSA, PGI and PGII, etc.); a carbohydrate antigen [AFP (L1 to L3, etc.), hCG (hCG family, etc.), transferrin, IgG, thyroglobulin, Decay-accelerating factor (DAF), carcinoembryonic antigen (CEA, NCA, NCA-2 and NFA, etc.), CA19-9, PIVKA-II, CA125, prostate-specific antigen, a carbohydrate antigen tumor marker having a particular carbohydrate (sugar) chain produced by cancer cell and an ABO carbohydrate antigen, etc.]; carbohydrate (sugar) chain [hyaluronic acid, β-glucan and carbohydrate (sugar) chain contained in the above-described carbohydrate antigen, etc.]; a carbohydrate (sugar) chain binding protein (hyaluronic acid binding protein and β-glucan binding protein, etc.); phospholipid (cardiolipin, etc.); lipopolysaccharide (endotoxin, etc.); chemical substances (for example, T3, T4, an endocrine-disturbing hormones such as tributyltin, nonyl phenol, 4-octyl phenol, di-n-butyl phthalate, dicyclohexyl phthalate, benzophenone, octachlorostyrene and di-2-ethylhexyl phthalate); various drugs to be administered and inoculated to a human body, and metabolites thereof; and antibodies thereto, etc.

Specifically, among the above-described, the method of the present invention is useful for analysis (quantitative determination) of glycoprotein having different carbohydrate (sugar) chain structure, a nucleotide chain (oligonucleotide chain and polynucleotide chain) and a peptide chain (including polypeptide), is especially useful for glycoprotein having different carbohydrate (sugar) chain structure. In this connection, as the carbohydrate (sugar) chain structure is known to be changed in a particular disease such as cancer, and reported its usefulness in the clinical laboratory (clinical chemistry), the glycoprotein having different carbohydrate (sugar) chain structure can be reassessed for its usefulness in the clinical laboratory (clinical chemistry) using the method of the present invention. In addition, the separation of a mutant type generated by minute mutation or substitution, etc. of a nucleotide chain (an oligonucleotide chain or a polynucleotide chain) or a peptide chain (including polypeptide), etc. from the wild type has been considered as an important analytical target in the field of molecular biology and molecular clinical laboratory (clinical chemistry), and therefore, by analyzing (determining quantity) these mutant type and/or wild type using the method of the present invention, the possibility of finding out some valuable factors and the like in the clinical laboratory (clinical chemistry) will be increased.

(2) The Blood-Derived Sample Including the Analyte

The above blood-derived sample including the analyte of the present invention includes, for example, whole blood, serum, plasma, and processed products reconstituted by dissolving them in water or a buffer to be used usually in this field such as Tris buffer, a phosphate buffer, Veronal buffer, a borate buffer, Good's buffer, etc. In this connection, the blood-derived sample relevant to the present invention encompasses one including the above analyte prepared by chemical synthesis.

(3) The Coexisting Materials

The coexisting materials in the present invention are those in the above blood-derived sample, and are those having similar characteristics as the labeling substance used in detection (for example, in the case of using a fluorescent substance as the labeling substance, property to emit fluorescence), and having the same degree of electrophoretic mobility as that of the objective complex relevant to the present invention (in other words, substances moving near to the moving time of said complex by ITP, and substances having a peak at the same vicinity as the peak of relevant complex in an electropherogram of ITP).

As such coexisting materials, for example, substances emitting fluorescence such as bilirubin, biliverdin, hemoglobin, vitamins, a metabolite thereof, and a complex of such materials and protein are included.

Among these, the separation method of the present invention is particularly effective in separation of bilirubin as the coexisting materials, metabolites of bilirubin, or the complex between bilirubin and protein, and the complex relevant to the present invention.

(4) The Analogue (the Labeled Analogue and the Mobility-Changing Analogue)

The analogue to be used in the present invention is a substance to which the CFS (the labeled CFS, the mobility-changing CFS), which binds to the analyte in the blood-derived sample of the target for analysis, is bindable, in other words, the alalogue is a substance having the same binding site as the binding site existing in the analyte in said sample to which the CFS (the labeled CFS, the mobility-changing CFS) is bindable.

Such a substance includes, for example, the same one as the analyte in the blood-derived sample, the target of the analysis; one wherein a part of a structure of the analyte in the blood-derived sample is modified, altered, denatured, removed, etc. (so-called the analogue); etc. Specific examples of the substance include, for example, recombinant protein introduced with partial mutation at the analyte in the blood-derived sample, a target of the analysis; peptide with partially modified peptide sequence of the analyte in the blood-derived sample, the target of the analysis; a nucleotide chain with partially modified nucleotide sequence of the analyte in the blood-derived sample, the target of the analysis; etc. In this connection, specific examples of the analyte in the blood-derived sample, the target of the analysis, are as described above.

In this connection, the labeled analogue and the mobility-changing analogue used in the present invention are ones wherein the labeling substance or the mobility-changing substance is bound to the above described substances, and specific examples and preferable embodiments of the labeling substance and the mobility-changing substance are as described later. In addition, a method for binding the labeling substance or the mobility-changing substance to the above-described substances may be in accordance with a similar method to a method for binding the mobility-changing substance and the CFS or a method for labeling the CFS by the labeling substance, to be described later.

Use amount of the analogue (the labeled analogue or the mobility-changing analogue) is not unconditionally described because of dependency on kinds of the analogue (the labeled analogue or the mobility-changing analogue) to be used, or kinds or use concentration of the CFS, a sensitivity required to measurement or dynamic range etc.

In more specifically, the analogue (the labeled analogue or the mobility-changing analogue) may be contained in the solution (for example, the solution containing the analyte and the analogue, the solution containing the analogue, the solution containing the analogue and the labeled CFS or the reaction improvement CFS), so that use amount of the analogue (the labeled analogue or the mobility-changing analogue) in the solution as described above is, as the lower limit, usually equal to or higher than 10 pM, preferably equal to or higher than 1 nM and more preferably equal to or higher than 100 nM; and as the upper limit, usually equal to or lower than 10 μM, preferably equal to or lower than 1 μM and more preferably equal to or lower than 500 nM.

(5) The Solution Containing the Analyte or the Analogue

"The solution containing the analyte or the analogue thereof" means the solution including the analyte (the blood-derived sample including the analyte) or the analogue (the labeled analogue or the mobility-changing analogue) relevant to the present invention, as described above.

As such a solution, the following (a) to (f) are included:

(a) The blood-derived sample itself including the analyte or the solution containing said sample

[for example, a solution containing the blood-derived sample including the analyte in the non-competitive method [I-1] of the separation method 2, a solution containing the blood-derived sample including the analyte in the competitive method [I-2] of the separation method 2, a solution containing the blood-derived sample including the analyte in the competitive method [I-4] of the separation method 2, a solution containing the blood-derived sample including the analyte in the competitive method [I-5] of the separation method 2, a solution containing the blood-derived sample including the analyte in the competitive method [I-6] of the separation method 2, etc.]

(b) The solution containing the blood-derived sample including the analyte and one or more kinds of the labeled CFSs and/or the mobility-changing CFSs (in other words, the solution including the complex of the analyte and one or more kinds of the labeled CFSs and/or the mobility-changing CFSs)

[for example, a solution including the complex A and the free labeled CFS not involved in formation of said complex A in the separation method 1, a solution containing the blood-derived sample including the analyte and one or more kinds of the labeled CFSs in the non-competitive method [I-2] of the separation method 2, a solution containing the blood-derived sample including the analyte and one or more kinds of the mobility-changing CFSs in the competitive method [I-3] of the separation method 2, a solution containing the blood-derived sample including the analyte and one or more kinds of the labeled CFSs in the competitive method [I-7] of the separation method 2, etc.]

(c) The solution containing the analogue (the labeled analogue, and the mobility-changing analogue)

[for example, a solution containing the labeled analogue in the competitive method [I-3] of the separation method 2, a solution containing the labeled analogue in the competitive method [I-4] of the separation method 2, a solution containing the mobility-changing analogue in the competitive method [I-7] of the separation method 2, etc.]

(d) The solution containing the blood-derived sample including the analyte and the analogue (the labeled analogue, and the mobility-changing analogue) (in other words, the solution including the analyte and the analogue)

[for example, a solution containing the blood-derived sample including the analyte and the labeled analogue in the competitive method [I-1] of the separation method 2]

(e) The solution containing the analogue (the labeled analogue, and the mobility-changing analogue) and one or more kinds of the labeled CFSs and/or the mobility-changing CFS (in other words, the solution containing the complex of the analogue and one or more kinds of the labeled CFSs and/or the mobility-changing CFS)

[for example, a solution containing the labeled analogue and one or more kinds of the mobility-changing CFSs in the competitive method [I-2] of the separation method 2, a solution containing the mobility-changing analogue and one or more kinds of the labeled CFSs in the competitive method [I-6] of the separation method 2, etc.]

(f) The solution including the blood-derived sample including the analyte, the analogue (the labeled analogue, and the mobility-changing analogue) and one or more kinds of the labeled CFSs and/or the mobility-changing CFS

[for example, a solution containing the complex A', the complex B', and the free labeled analogue not involved in formation of said complex A' (and B') in the separation method 1, a solution containing the complex A", the complex B", and the free labeled CFS not involved in formation of said complex A" (and B") in the separation method 1, etc.]

In addition, it goes without saying that various solutions to be used in order to form the complex relevant to the present invention at the inside or outside of the capillary before carrying out ITP, in the separation method 1 of the present invention, also correspond to the above solution containing the analyte or the analogue thereof.

In this connection, in the above solution (b) or (e), for example, in the present invention, there is also included a solution containing the complex (the intermediate complex) between a part of the CFSs among all of the labeled CFSs and/or the mobility-changing CFSs (a part of the whole CFSs) eventually binding with the analyte or the analogue thereof, and the analyte or the analogue thereof, in other words, there is also a solution containing the complex (the intermediate complex) between CFSs fewer than CFSs constructing the analyte to be formed eventually or the analogue thereof and the labeled CFS and/or the mobility-changing CFS, and the analyte or the analogue thereof.

That is, for example, when 2 kinds of CFSs are used, it is a solution containing a complex (an intermediate complex) between one kind of CFS and an analyte or an analogue thereof. And for example, when 3 kinds of CFSs are used, it is a solution containing a complex (an intermediate complex) between one kind of CFS and an analyte or an analogue thereof, and a solution containing a complex (an intermediate complex) between 2 kinds of CFSs and an analyte or an analogue thereof. (In this case, also when 4 or more kinds of CFSs are used, a way of thinking is the same as in theses cases.)

In this connection, the fillers (polymers) may be contained in any one kind of the above solutions, however, it is preferable to be contained in all of the solutions.

In the above description, (a) the blood-derived sample including the analyte is as described above. In addition, solutions (a) to (f) may be any one, as long as they do not disturb formation of the complex between the analyte and the labeled CFS and/or the mobility-changing CFS, and/or the complex between the analogue (the labeled analogue or the mobility-changing analogue) and the labeled CFS and/or the mobility-changing CFS, and not disturb ITP, and for example, water, the buffer solution (for example, the LB or the TB), etc. are included.

2-5. The CFS (the Labeled CFS, the Mobility-Changing CFS), the Mobility-Changing Substance, the Labeling Substance and the Solution Including These (1) CFS In the present invention, "the substance formable the complex with the analyte (Complex Forming Substance: CFS)" means a substance having property capable of forming the complex between the above analyte or the analogue thereof and the CFS, namely, the complex including the analyte or the analogue thereof and the CFS as constituents, by binding with the analyte or the analogue thereof as described above, or by binding with the analyte or the analogue thereof via other CFS.

Such a CFS includes the substance which binds to the analyte or the analogue thereof by a mutual interaction such as an "antigen"-"antibody" reaction, a "carbohydrate (sugar) chain"-"protein" reaction, a "carbohydrate (sugar) chain"-"lectin" reaction, an "enzyme"-"inhibitor" reaction, a "protein"-"peptide chain" reaction or a "chromosome or nucleotide chain"-"nucleotide chain" reaction, "nucleotide chain"-"protein" reaction etc. When one of the substances in the above-mentioned pairs is the analyte or the analogue thereof, the other is the CFS. For example, when the analyte or the analogue thereof is an "antigen", the CFS is an "antibody", and when the analyte or the analogue thereof is an "antibody", the CFS is an "antigen" (the same applied to the above other pairs).

Specifically, such a substance includes, for example, a nucleotide chain (an oligonucleotide chain and a polynucleotide chain, etc.); a chromosome; a peptide chain (C-peptide and angiotensin I, etc.), protein [procalcitonin, immunoglobulin A (IgA), immunoglobulin E (IgE), immunoglobulin G (IgG), immunoglobulin M (IgM), immunoglobulin D (IgD), $\beta_2$-microglobulin, albumin, a decomposition product thereof, and serum protein such as ferritin, etc.]; an enzyme [an amylase (pancreatic type, salivary gland type and X-type, etc.), an alkaline phosphatase (hepatic, osseous, placental and small intestinal, etc.), an acid phosphatase (PAP, etc.), a γ-glutamyl transferase (renal, pancreatic and hepatic, etc.), a lipase (pancreatic type and gastric type, etc.), creatine kinase (CK-I, CK-2andmCK, etc.), lactate dehydrogenase (LDH1 to LDH5, etc.), glutamate oxaloacetate transaminase (ASTm and ASTs, etc.), glutamate-pyruvate transaminase (ALTm and ALTs, etc.), choline esterase (ChE1 to ChE5, etc.), leucine aminopeptidase (C-LAP, AA and CAP, etc.), renin, protein kinase and tyrosine kinase, etc.]; hormones (PTH, TSH, insulin, LH, FSH and prolactin, etc.); a receptor (receptor for estrogen and TSH, etc.); a ligand (estrogen and TSH, etc.); an microorganism such as bacteria (tuberculosis bacteria, pneumococcal organisms, diphtheria organisms, meningococcus, gonococcus, *staphylococcus, streptococcus*, enteric bacteria, coliform *bacillus* and *Helicobacter pylori*, etc.), viruses (rubella virus, herpesvirus, hepatitis virus, ATL virusaidS virus, influenza virus, adenovirus, enterovirus, poliovirus, EB virus, HAV, HBV, HCV, HIV and HTLV, etc.), fungus (*Candida* and *Cryptococcus*, etc.), spirochete (leptospire, *Treponema pallidum*, etc.), chlamydia and mycoplasma; protein, a peptide or a carbohydrate antigen derived from said microorganisms; various allergen causatives of bronchospasm, allergic rhinitis and atopic dermatitis, etc. (allergen derived from house dust, mites such as *Dermatophagoides farinae* and *Dermatophagoides pteronyssinus*, etc., pollen from cedar, cypress, *Pasupalum thunbergii*, ragweed, timothy, sweet vernal grass and rye, etc., an animal such as a cat, a dog or a crab, etc., foods such as rice and egg white, etc., fungus, insects, wood, drugs or chemical substances, etc.); lipids (lipoprotein, etc.); protease (trypsin, plasmin and serine protease, etc.); an antigen of tumor marker protein (a protein antigen of a tumor marker) (PSA, PGI and PGII, etc.); a carbohydrate antigen [AFP (L1 to L3, etc.), hCG (hCG family, etc.), transferrin, IgG, thyroglobulin, Decay-accelerating factor (DAF), a carcinoembryonic antigen (CEA, NCA, NCA-2 and NFA, etc.), CA19-9, PIVKA-II, CA125, a prostate-specific antigen, a carbohydrate antigen tumor marker having a particular carbohydrate (sugar) chain prepared by a cancer cell and an ABO carbohydrate antigen, etc.]; a carbohydrate (sugar) chain [hyaluronic acid, β-glucan and a carbohydrate (sugar) chain contained in the above-described carbohydrate antigen, etc.]; a carbohydrate (sugar) chain binding protein (hyaluronic acid binding protein and β-glucan binding protein, etc.); phospholipid (cardiolipin, etc.); lipopolysaccharide (endotoxin, etc.); chemical substances (T3, T4, TSH, endocrine-disturbing chemicals such as tributyltin, nonyl phenol, 4-octyl phenol, di-n-butyl phthalate, dicyclohexyl phthalate, benzophenone, octachlorostyrene and di-2-ethylhexyl phthalate, etc.); various drugs to be administered and inoculated to a human body, and metabolites thereof; aptamar; nuclear acidic binding substances, and antibodies thereto, etc. In this connection, the antibody used in the present invention encompasses a decomposition product such as Fab and F(ab')$_2$ fragments, etc. prepared by degradation with a proteolytic enzyme (proteinase, etc.) such as papain or pepsin or by chemical degradation.

The CFS described above may be used alone or in combination with two or more kinds.

In this connection, when two or more kinds of the CFSs are used in combination (together), the binding site of each CFS is not especially limited, as long as two or more kinds of the CFSs can form the complex with the analyte or the analogue thereof. The binding sites to be bound by such CFSs include, for example, the case when all of binding sites to be bound by two or more of the CFSs are present on the analyte or the analogue thereof [binding form (1)]; the case where the binding site to be bound by at least one kind of CFS (for example, the CFS A) among two or more of the CFSs is present only on the analyte or the analogue thereof, and the binding site to be bound by another at least one kind of CFS (for example, complex binding substance B) is present on a site newly generated by the formation of the complex between the analyte or the analogue thereof and the CFS A [binding form (2)]; and the case where the binding site to be bound by at least one kind of CFS (for example, the CFS A) among two or more of the CFSs is present only on the analyte or the analogue thereof, and the binding site to be bound by another at least one kind of CFS (for example, the CFS B) is present only on the CFS A [binding form (3)]. Among these, it is preferable that the binding sites to be bound by each two or more of the CFSs are different. In this connection, in binding form (2), the substance having property to specifically bind to a newly generated site (the CFS) includes, for example, an antibody, a peptide chain and a nucleotide chain, etc., which can recognize the complex between the analyte or the analogue thereof and the CFS, and capable of binding thereto are included.

As a CFS as described above, one which binds with the analyte or the analogue thereof by an "antigen"-"antibody" reaction or a "carbohydrate (sugar) chain"-"protein" reaction is preferable. Specifically, the antibody to the analyte or the analogue thereof, or the antigen bound with the analyte or the analogue thereof, or protein binding to the analyte or the analogue thereof is preferable; and the antibody to the analyte or the analogue thereof, or protein binding to the analyte or the analogue thereof is more preferable.

A CFS as described above may be bound with the labeling substance or a substance capable of changing electrophoretic mobility (hereinafter, abbreviated as the mobility-changing substance) of the analyte and may result in (1) the CFS having property capable of forming the complex with the analyte or the analogue thereof and capable of changing electrophoretic mobility of the analyte or the analogue thereof (hereinafter, abbreviated as the mobility-changing CFS, and (2) the CFS having property capable of forming the complex with the analyte or the analogue thereof and labeled with the labeling substance (the labeled CFS).

By using the CFS (the mobility-changing CFS) bound with the mobility-changing substance, electrophoretic mobility of the CFS can be changed, and arrangement order of a solution containing the analyte or the analogue thereof (the labeled analogue or the mobility-changing analogue) and solutions including one or more kinds of the labeled CFSs and/or the mobility-changing CFSs in the step of introduction, can be controlled arbitrarily, and efficiency in concentration of the complex relevant to the present invention and formation reaction of said complex can be enhanced.

In addition, by using the CFS (the labeled CFS) bound with the labeling substance, the analyte in the blood-derived sample can be measured (detected).

(2) The Mobility-Changing CFS and the Mobility-Changing Substance

The mobility-changing CFS is one having property capable of forming the complex with the analyte or the analogue thereof, and capable of changing electrophoretic mobility of the analyte or the analogue thereof, in other words, one having property capable of generating difference in behavior (electrophoretic mobility) of said analyte or analogue thereof corresponding to electrophoresis operation by forming the complex with the analyte or the analogue thereof, and one capable of making electrophoretic mobility of the complex between the analyte or the analogue thereof and the mobility-changing CFS (or the complex between the analyte or the analogue thereof and the labeled CFS) higher or lower than electrophoretic mobility (faster or slower than electrophoretic mobility) of the analyte or the analogue thereof itself (the analyte or the analogue thereof not bound with the mobility-changing CFS).

As such a mobility-changing CFS, the above-described CFSs bound with the following mobility-changing substances are general: For example, an inorganic metal oxide such as silica and alumina, etc.; a metal such as gold, titanium, iron and nickel, etc.; an inorganic metal oxide introduced with a functional group by an operation such as silane coupling treatment, etc.; organisms such as various microorganisms and eukaryote cells, etc.; polysaccharide such as agarose, cellulose and insoluble dextran, etc.; synthetic polymer compounds such as polystyrene latex, a styrene-butadiene copolymer, a styrene-methacrylic acid copolymer, an acrolein-ethyleneglycol dimethacrylate copolymer, styrene-styrenesulfonic acid latex, polyacrylamide, poly(glycidyl methacrylate), polyacrolein-coated particles, crosslinked polyacrylonitrile, acrylic acid or acrylate ester-based polymers, an acrylonitrile-butadiene copolymer, a vinyl chloride-acrylate ester copolymer and a poly vinyl acetate-acrylate copolymer, etc.; biomolecules such as erythrocyte, sugar, nucleic acid (polynucleotide such as RNA, DNA), protein, polypeptide and polyamino acid (polyglutamic acid, polyaspartic acid, polylysine, etc.); lipids; etc. However, for example, the mobility-changing substance may be bound to the analyte or the analogue thereof by a chemical binding method such as a method for introducing a functional group at the surface of the mobility-changing substance and subsequently binding to the analyte or the analogue thereof via this functional group; a method for binding the mobility-changing substance and the analyte or the analogue thereof via a linker; etc. In this connection, in the above description, the mobility-changing substance is one having property capable of providing property, as the mobility-changing CFS as described above, to said CFS, by binding to the CFS. That is, the mobility-changing substance is one having property capable of changing electrophoretic mobility of the analyte or the analogue thereof, in other words, one having property capable of generating difference in behavior (electrophoretic mobility) of said analyte or analogue thereof corresponding to electrophoresis operation, via the CFS, by forming the complex between the analyte or the analogue thereof and the CFS (or the complex among the analyte or the analogue thereof, the mobility-changing CFS and the labeled CFS), and thus is capable of making electrophoretic mobility of the complex between the analyte or the analogue thereof and the mobility-changing CFS higher or lower than electrophoretic mobility (faster or slower than electrophoretic mobility) of the analyte or the analogue thereof itself or the complex between the analyte or analogue thereof not bound with the mobility-changing CFS and the CFS.

As the mobility-changing substance, a nucleic acid chain (a nucleotide chain), protein, polypeptide or polyamino acid is preferable, and a nucleic acid chain (a nucleotide chain) or polyamino acid is more preferable. Among these, a nucleic acid is preferable, DNA is more preferable. In addition, in particular, as DNA, double-stranded DNA is preferable.

Therefore, as the mobility-changing CFS, the above CFS bound with the above preferable mobility-changing substance is preferable, and an antibody, which is the CFS, bound with the above preferable mobility-changing substance is more preferable. Among these, an antibody, which is the CFS, bound with double-stranded DNA is particularly preferable.

In addition, length of a nucleic acid chain used is, for example, usually 50 by to 2000 bp, preferably 100 by to 1000 bp, more preferably 120 by to 700 bp, and particularly preferably 150 by to 500 bp. In this connection, the too short nucleic acid chain decreases charge of the nucleic acid chain and makes difficult to change electrophoretic mobility of the analyte or the analogue; on the contrary, the too long nucleic acid chain increases molecular weight and decreases mobility.

In this connection, the mobility-changing CFS (the mobility-changing substance) is used to control electrophoretic mobility of the complex relevant to the present invention, to obtain a sharply separated peak of the complex relevant to the present invention (to sharpen the separated peak) by using this, etc., and as a result, there may be the case where electrophoretic mobility of the complex relevant to the present invention becomes nearly the same degree as that of the coexisting materials (in particular, bilirubin, a metabolite thereof, or a complex of bilirubin and protein etc.) in the blood-derived sample [electrophoretic mobility of the complex relevant to the present invention moves to the vicinity of moving time of the coexisting materials (in particular, bilirubin, a metabolite thereof, or a complex of bilirubin and protein etc.) by ITP; separated peak of the complex relevant to the present invention appears at the vicinity of the peak of the coexisting materials (in particular, bilirubin) in an electropherogram of ITP; or both peaks overlap].

Therefore, the separation method of the present invention is particularly useful in such a case. In other words, the separation method of the present invention is particularly useful in the case of using one, as the mobility-changing CFS (the mobility-changing substance), which changes electrophoretic mobility of the complex relevant to the present invention to the vicinity of electrophoretic mobility of the coexisting materials (in particular, bilirubin, a metabolite thereof, or a complex of bilirubin and protein etc.) in the blood-derived sample.

In particular, in the case where the mobility-changing substance is the nucleic acid chain, in the case of using the nucleic acid chain with a length of usually 50 by to 2000 bp, preferably 100 by to 1000 bp, more preferably 120 by to 700 bp, and particularly preferably 150 by to 500 bp, the separation method of the present invention is particularly effective, because possibility is high that electrophoretic mobility of the complex relevant to the present invention becomes the same degree as that of the coexisting materials (in particular, bilirubin, a metabolite thereof, or a complex of bilirubin and protein etc.) in the blood-derived sample [electrophoretic mobility of the complex relevant to the present invention moves to the vicinity of moving time of the coexisting materials (in particular, bilirubin, a metabolite thereof, or a complex of bilirubin and protein etc.) by ITP; separated peak of the complex relevant to the present invention appears at the vicinity of the peak of the coexisting materials (in particular, bilirubin, a metabolite thereof, or a complex of bilirubin and protein etc.) in an electropherogram by ITP; or both peaks overlap].

In this connection, the nucleic acid chain in the present invention has a purine base or a pyrimidine base, and pentose as a saccharide moiety and a nucleotide residue including phosphoric acid as fundamental units, and each nucleotide is one forming a polynucleotide chain (for example, RNA having ribose as the saccharide moiety and/or DNA having deoxyribose as the saccharide moiety) by binding with carbon atoms at 3' or 5' site in the saccharide moiety via phosphoric acid.

The nucleic acid chain to be used in the present invention can be prepared, for example, by using a method known itself, such as a chemical synthesis method; a method for extracting and purifying from cells etc. derived from microorganisms, insects, animals and plants; a method for extracting and purifying vector proliferated by cell cultivation after incubating the above cells etc., wherein a vector gene such as suitable plasmid, phage, and cosmid are introduced; a method for utilizing gene amplification technology such as PCR (Molecular Cloning, A Laboratory Manual, $2^{nd}$ Ed., J. Sambroock, E. F. Fritsch, T. Maniatis, Cold Spring Harbor Laboratory Press; Handbook of Fluorescent Probe and Research Chemicals, $7^{th}$ Ed., Chapter 8, Molecular Probe Inc.; WO2002/082083). In addition, the nucleic acid chain thus obtained may be prepared to desired length by purification, as appropriate, after chemical decomposition or decomposition by a nucleic acid chain cleavage enzyme etc., such as a restriction enzyme.

In addition, such a nucleic acid chain can be prepared as well, by using an arbitrary species of modified nucleotide, which has been known to enhance stability of nucleotide to various nucleaze activities (for example, a phosphorothioate analog of nucleotide; nucleotide including a methylene group in a rebose ring, instead of oxygen; or nucleotide wherein 2'-deoxysaccharide substituent is substituted with 2'-fluoro, 2'-O-methyl, 2'-O-alkoxyl and 2'-O-allyl modification can be used. Such a modification is described in, for example, Nucleic Acids Res., 1997, 25, 4429-4443, Susan M Freier, et al.).

In order to make binding of the mobility-changing substance to the CFS, namely, in order to prepare the mobility-changing CFS, any common method to be used in this field may be applied, for example, a known labeling method itself generally performed in known EIA, RIA, FIA methods or a hybridization method themselves (for example, Ikagaku Jikken Koza (Experimental Manual in Medical Chemistry), vol. 8, edited by Yuichi Yamamura, $1^{st}$ Ed., Nakayama Shoten Co., Ltd., 1971; Zusetu (Illustrative Description) Fluorescent Antibodies, Akira Kawao, $1^{st}$ Ed., Softscience Co., Ltd., 1983; Enzyme Immunoassay, Eiji Ishikawa, Tadashi Kawai, Kiyoshi Miyai, $3^{rd}$ Ed., Igaku-Shoin Ltd., 1987; Molecular Cloning, A Laboratory Manual, $2^{nd}$ Ed., J. Sambroock, E. F. Fritsch, T. Maniatis, Cold Spring Harbor Laboratory Press; Handbook of Fluorescent Probe and Research Chemicals, $7^{th}$ Ed., Chapter 8, Molecular Probe Inc.; WO 2002/082083); or a common method utilizing a reaction between avidin (or streptoavidin) and biotin.

In addition, when a labeled CFS and the mobility-changing CFS are used in combination (are used parallely) as a CFS, and as long as a complex among 3 components of an analyte or an analogue thereof, a labeled CFS and the mobility-changing CFS, is formed, binding forms of these 3 components or binding sites of a labeled CFS and the mobility-changing CFS are not especially limited. Such binding forms include, for example, (1) so-called a sandwich complex wherein an analyte or an analogue thereof is sandwiched by a labeled CFS and the mobility-changing CFS, (2) a complex wherein the mobility-changing CFS or a labeled CFS is further bound at a binding site with an analyte or an analogue thereof and a labeled CFS or the mobility-changing CFS and (3) a complex wherein the mobility-changing CFS or a labeled CFS is further bound at a labeled CFS or the mobility-changing CFS bound with an analyte or an analogue thereof, and the like. In addition, said binding moieties include, for example, (1) the case when all of the binding sites of a labeled CFS and the mobility-changing CFS are present only on an analyte or an analogue thereof [binding form (1)], (2) the case when either of the binding sites of a labeled CFS or the mobility-changing CFS is present only on an analyte and an analogue thereof, and the other binding site is present at a new site generated by formation of a complex between an analyte and either of said labeled CFS and reaction improvement CFS [binding form (2)], (3) either of binding sites of a labeled CFS and the mobility-changing CFS is present only on an analyte or an analogue thereof, while the other binding site is present at only either of said labeled CFS and reaction improvement CFS [binding form (3)] and (4) the case of combinations thereof. Among those, a binding site of a labeled CFS, and a binding site of the mobility-changing CFS is preferably a different one. In this connection, in the above description (2), as one having property to specifically bind at a newly generated site (a labeled CFS and/or the mobility-changing CFS), for example, an antibody, a peptide chain, a nucleotide chain, and the like, which enable to recognize a complex between an analyte or an analogue thereof and a labeled CFS and/or the mobility-changing CFS, and bindable thereto are included.

(3) The Labeled CFS and the Labeling Substance

By using the labeled CFS labeled with the detectable labeling substance, it is possible to measure (detect) the analyte in the blood-derived sample.

As the labeling substance to be used in the present invention, it may be any one used in this field such as an enzyme immunoassay (EIA), a radio immunoassay (RIA), a fluorescent immunoassay (FIA), a hybridization method, etc., may be adopted. Such a labeling substance includes, for example, an enzymes such as alkaline phosphatase (ALP), β-galactosidase (β-Gal), peroxidase (POD), microperoxidase, glucose oxidase (GOD), glucose-6-phophate dehydrogenase (G6PDH), malate dehydrogenase and luciferase, etc.; dyes such as Coomassie brilliant blue R250, and methyl orange, etc.; HiLyte type dyes such as HiLyte Fluor 488, HiLyte Fluor 555, HiLyte Fluor 647, HiLyte Fluor 680 and HiLyte Fluor 750, etc. (all of them are trade names of HiLyte Bioscience, Inc.); Alexa type dyes such as Alexa Fluor Dye 350, Alexa Fluor Dye 430, Alexa Fluor Dye 488, Alexa Fluor Dye 532, Alexa Fluor Dye 546, Alexa Fluor Dye 555, Alexa Fluor Dye 568, Alexa Fluor Dye 594, Alexa Fluor Dye 633, Alexa Fluor Dye 647, Alexa Fluor Dye 660, Alexa Fluor Dye 680, Alexa Fluor Dye 700 and Alexa Fluor Dye 750, etc. (all of them are trade names of Molecular Probes, Inc.); CyDye type dyes such as Cy3, Cy3.5, Cy5, Cy5.5 and Cy7, etc. (all of them are trade names of Amersham Biosciences, Inc.); fluorescent materials such as fluorescein, rhodamine, dansyl, fluorescamine, coumarin, naphthylamine, or derivatives thereof; rare-earth fluorescent dyes [combinations of a rare earth metal such as samarium (Sm), europium (Eu), terbium (Tb) or dysprosium (Dy) and a chelate compound such as 4,4'-bis (1",1",1",2",2",3",3"-heptafluoro-4",6"-hexanedione-6"-yl) chlorosulfo-O-terphenyl (BHHCT), 4,7-bis (chlorosulfonyl)-1,10-phenanthoroline-2,9-dicarboxy lie acid (BCPDA), β-naphthyltrifluoroacetic acid (β-NTA), etc.], intercalator dyes [for example, acridine dyes such as acridine orange, etc.; ethidium compounds such as ethidium bromide, ethidium homodimer-1 (EthD-1), ethidium homodimer-2 (EthD-2), ethidiumbromidemonoazide (EMA) and dihydroethidium, etc.; iodine compounds such as propidium iodide, and hexidium iodide, etc.; 7-aminoactinomycin D (7-AAD); cyanine dimmer-type dyes such as POPO-I, BOBO-I, YOYO-I, TOTO-I, JOJO-I, POPO-3, LOLO-I, BOBO-3, YOYO-3, and TOTO-3, etc. (all of them are trade names of Molecular Probes, Inc.); SYTOX-type dyes such as SYBR Gold, SYBR Green I and SYBR Green II, SYTOX Green, SYTOX Blue, and SYTOX Orange, etc. (all of them are trade names of Molecular Probes, Inc.), etc.], one bound to a minor group of DNA double helix [for example, 4',6-diamidino-2-phenylindole(DAPI: trade name of Molecular Probes, Inc.), pentahydrate(bis-benzimido) (Hoechst 33258: trade name of Molecular Probes, Inc.), and trihydrochloride (Hoechst 33342: trade name of Molecular Probes, Inc.), etc.]; benzimido-type dyes (Hoechst 34580: trade name of Molecular Probes, Inc.), etc.], one specifically bound to the sequence of adenine-thymine (A-T) [for example, acridine dyes such as 9-amino-β-chloro-2-methoxyacridine (ACMA), and bis (β-chloro-2-methoxy-9-acridinyl)spermine (acridine homodimer), etc., hydroxystilbamidine, etc.]; luminescent materials such as luciferin, isoluminal, luminal, and bis(2,4, β-trifluorophenyl) oxalate, etc.; materials having absortion in a ultra-violet region such as phenol, naphthol, anthracene, or derivatives thereof; substances having property as spin labeling agents represented by compounds having an oxyl group such as 4-amino-2,2,6-β-tetramethylpiperidine-1-oxyl, 3-amino-2,2,5,5-tetramethylpyrrolidine-1-oxyl, and 2,6-di-t-butyl-α-(3,5-di-t-butyl-4-oxo-2,5-cyclohexadine-1-ylidene)-p-tolyloxyl; etc.

Labeling the CFS with the labeling substance may be carried out according to a method similar to a method for labeling the CFS with the labeling substance as described above, or a common method described in WO 2002/082083.

(4) The Solution Including the CFS (the Labeled CFS and/or the Mobility-Changing CFS)

Such a solution includes, for example, the solution containing one or more kinds of the mobility-changing CFSs in the non-competitive method [I-1] of the separation method 2, the solution containing one or more kinds of the mobility-changing CFSs in the non-competitive method [I-2] of the separation method 2; and the solution containing one or more kinds of the mobility-changing CFSs in the competitive method [I-1] of the separation method 2, the solution containing one or more kinds of the mobility-changing CFSs in the competitive method [I-4] of the separation method 2, the solution containing one or more kinds of the mobility-changing CFSs in the competitive method [I-5] of the separation method 2, etc.

The solution containing the above CFS (the labeled CFS and/or the mobility-changing CFS) may be one not to disturb formation of the complex between the analyte and the labeled CFS and/or the mobility-changing CFS, and/or the complex among the analogue (the labeled analogue or the mobility-changing analogue) and the labeled CFS and/or the mobility-changing CFS, and may be one not to disturb ITP, and includes, for example, water and a buffer solution (for example, the LB or the TB) etc.

Concentration of the CFS (the labeled CFS and/or the mobility-changing CFS) to be contained in the above solutions (or (b), (e) and (f) in the solutions containing the above-described analyte or the analogue thereof), namely, use amount of the CFS cannot be said unconditionally depending on kinds of the CFS to be used, however, it is desirable usually, in a reaction solution (the solution containing the analyte or the analogue thereof and the CFS), that the CFS is present in said reaction solution in concentration or more (preferably equal to or higher than two times concentration thereof, and more preferably equal to or higher than five times concentration thereof) which is capable of binding with all of the analytes or analogues thereof corresponding to the detection limit concentration set. In addition, the upper limit of the use amount is not especially limited, however, in consideration of economical efficiency etc., it is equal to or lower than $10^{12}$ times concentration which is capable of binding with all of the analytes or analogues thereof corresponding to the detection limit concentration usually set (preferably equal to or lower than $10^9$ times, and more preferably lower than $10^6$ times).

In more specifically, the CFS may be contained in the above solutions so that the use amount of the CFS in the solution containing the analyte or the analogue thereof and the CFS, becomes, as the lower limit, usually equal to or higher than 10 pM, preferably equal to or higher than 1 nM, and more preferably equal to or higher than 100 nM, and as the upper limit, usually equal to or lower than 10 µM, preferably equal to or lower than 1 µM, and more preferably equal to or lower than 500 nM.

2-6. A Specific Separation Method

The embodiments of the separation method of the present invention will be shown below specifically.

(1) The Separation Method 1

One embodiment of the separation method 1 of the present invention will be shown below.

(1-1) The Non-Competitive Method (1) There is introduced and arranged, between the LB zone and the TB zone at the inside of the capillary for ITP, the solution containing the complex A including the following (a) to (c), and the free (c) labeled CFS not involved in formation of relevant complex A, obtained by contacting, in advance, (a) the analyte in the blood-derived sample, (b) one or more kinds of the mobility-changing CFSs and (c) one or more kinds of the labeled CFSs, at the outside or at the inside of the capillary, by the method for forming the complex relevant to the present invention, as described above.

(2) Then, (i) said complex A is separated from (ii) the free labeled CFS not involved in formation of said complex A, and (iii) the coexisting materials in the blood-derived sample, while concentrating said complex A at the downstream side of the TB zone by ITP, by applying a voltage onto said capillary for ITP, in the presence of the MES ion and/or the glutamate ion.

(1-2) The Competitive Method

In the case of using the labeled analogue:

(1) There is introduced and arranged, between the LB zone and the TB zone at the inside of the capillary for ITP, the solution containing the complex A' including the following (a') and (b), the complex B' including the following (a) and (b), and the free (a') labeled analogue not involved in formation of relevant complex A', obtained by contacting, in advance, (a') the labeled analogue and (b) one or more kinds of the mobility-changing CFSs, and (a) the analyte in the blood-derived sample and (b) one or more kinds of the mobility-changing CFSs, at the outside or at the inside of the capillary, by the method for forming the complex relevant to the present invention, as described above.

(2) Then, (i) said complex A' is separated from (ii) the free labeled analogue not involved in formation of said complex A', and (iii) the coexisting materials in the blood-derived sample, while concentrating said complex A' at the downstream side of the TB zone, by ITP, by applying a voltage onto said capillary for ITP, in the presence of the MES ion and/or the glutamate ion.

In the case of using the mobility-changing analogue:

(1) There is introduced and arranged, between the LB zone and the TB zone at the inside of the capillary for ITP, the solution containing the complex A" including the following (a") and (c), the complex B" including the following (a) and (c), and the free (c) labeled CFS not involved in formation of relevant complex A", obtained by contacting, in advance, (a") the mobility-changing analogue and (c) one or more kinds of the labeled CFSs, and (a) the analyte in the blood-derived sample and (c) one or more kinds of the labeled CFSs, at the outside or at the inside of the capillary, by the method for forming the complex relevant to the present invention, as described above.

(2) Then, (i) said complex A" is separated from (ii) the free labeled analogue not involved in formation of said complex A" and/or said complex B", and (iii) the coexisting materials in the blood-derived sample, while concentrating said complex A" at the downstream side of the TB zone, by ITP, by applying a voltage onto said capillary for ITP, in the presence of the MES ion and/or the glutamate ion.

(2) The Separation Method 2

One embodiment of the separation method 2 of the present invention will be shown below.

(2-1) The Non-Competitive Method (a) In the case of using the blood-derived sample-containing solution, the mobility-changing CFS-containing solution, and the labeled CFS-containing solution:

(1) There is introduced and arranged, between the LB zone and the TB zone at the inside of the capillary for ITP, 1) a solution containing one or more kinds of the labeled CFS, 2) a solution containing the blood-derived sample including the analyte and 3) a solution containing one or more kinds of the mobility-changing CFSs, without mixing these solutions, in advance, at the outside of the capillary, and so that each of a zone of the solution containing one or more kinds of the labeled CFS, a zone of the solution containing the blood-derived sample including the analyte, and a zone of the solution containing one or more kinds of mobility-changing CFSs, is formed separately (so that liquid-liquid interface is formed), and so that the following complex A is formed in applying a voltage onto the capillary (in carrying out ITP).

(2) Then, (i) said complex A is separated from (ii) the free labeled CFS not involved in formation of said complex A, and (iii) the coexisting materials in the blood-derived sample, while concentrating said complex A at the downstream side of the TB zone, by forming said complex A including the following (a) to (c), by contacting electrophoretically, (a) said analyte, (b) one or more kinds of the mobility-changing CFSs and (c) one or more kinds of the labeled CFS, by ITP, by applying a voltage onto said capillary, in the presence of the MES ion and/or the glutamate ion, before these solutions are mixed uniformly, without depending on molecular diffusion, or without carrying out physical mixing.

(b) In the case of using the (blood-derived sample and the labeled CFS)-containing solution and the mobility-changing CFS-containing solution:

(1) There is introduced and arranged, between the LB zone and the TB zone at the inside of the capillary for ITP, 1) a solution containing the blood-derived sample including the analyte and one or more kinds of the labeled CFS (a solution containing the complex of the analyte and the labeled CFS), and 2) a solution containing one or more kinds of the mobility-changing CFSs, without mixing these solutions, in advance, so that each of a zone of the solution containing the blood-derived sample including the analyte and one or more kinds of the labeled CFS, and a zone of the solution containing one or more kinds of the mobility-changing CFSs, is formed separately (so that liquid-liquid interface is formed), and so that the following complex A is formed in applying a voltage onto the capillary (in carrying out ITP).

(2) Then, (i) said complex A is separated from (ii) the free labeled CFS not involved in formation of said complex A, and (iii) the coexisting materials in the blood-derived sample, while concentrating said complex A at the downstream side of the TB zone, by forming said complex A including the following (a) to (c), by contacting electrophoretically, the complex including (a) said analyte and (c) one or more kinds of the labeled CFS and (b) one or more kinds of the mobility-changing CFSs, by ITP, by applying a voltage onto said capillary, in the presence of the MES ion and/or the glutamate ion, before these solutions are mixed uniformly, without depending on molecular diffusion, or without carrying out physical mixing.

(2-2) The Competitive Method (c) In the case of using the (blood-derived sample and the labeled analogue)-containing solution and the mobility-changing CFS-containing solution:

(1) There is introduced and arranged, between the LB zone and the TB zone at the inside of the capillary for ITP, 1) a solution containing the blood-derived sample including the analyte and the labeled analogue, and 2) a solution containing one or more kinds of the mobility-changing CFSs, without mixing these solutions, in advance, at the outside of the capillary, so that each of a zone of the solution containing the blood-derived sample including the analyte and the labeled analogue, and a zone of the solution containing one or more kinds of the mobility-changing CFSs, is formed separately (so that liquid-liquid interface is formed), and so that the following complex A' and complex B' are formed in applying a voltage onto the capillary (in carrying out ITP).

(2) Then, (i) said complex A' is separated from (ii) the free (a') labeled analogue not involved in formation of said complex A', and (iii) the coexisting materials in the blood-derived sample, while concentrating said complex A' at the downstream side of the TB zone, by forming said complex A' including the following (a') and (b), by contacting electrophoretically, (a') the labeled analogue and (b) one or more kinds of the mobility-changing CFSs, and by forming said complex B' including the following (a) and (b), by contacting electrophoretically, (a) said analyte and (b) one or more kinds of the mobility-changing CFSs, by ITP, by applying a voltage onto said capillary, in the presence of the MES ion and/or the glutamate ion, before these solutions are mixed uniformly, without depending on molecular diffusion, or without carrying out physical mixing.

(d) In the case of using the blood-derived sample-containing solution and the (labeled analogue and the mobility-changing CFS)-containing solution:

(1) There is introduced and arranged, between the LB zone and the TB zone at the inside of the capillary for ITP, 1) a solution containing the blood-derived sample including the analyte, and 2) a solution containing the labeled analogue and one or more kinds of the mobility-changing CFSs (a solution containing the complex A' of (a') the labeled analogue and (b) one or more kinds of the mobility-changing CFSs), without mixing these solutions, in advance, at the outside of the capillary, so that each of a zone of the solution containing the blood-derived sample including the analyte, and a zone of the solution containing the labeled analogue and one or more kinds of the mobility-changing CFSs, is formed separately (so that liquid-liquid interface is formed), and so that the following complex B' is formed in applying a voltage onto the capillary (in carrying out ITP).

(2) Then, (i) said complex A' is separated from (ii) the free (a') labeled analogue not involved in formation of said complex A', and (iii) the coexisting materials in the blood-derived sample, while concentrating said complex A' at the downstream side of the TB zone, by forming said complex B' including the following (a) and (b), by contacting electrophoretically, (a) the labeled analyte and the complex A', by ITP, by applying a voltage onto said capillary, in the presence of the MES ion and/or the glutamate ion, before these solutions are mixed uniformly, without depending on molecular diffusion, or without carrying out physical mixing.

(e) In the case of using the labeled analogue-containing solution, and the (blood-derived sample and the mobility-changing CFS)-containing solution:

(1) There is introduced and arranged, between the LB zone and the TB zone at the inside of the capillary for ITP, 1) a solution containing the labeled analogue, and 2) a solution containing the blood-derived sample including the analyte and one or more kinds of the mobility-changing CFSs (a solution including the complex B' of the analyte and one or more kinds of the mobility-changing CFSs), without mixing these solutions, in advance, at the outside of the capillary, so that each of a zone of the solution containing labeled analogue, and a zone of the solution containing the blood-derived sample including the analyte and one or more kinds of the mobility-changing CFSs, is formed separately (so that liquid-liquid interface is formed), and so that the following complex B' is formed in applying a voltage onto the capillary (in carrying out ITP).

(2) Then, (i) said complex A' is separated from (ii) the free (a') labeled analogue not involved in formation of said complex A', and (iii) the coexisting materials in the blood-derived sample, while concentrating said complex A' at the downstream side of the TB zone, by forming said complex A' including the following (a') and (b), by contacting, electrophoretically, (a') said labeled analogue and the complex B', and/or by contacting, electrophoretically, (a') and said labeled analogue and (b) one or more kinds of the mobility-changing CFSs not involved in formation of said complex B', by ITP, by applying a voltage onto said capillary, in the presence of the MES ion and/or the glutamate ion, before these solutions are mixed uniformly, without depending on molecular diffusion, or without carrying out physical mixing.

(f) In the case of using the blood-derived sample-containing solution, the labeled analogue-containing solution, and the mobility-changing CFS-containing solution:

(1) There is introduced and arranged, between the LB zone and the TB zone at the inside of the capillary for ITP, 1) a solution containing the blood-derived sample including the analyte, 2) a solution containing the labeled analogue, and 3) a solution containing one or more kinds of the mobility-changing CFSs, without mixing these solutions, in advance, at the outside of the capillary, so that each of a zone of the solution containing the blood-derived sample including the analyte, a zone of the solution containing the labeled analogue, and a zone of the solution containing one or more kinds of the mobility-changing CFSs, is formed separately (so that liquid-liquid interface is formed), and so that the following complexes A' and B' are formed in applying a voltage onto the capillary (in carrying out ITP).

(2) Then, (i) said complex A' is separated from (ii) the free (a') labeled analogue not involved in formation of said complex A', and (iii) the coexisting materials in the blood-derived sample, while concentrating said complex A' at the downstream side of the TB zone, by forming said complex A' including the following (a') and (b), by contacting, electrophoretically, (a') the labeled analogue and (b) one or more kinds of the mobility-changing CFSs, as well as by forming said complex B' including (a) and (b), by contacting, electrophoretically, (a) said analyte and said complex A', by ITP, by applying a voltage onto said capillary, in the presence of the MES ion and/or the glutamate ion, before these solutions are mixed uniformly, without depending on molecular diffusion, or without carrying out physical mixing.

(g) In the case of using the labeled analogue-containing solution, the blood-derived sample-containing solution, and the mobility-changing CFS-containing solution:

(1) There is introduced and arranged, between the LB zone and the TB zone at the inside of the capillary for ITP, 1) a solution containing the labeled analogue, 2) a solution containing the blood-derived sample including the analyte, and 3) a solution containing one or more kinds of the mobility-changing CFSs, without mixing these solutions, in advance, at the outside of the capillary, so that each of a zone of the solution containing the labeled analogue, a zone of the solution containing the blood-derived sample including the analyte, and a zone of the solution containing one or more kinds of the mobility-changing CFSs, is formed separately (so that liquid-liquid interface is formed), and so that the following complex A' and complex B' are formed in applying a voltage onto the capillary (in carrying out ITP).

(2) Then, (i) said complex A' is separated from (ii) the free (a') labeled analogue not involved in formation of said complex A', and (iii) the coexisting materials in the blood-derived sample, while concentrating said complex A' at the downstream side of the TB zone, by forming said complex B' including the following (a) and (b), by contacting, electrophoretically, (a) said analyte and (b) one or more kinds of the mobility-changing CFSs, as well as by forming said complex A' including (a') and (b), by contacting, electrophoretically, (a') said labeled analogue and said complex B', or by contacting, electrophoretically, (a') said labeled analogue and (b) one or more kinds of the mobility-changing CFSs not involved in formation of the complex B', by ITP, by applying a voltage onto said capillary, in the presence of the MES ion and/or the glutamate ion, before these solutions are mixed uniformly, without depending on molecular diffusion, or without carrying out physical mixing.

(h) In the case of using the blood-derived sample-containing solution, and the (mobility-changing analogue and the labeled CFS)-containing solution:

(1) There is introduced and arranged, between the LB zone and the TB zone at the inside of the capillary for ITP, 1) a solution containing the blood-derived sample including the analyte, and 2) a solution containing the mobility-changing analogue and one or more kinds of the labeled CFSs (a solution containing the complex A" of (a') the mobility-changing analogue and (c) the labeled CFSs), without mixing these solutions, in advance, at the outside of the capillary, so that each of a zone of the solution containing the blood-derived sample including the analyte, and a zone of the solution containing mobility-changing analogue and one or more kinds of the labeled CFSs, is formed separately (so that liquid-liquid interface is formed), and so that the following complex B" is formed in applying a voltage onto the capillary (in carrying out ITP).

(2) Then, (i) said complex A" is separated from (ii) the free (c) labeled CFS not involved in formation of said complex A" and/or the complex B", and (iii) the coexisting materials in the blood-derived sample, while concentrating said complex A" at the downstream side of the TB zone, by forming the complex B" including (a) and (c), by contacting, electrophoretically, (a) said analyte and said complex A", by ITP, by applying a voltage onto said capillary, in the presence of the MES ion and/or the glutamate ion, before these solutions are mixed uniformly, without depending on molecular diffusion, or without carrying out physical mixing.

(i) In the case of using (the blood-derived sample and the labeled CFS)-containing solution, the mobility-changing analogue-containing solution:

(1) There is introduced and arranged, between the LB zone and the TB zone at the inside of the capillary for ITP, 1) a solution containing the blood-derived sample including the analyte and one or more kinds of the labeled CFSs (a solution containing the complex B" of (a) the analyte and (c) one or more kinds of the labeled CFSs), and 2) a solution containing the mobility-changing analogue, without mixing these solutions, in advance, at the outside of the capillary, so that each of a zone of the solution containing the blood-derived sample including the analyte and one or more kinds of the labeled CFSs, and a zone of the solution containing mobility-changing analogue, is formed separately (so that liquid-liquid interface is formed), and so that the following complex A" is formed in applying a voltage onto the capillary (in carrying out ITP).

(2) Then, (i) said complex A" is separated from (ii) the free (c) labeled CFS not involved in formation of said complex A" and/or the complex B", and (iii) the coexisting materials in the blood-derived sample, while concentrating said complex A" at the downstream side of the TB zone, by forming the complex A" including (a") and (c), by contacting, electrophoretically, (a") the mobility-changing analogue and said complex B", and/or by contacting, electrophoretically, (a") the mobility-changing analogue and (c) one or more kinds of the labeled CFSs not involved in formation of said complex B", by ITP, by applying a voltage onto said capillary, in the presence of the MES ion and/or the glutamate ion, before these solutions are mixed uniformly, without depending on molecular diffusion, or without carrying out physical mixing.

3. Additional Separation (CZE, CGE)

The complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs), and the coexisting materials in the blood-derived sample, which were separated by the above separation method of the present invention (the step of condensation and separation), can be separated further electrically, by capillary zone electrophoresis (CZE) or capillary-gel electrophoresis (CGE), namely, by introducing them between the two LB zones at the inside of the capillary for carrying out CZE or CGE, and by applying a voltage onto said capillary, in the presence of the MES ion and/or the glutamate ion.

Separation of the complex relevant to the present invention and the coexisting materials in the blood-derived sample, which were separated by ITP in the step of separation of the present invention, can be carried out further efficiently, by carrying out CZE or CGE, further, in the presence of the MES ion and/or the glutamate ion.

That is, in the separation method of the present invention, it is preferable that [B-1] (i) said complex A and (iii) the coexisting materials in the blood-derived sample, [B-2] (i) said complex A' and (iii) the coexisting materials in the blood-derived sample, or [B-3] (i) said complex A" and (iii) the coexisting materials in the blood-derived sample, are further separated (the step of additional separation) by introducing (a step of re-introduction) them between the two LB zones at the inside of the capillary for carrying out CZE or CGE (hereafter may be abbreviated as the capillary for CZE/CGE), and by applying a voltage onto said capillary, in the presence of the MES ion and/or the glutamate ion.

(1) The Step of Re-Introduction

The step of re-introduction is a step of making the complex relevant to the present invention [the complex A, the complex A', or the complex A"], and the coexisting materials in the blood-derived sample, which were separated by the step of condensation and separation, existed between the two LB zones at the inside of the capillary for CZE/CGE (a step of introduction and arrangement), to carry out CZE or CGE, in the presence of the MES ion and/or the glutamate ion.

Here, those to be introduced between the two LB zones (hereafter may be abbreviated as re-introduction substances) are enough to be the zone containing the complex relevant to the present invention and the zone containing the coexisting materials which were separated in the step of concentration and separation, as well as the zone existing between these two zones, however, usually the solution existing at the downstream side of the TB zone, separated in the step of condensation and separation, in other words, the zone containing a substance moved faster than the TB zone by ITP is introduced. It is preferably the solution existing at the downstream side of the trailing ion zone, separated in the step of condensation and separation, in other words, the zone containing a substance moved faster than the trailing ion by ITP.

In this connection, such zones to be introduced (re-introduction substances) are enough to be those existing at the upstream side of the LB zone or at the upstream side of the leading ion zone, namely, those positioned between the TB zone (the trailing ion zone) and the LB zone or the leading ion zone, separated by the step of condensation and separation, however, as will be described later, in the case where the step of condensation and separation, and the step of additional separation are carried out using the same capillary, etc., all of the zones existing at the downstream side of the TB zone (preferably the trailing ion zone), separated by the step of condensation and separation are usually introduced.

In addition, because the MES ion and/or the glutamate ion exhibit intermediate electrophoretic movement between those of the complex relevant to the present invention and the coexisting materials, a zone (solution) containing the MES ion and/or the glutamate ion results in to be present between the zone containing the complex relevant to the present invention, and the zone containing the coexisting materials, by ITP (the step of condensation and separation). Therefore, by introducing (arranging) the above re-introduction substances between the two LB zones at the inside of the capillary for CZE/CGE, CZE or CGE (the step of additional separation) to be carried out afterwards results in to be carried out in the presence of the MES ion and/or the glutamate ion.

Therefore, the above re-introduction substances include the following one specifically:

[B-1] in the case of the non-competitive method:

(1) The zone including the complex A which includes the analyte in the blood-derived sample, one or more kinds of mobility-changing CFSs and one or more kinds of the labeled CFSs, (2) the zone including the MES ion and/or the glutamate ion and (3) the zone including the coexisting materials in the blood-derived sample, which are positioned at the downstream side of the TB zone, after carrying out the above step of condensation and separation (ITP).

In this connection, there may also be the case where the free mobility-changing CFS not involved in formation of the complex, the labeling substance non-bound (reacted) with the CFS (a non-bound labeling substance), etc. other than the above, is contained in the zone (1). In addition, there may also be the case where the zone including the mobility-changing CFS or the zone including the non-bound labeling substance other than the above, is contained in the re-introduction substances.

Incidentally, introduction order of the above re-introduction substances is determined as a result of the step of condensation and separation, according to electrophoretic mobility which each of the substances has, however, usually it is in the order of (1), (2) and (3) in a direction from the upstream side toward the downstream side.

[B-2] In the case of the competitive method using the labeled analogue:

(1) The zone including the complex A' which contains the labeled analogue and one or more kinds of the mobility-changing CFSs,
(2) the zone including the MES ion and/or the glutamate ion and
(3) the zone including the coexisting materials in the blood-derived sample, which are positioned at the downstream side of the TB zone, after carrying out the above step of condensation and separation (ITP).

In this connection, there may also be the case where the complex B' including the analyte and one or more kinds of the mobility-changing CFSs, the free mobility-changing CFS not involved in formation of the complex, and the labeling substance non-bound (reacted) with the CFS (a non-bound labeling substance), other than the above, are contained in the zone (1). In addition, there may also be the case where the zone including the complex B', the zone including the mobility-changing CFS or the zone including the non-bound labeling substance, other than the above, is contained in the re-introduction substances.

Incidentally, introduction order of the above re-introduction substances is determined as a result of the step of condensation and separation, according to electrophoretic mobility which each of the substances has, however, usually it is in the order of (1), (2) and (3) in a direction from the upstream side toward the downstream side.

[B-3] In the case of the competitive method using the mobility-changing analogue:

(1) The zone including the complex A" including the mobility-changing analog and one or more kinds of the labeled CFSs, (2) the zone including the MES ion and/or the glutamate ion and (3) the zone including the coexisting materials in the blood-derived sample, which are positioned at the downstream side of the TB zone, after carrying out the above step of condensation and separation (ITP).

In this connection, there may also be the case where the labeling substance non-bound (reacted) with the CFS (a non-bound labeling substance), other than the above, is contained in the zone (1). In addition, there may also be the case where the zone including the non-bound labeling substance, other than the above, is contained in the re-introducing substance. In some cases, there may also be the case where the zone including the complex B", which contains the analyte and one or more kinds of the labeled CFSs, is contained in the zone (1), or the zone including the complex B" is contained, as the re-introduction substances.

Incidentally, introduction order of the above re-introduction substances is determined as a result of the step of condensation and separation, according to electrophoretic mobility which each of the substances has, however, usually it is in the order of (1), (2) and (3) in a direction from the upstream side toward the downstream side.

In the step of re-introduction, as the method for introducing the re-introduction substances to the inside of the capillary for CZE/CGE, an introduction method known itself can be used, as long as it is a method capable of making said solution existed (making it introduced and arranged) between the two LB zones at the inside of the capillary for CZE/CGE.

As such an introduction method known itself, there are included a method for introducing and arranging the solution containing the complex relevant to the present invention, in the step of introduction of the above separation method 1, to the inside of the capillary for ITP; a method for introducing and arranging the solution including the analyte or the analogue thereof, and the solution including one or more kinds of the CFSs, in the step of introduction of the separation method 2, to the inside of the capillary for ITP; etc.

In this connection, as will be described later, in the case where the step of condensation and separation, and the step of additional separation are carried out using the same capillary (at the inside of the same capillary), they can be carried out by using the capillary (capillary chip), for example, described in WO2007/027495, WO2007/121263, and JP-A-2006-317357, according to the method described therein.

(2) The Step of Additional Separation (CZE, CGE)

The step of additional separation may be carried out according to a method known itself, in a method of CZE and CGE, known itself, for separation, for example, by introducing a substance between the two LB zones at the inside of the capillary for CZE/CGE, and moving said substance electrically, except that the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs), and the coexisting materials in the blood-derived sample, which were separated by the separation method of the present invention (the step of condensation and separation: ITP), are separated electrically by CZE or CGE, in the presence of the MES ion and/or the glutamate ion, and as for materials, reagents etc. to be used as well, those used in a method known itself may be used.

In the step of additional separation, the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs), and the above coexisting materials in the blood-derived sample, which have already been separated in the step of condensation and separation (by ITP), are further separated at the inside of the capillary for CZE/CGE, by electrically moving them by CZE or CGE.

In this connection, further separation of the complex relevant to the present invention and the free labeling substance-containing molecule (the labeled CFS, the labeled analogue, and the analyte-labeled CFS complex) not involved in formation of said complex, which have already been separated in the step of condensation and separation, is not necessary here, however it is preferable to further separate these similarly as in the coexisting materials.

For example, in the case of the non-competitive method, it is enough to further separate, at least, the complex A and the coexisting materials in the blood-derived sample (in particular, bilirubin, a metabolite thereof, or a complex of bilirubin and protein, etc.), and it is not necessary to separate the mobility-changing CFS from said complex.

In addition, in the case of the competitive method using, for example, the labeled analogue, it is enough to further separate, at least, the complex A' and the above coexisting materials in the blood-derived sample (in particular, bilirubin, a metabolite thereof, or a complex of bilirubin and protein, etc.), and it is not necessary to separate the mobility-changing CFS or the complex B' (the complex of the analyte and the mobility-changing CFS) from said complex. In addition, in the case of the competitive method using the mobility-changing analogue, it is enough to further separate, at least, the complex A" and the above coexisting materials in the blood-derived sample (in particular, bilirubin, a metabolite thereof, or a complex of bilirubin and protein, etc.).

(2-1) The MES Ion and the Glutamate Ion

The step of additional separation is one for carrying out CZE or CGE, in the presence of the MES ion and/or the glutamate ion, however, because a zone containing the MES ion and/or the glutamate ion is included in the re-introduction substances to be introduced in the above step of re-introduction, in the case of carrying out the step of introduction, the step of concentration and separation, the step of re-introduction, and the step of additional separation of the present invention, CZE or CGE results in to be carried out in the presence of the MES ion and/or the glutamate ion.

Therefore, it is not necessary to make existed the MES ion and/or the glutamate ion intentionally, however, it may be allowed that for example, in the step of re-introduction, to newly introduce a solution (zone) containing the MES ion and/or the glutamate ion, or the MES ion and/or the glutamate ion are made existed in either of or both of the two LBs to be used in the step of additional separation.

In this connection, use concentration, introduction method, etc. of the MES ion and/or the glutamate ion, in this case, are as described above.

(2-2) Two LBs

The LB to be used in the step of additional separation, the leading ion in the LB and an introduction method to the inside of the capillary for CZE/CGE are the same as in the above separation method 1, and specific example, use concentration, pH and preferable embodiment thereof are as described above.

In this connection, the two LBs (and the leading ions) may be the same or different each other. In addition, it is not necessary that the LB to be used in the step of additional separation and the LB to be used in the step of concentration and separation are the same, and different LBs may be used by selecting these, as appropriate.

In addition, in the case where the step of condensation and separation, and the step of additional separation are carried out using the same capillary (at the inside of the same capillary), it is general that the LB arranged at the most downstream side among the two LBs has the same (common) composition as that of the LB to be used in the step of condensation and separation.

(2-3) CZE and CGE Conditions (Applied Voltage, pH, Temperature and Time)

The step of additional separation may be carried out by using a method which is capable of sufficiently separating the complex relevant to the present invention, from the coexisting materials in the blood-derived sample, and if necessary, the free labeling substance-containing molecule (the labeled CFS, the labeled analogue, and the analyte-labeled CFS complex) not involved in formation of said complex, and as such a method, there can be used CZE, where the inside of the capillary, known itself, to be used usually in this field, is fundamentally filled only with an electrophoresis buffer solution, and separation of objective substances is carried out by moving each of the substances in different speed depending on the charge size thereof [Literature: H. Hisamoto at al., Chem. Commun., (2001), 2662; WO2007/027495; WO2007/121263; JP-A-2006-317357 etc.]; and CGE, where the objective substances are separated, by using fillers such as polymers having molecular sieve effect, etc., depending on the size of molecules generating interaction between the charges, which the objective substances have, and the polymers [Literature: S. Hjerten, J. Chromatogr., (1987), 397, 409; WO2007/027495; WO2007/121263; JP-A-2006-317357 etc.].

In this connection, in the present invention, reagents etc. to be used in the above CZE and CGE can be used, as appropriate. In addition, such reagents, operation methods in separation and other conditions etc. can be selected, as appropriate, according to description of the above literature etc.

Applied voltage in the step of additional separation may be in a range where the complex relevant to the present invention from the coexisting materials in the blood-derived sample, and if necessary, the free labeling substance-containing molecule (the labeled CFS, the labeled analogue, and the analyte-labeled CFS complex) not involved in formation of said complex, are sufficiently separated, and may be selected, as appropriate, from those to be used usually in this field. In more specifically, voltage is applied so that there is attained electric field intensity in a range of, as the lower limit, usually equal to or higher than 5 V/cm, preferably equal to or higher than 10 V/cm, more preferably equal to or higher than 50 V/cm, further preferably equal to or higher than 500 V/cm, and particularly preferably equal to or higher than 1000 V/cm, and as the upper limit, usually equal to or lower than 10000 V/cm, preferably equal to or lower than 5000 V/cm, and more preferably equal to or lower than 2000 V/cm.

In addition, other separation conditions (for example, pH, temperature, time etc.) may be in a range where the complex relevant to the present invention from the coexisting materials in the blood-derived sample, and if necessary, the free labeling substance-containing molecule (the labeled CFS, the labeled analogue, and the analyte-labeled CFS complex) not involved in formation of said complex, are sufficiently separated, and may be selected, as appropriate, according to a method known itself to be used usually in this field.

Specifically, the pH is, as the lower limit, usually equal to or higher than 2, preferably equal to or higher than 5, and as the upper limit, usually equal to or lower than 10, preferably equal to or higher than 9, and the temperature is, as the lower limit, usually equal to or higher than 0° C., preferably equal to or higher than 5° C., more preferably equal to or higher than 10° C., and as the upper limit, usually equal to or lower than 50° C., preferably equal to or higher than 40° C. and more preferably equal to or lower than 30° C.

The ITP time differs depending on association constant of the CFS to be used to the analyte or the analogue thereof, and the case of lower association constant requires relatively longer reaction time, while the case of higher association constant requires relatively shorter reaction time. In more specifically, for example, the lower limit is usually equal to or longer than 10 seconds, preferably equal to or longer than 30 seconds, and more preferably equal to or longer than 1 minute, and the upper limit is usually equal to or shorter than 1 hour, preferably equal to or shorter than 30 minutes, more preferably equal to or shorter than 10 minutes and further preferably equal to or shorter than 5 minutes.

(2-5) Use of a Negatively Charged Polymer

In the present invention, it is preferable to carry out the step of additional separation in the presence of a charged polymer, having negative (minus) charge (the negatively-charged polymer).

That is, by carrying out separation of the complex relevant to the present invention (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs) by CZE or CGE, in the presence of the negatively-charged polymer, it becomes possible to separate non-bound labeling substance (reagent noise) present in the re-introduction substances, which were introduced in the step of re-introduction, and the complex relevant to the present invention.

In this connection, said non-bound labeling substance (reagent noise) is the labeling substance itself as above-described, which is not bound with the CFS or the analogue, and means the un-reacted labeling substance generating in producing the labeled CFS or the labeled analogue (namely, in reacting the labeling substance with the CFS or the analogue), or the labeling substance dissociated, generated by decomposition of the labeled CFS or the labeled analogue. And such non-bound labeling substance is present in the solution containing the labeled CFS or the labeled analogue, and may be introduced to the inside of the capillary for CZE/CGE in the step of re-introduction, in some cases, depending on electrophoretic mobility thereof. In such a case, in the step of additional separation (CZE or CGE) to be carried out subsequently, it may cause adverse effects on analysis, for example, increase in background etc. Therefore, if such a non-bound labeling substance and the complex relevant the present invention can be separated sufficiently, analysis in higher precision becomes possible.

In addition, by carrying out the step of concentration and separation, in the presence of the negatively-charged polymer, influence of the coexisting materials co-present in the blood-derived sample, which gives adverse effect, can be reduced as well.

The negatively charged polymer to be used in the present invention includes polyanionic polymer, in more specifically, polyanionic polysaccharoid, such as, for example, heparin, heparan sulfate, chondroitin sulfate, dextran sulfate, polytungstate, phosphotungstate, hyaluronate, dermatan sulfate, polyanethole sulfate; polyanionic synthetic polymer compound such as, for example, poly-dIdC, polyvinyl sulfate, polyacrylic acid; salts thereof (for example, sodium salt, potassium salt, lithium salt; ammonium salt); and a complex thereof. These negatively-charged polymers may be used as one kind, or as two or more kinds by combination, as appropriate.

Among these as above, anionic polysaccharide is preferable, and heparin or a salt thereof (for example, an alkali metal salt such as a sodium salt, a potassium salt, a lithium salt, or an ammonium salt etc.) is particularly preferable. In this connection, heparin and the salt thereof is not especially limited, and low molecular weight heparin (and the salt thereof) [a molecular weight of about 1000 to 10000; an average molecular weight of about 4000 to 5000] or usual (un-fractionated) heparin (and the salt thereof) [a molecular weight of about 3000 to 30000; an average molecular weight of about 12000 to 15000] can be used as well, however, non-fractionated heparin is preferable.

In carrying out the step of additional separation, a method for making the above negatively-charged polymer existed is not especially limited, as long as it is capable of carrying out CZE or CGE, in the presence of the negatively-charged polymer eventually.

As such a method, there is included, for example, a method for making the above negatively-charged polymer existed in the solution to be introduced into the capillary (the capillary for ITP or the capillary for CZE/CGE) [for example, various solutions (a solution containing one or more kinds of any of the analyte, the analogue and CFS; the LB, the TB, liquid etc.) to be introduced in the above separation method 1 or the separation method 2], etc. In this connection, specifically, as described above, it may be carried out according to a method for making existed the MES ion and/or the glutamate ion in carrying out ITP in the separation method 1, or a method for making existed the MES ion and/or the glutamate ion in carrying out ITP in the separation method 2.

Among these, it is preferable that the negatively-charged polymer is made coexisted in the solution (zone) not containing the blood-derived sample including the analyte [the LB, the TB, the solution containing (b) one or more kinds of the mobility-changing CFSs, the solution containing (c) one or more kinds of the labeled CFSs, the solution containing (a') the labeled analogue, and the solution containing (a") the mobility-changing analogue in (1-1) of the separation method 1; the solution containing (b), the solution containing (c), the solution containing (b) and (c), the solution containing (a'), the solution containing (b), the solution containing (a') and (b), the solution containing (a"), the solution containing (c), the solution containing (a") and (c) in (1-2) of the separation method 1; the solution containing (b) one or more kinds of the mobility-changing CFSs, the solution containing (c) one or more kinds of the labeled CFSs, the solution containing (a') the labeled analogue, the solution containing (b) one or more kinds of the mobility-changing CFSs, the solution containing (a") the mobility-changing analogue, the solution containing (c) one or more kinds of the labeled CFSs, the solution containing (b) and (c), the solution containing (a') and (b), the solution containing (a") and (c) in the separation method 2; etc.], and it is particularly preferable to be contained at least in the LB (zone).

In more specifically, in the case of the non-competitive method, it is preferable to be contained, for example, in one or more kinds of solutions selected from the LB (zone), a solution containing one or more kinds of the mobility-changing CFSs, and a solution containing one or more kinds of the labeled CFSs; or in one or more kinds of solutions selected from the LB (zone), and a solution containing one or more kinds of the mobility-changing CFSs. It is particularly preferable to be contained at least in the LB (zone).

In addition, in the case of the competitive method, it is preferable to be contained, for example, in one or more kinds of solutions selected from the LB (zone), and a solution containing one or more kinds of the mobility-changing CFSs; in one or more kinds of solutions selected from the LB (zone), and a solution containing the labeled analogue and one or more kinds of the mobility-changing CFSs; in one or more kinds of solutions selected from the LB (zone), a solution containing the labeled analogue, and a solution containing one or more kinds of the mobility-changing CFSs; in one or more kinds of solutions selected from the LB (zone), and a solution including one or more kinds of the labeled CFSs; or in one or more kinds of solutions selected from the LB (zone), a solution containing the mobility-changing analogue, and a solution containing one or more kinds of the labeled CFSs. It is particularly preferable to be contained at least in the LB (zone).

Use amount of the above negatively-charged polymer cannot be said unconditionally, because of dependency on kinds etc. of the negatively-charged polymer to be used, however, for example, as concentration in the LB, as the lower limit, it is usually equal to or higher than 0.01% (w/v), preferably equal to or higher than 0.05% (w/v), and more preferably equal to or higher than 0.5% (w/v); and as the upper limit, usually equal to or lower than 50% (w/v), preferably equal to or lower than 10% (w/v), and further preferably equal to or lower than 5% (w/v), and among these about 1% (w/v) is particularly preferable. In addition, as concentration in solutions other than the LB (TB or the above various solutions in the separation method 1 or the separation method 2), as the lower limit, it is usually equal to or higher than 0.001% (w/v), preferably equal to or higher than 0.01% (w/v), more preferably equal to or higher than 0.02% (w/v), and further preferably equal to or higher than 0.025% (w/v); and as the upper limit, usually equal to or lower than 10% (w/v), preferably equal to or lower than 5% (w/v), more preferably equal to or lower than 1% (w/v) and further preferably equal to or lower than 0.05% (w/v). In this connection, because containment of a large amount of said negatively-charged polymer in the solutions other than the LB results in concentration of noise components (the coexisting materials) which give influence on measurement, and possibility of adverse effect on measurement, it is necessary to pay attention.

(2-5) The Capillary (Channel)

As described above, the step of additional separation is carried out in the capillary for CZE/CGE, and as such a capillary, the same one as the capillary for ITP used in the step of concentration and separation is included. In addition, a material and inner diameter etc. of the capillary are also as described above.

In addition, the step of concentration and separation, and the step of additional separation are carried out usually using the same capillary (at the inside of the same capillary). That is, as the capillary to be used in the present invention, one having at least a part capable of carrying out the step of concentration and separation (ITP) of the present invention, and a part capable of carrying out the step of additional separation (CZE or CGE) of the present invention is preferable. These parts may be present each independently in the capillary, or a part thereof or all of them may be present in a duplicated manner. In other words, as the capillary to be used in the separation method of the present invention, one having a part capable of carrying out ITP, and a part capable of carrying out CZE or CGE is preferable.

As such the capillary (channel) and a chip having this, there are include the capillary (channel) and the chip described, for example, in WO2007/027495, WO2007/121263, and JP-A-2006-317357.

(2-6) A Specific Separation Method in Carrying Out the Step of the Additional Separation The embodiment of the separation method in carrying out the step of the additional separation, in the present invention, will be shown specifically below.

One embodiment in the separation method 1 will be shown below.

(2-6-1) The Separation Method 1 Based on the Non-Competitive Method (1) The solution containing the complex A and the free (c) labeled CFS not involved in formation of relevant complex A is introduced and arranged between the LB zone and the TB zone at the inside of the capillary for ITP, as in the step (1) in the "2-6. (1-1) the non-competitive method".

(2) Then, (i) said complex A is separated from (ii) the free labeled CFS not involved in formation of said complex A and (iii) the coexisting materials in the blood-derived sample, while concentrating said complex A at the downstream side of the TB zone, by ITP, in the presence of the MES ion and/or the glutamate ion, as in the step (2) in the [2-6. (1-1) the non-competitive method].

(3) The zone including said complex A, the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A and the coexisting materials in the blood-derived sample are further separated by moving electrically by CZE or CGE, by applying a voltage onto said capillary for CZE/CGE.

(2-6-2) The Separation Method 1 Based on the Competitive Method

The case of using the labeled analogue (1) The solution containing the complex A' including (a') and (b), and the complex B' including (a) and (b), the free (a') labeled analogue not involved in formation of relevant complex A' is introduced and arranged between the LB zone and the TB zone at the inside of the capillary for ITP, as in the step (1) in the [2-6. (1-2) the competitive method•the case of using the labeled analogue].

(2) Then, (i) said complex A' is separated from (ii) the free labeled analogue not involved in formation of said complex A' and (iii) the coexisting materials in the blood-derived sample, while concentrating said complex A' at the downstream side of the TB zone, by ITP, in the presence of the MES ion and/or the glutamate ion, as in the step (2) in [2-6. (1-2) the competitive method•the case of using the labeled analogue].

(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A' and the coexisting materials in the blood-derived sample are further separated by moving electrically by CZE or CGE, by applying a voltage onto said capillary for CZE/CGE.

The case of using the mobility-changing analogue (1) The solution containing the complex A" including (a') and (c), and the complex B" including these (a) and (c), and the free (c) labeled CFS not involved in formation of relevant complex A" is introduced and arranged between the LB zone and the TB zone at the inside of the capillary for ITP, as in the step (1) in the [2-6. (1-2) the competitive method•the case of using the mobility-changing analogue].

(2) Then, (i) said complex A" is separated from (ii) the free labeled CFS not involved in formation of said complex A" and/or said complex B" and (iii) the coexisting materials in the blood-derived sample, while concentrating said complex A" at the downstream side of the TB zone, by ITP, in the presence of the MES ion and/or the glutamate ion, as in the step (2) in [2-6. (1-2) the competitive method•the case of using the mobility-changing analogue].

(3) The zone including said complex A", the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A" and the coexisting materials in the blood-derived sample are further separated by moving electrically by CZE or CGE, by applying a voltage onto said capillary for CZE/CGE.

One embodiment in the separation method 2 of the present invention will be shown below.

(2-6-3) The Separation Method 2 Based on the Non-Competitive Method (a) The case of using the blood-derived sample-containing solution, the mobility-changing CFS-containing solution, and the labeled CFS-containing solution (1) 1) The solution containing one or more kinds of the labeled CFSs, 2) the solution containing the blood-derived sample including the analyte and 3) the solution containing one or more kinds of the mobility-changing CFSs are introduced and arranged between the LB zone and the TB zone at the inside of the capillary for ITP, as in the step (1) in (a) of the [2-6. (2) the separation method 2].

(2) Then, (i) said complex A is separated from (ii) the free labeled CFS not involved in formation of said complex A and (iii) the coexisting materials in the blood-derived sample, while concentrating the complex A, at the downstream side of the TB zone, by forming said complex A including (a) to (c), by contacting, electrophoretically, (a) said analyte, (b) one or more kinds of the mobility-changing CFSs and (c) one or more kinds of the labeled CFSs, by ITP, in the presence of the MES ion and/or the glutamate ion, as in the step (2) in (a) of [2-6. (2) the separation method 2].

(3) The zone including said complex A, the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A and the coexisting materials in the blood-derived sample are further separated by moving electrically by CZE or CGE, by applying a voltage onto said capillary for CZE/CGE.

(b) The case of using (the blood-derived sample and the labeled CFS)-containing solution, and the mobility-changing CFS-containing solution (1) 1) The solution containing the blood-derived sample including the analyte and one or more kinds of the labeled CFSs (the solution containing the complex of the analyte and the labeled CFSs), and 2) the solution containing one or more kinds of the mobility-changing CFSs are introduced and arranged between the LB zone and the TB zone at the inside of the capillary for ITP, as in the step (1) in (b) of [2-6. (2) the separation method 2].

(2) Then, (i) said complex A is separated from (ii) the free labeled CFS not involved in formation of said complex A and (iii) the coexisting materials in the blood-derived sample, while concentrating the complex A, at the downstream side of the TB zone, by forming said complex A including (a) to (c), by contacting, electrophoretically, (a) said analyte, (b) the complex including one or more kinds of the labeled CFSs and (c) one or more kinds of the mobility-changing CFSs, by ITP, in the presence of the MES ion and/or the glutamate ion, as in the step (2) in (b) of [2-6. (2) the separation method 2].

(3) The zone including said complex A, the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A and the coexisting materials in the blood-derived sample are further separated by moving electrically by CZE or CGE, by applying a voltage onto said capillary for CZE/CGE.

(2-6-4) The Separation Method 2 Based on the Competitive Method (c) The case of using (the blood-derived sample and the labeled analogue)-containing solution, and the mobility-changing CFS-containing solution (1) 1) The solution containing the blood-derived sample including the analyte and the labeled analogue, and 2) the solution containing one or more kinds of the mobility-changing CFSs are introduced and arranged between the LB zone and the TB zone at the inside of the capillary for ITP, as in the step (1) in (c) of [2-6. (2) the separation method 2].

(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex A' including (a') and (b), by contacting, electrophoretically, (a') the labeled analogue, and (b) one or more kinds of the mobility-changing CFSs, and by forming said complex B' including (a) and (b), by contacting, electrophoretically, (a) said analyte, and (b) one or more kinds of the mobility-changing CFSs, by ITP, in the presence of the MES ion and/or the glutamate ion, as in the step (2) in (c) of [2-6. (2) the separation method 2].

(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A' and the coexisting materials in the blood-derived sample are further separated by moving electrically by CZE or CGE, by applying a voltage onto said capillary for CZE/CGE.

(d) The case of using the blood-derived sample-containing solution, and (the labeled analogue and the mobility-changing CFS)-containing solution (1) 1) The solution containing the blood-derived sample including the analyte, and 2) the solution containing (a') the labeled analogue and (b) one or more kinds of the mobility-changing CFSs (the solution containing the complex A' of the labeled analogue and one or more kinds of the mobility-changing CFSs) are introduced and arranged between the LB zone and the TB zone at the inside of the capillary for ITP, as in the step (1) in (d) of [2-6. (2) the separation method 2].

(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex B' including (a) and (b), by contacting, electrophoretically, (a) said analyte, and said complex A', by ITP, in the presence of the MES ion and/or the glutamate ion, as in the step (2) in (d) of [2-6. (2) the separation method 2].

(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A' and the coexisting materials in the blood-derived sample are further separated by moving electrically by CZE or CGE, by applying a voltage onto said capillary for CZE/CGE.

(e) The case of using the labeled analogue-containing solution, and (the blood-derived sample and the mobility-changing CFS)-containing solution (1) 1) The solution containing the labeled analogue, and 2) the solution containing the blood-derived sample including the analyte and one or more kinds of the mobility-changing CFSs (the solution including the complex of the analyte and one or more kinds of the mobility-changing CFSs) are introduced and arranged between the LB zone and the TB zone at the inside of the capillary for ITP, as in the step (1) in (e) of [2-6. (2) the separation method 2].

(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex A' including (a') and (b), by contacting, electrophoretically, (a') said labeled analogue, and the complex B', and/or by contacting, electrophoretically, (a') said labeled analogue, and (b) one or more kinds of the mobility-changing CFSs not involved in formation of the complex B', by ITP, in the presence of the MES ion and/or the glutamate ion, as in the step (2) in (e) of [2-6. (2) the separation method 2].

(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A' and the coexisting materials in the blood-derived sample are further separated by moving electrically by CZE or CGE, by applying a voltage onto said capillary for CZE/CGE.

(f) The case of using the blood-derived sample-containing solution, the labeled analogue-containing solution, and the mobility-changing CFS-containing solution (1) 1) The solution containing the blood-derived sample including the analyte, 2) the solution containing the labeled analogue and 3) the solution containing one or more kinds of the mobility-changing CFSs are introduced and arranged between the LB zone and the TB zone at the inside of the capillary for ITP, as in the step (1) in (f) of [2-6. (2) the separation method 2].

(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex A' including (a') and (b), by contacting, electrophoretically, (a') the labeled analogue, and (b) one or more kinds of the mobility-changing CFSs, and by forming said complex B' including (a) and (b) by contacting, electrophoretically, (a) said analyte, and said complex A', by ITP, in the presence of the MES ion and/or the glutamate ion, as in the step (2) in (f) of [2-6. (2) the separation method 2].

(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A' and the coexisting materials in the blood-derived sample are further separated by moving electrically by CZE or CGE, by applying a voltage onto said capillary for CZE/CGE.

(g) The case of using the labeled analogue-containing solution, the blood-derived sample-containing solution, and the mobility-changing CFS-containing solution (1) 1) The solution containing the labeled analogue, 2) the solution containing the blood-derived sample including the analyte and 3) the solution containing one or more kinds of the mobility-changing CFSs are introduced and arranged between the LB zone and the TB zone at the inside of the capillary for ITP, as in the step (1) in (g) of [2-6. (2) the separation method 2].

(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex B' including (a) and (b), by contacting, electrophoretically, (a) said analyte, and (b) one or more kinds of the mobility-changing CFSs, and by forming said complex A' including (a') and (b), by contacting, electrophoretically, (a') labeled analogue, and said complex B', and/or by contacting, electrophoretically, (a') said labeled analogue and (b) one or more kinds of the mobility-changing CFSs not involved in formation of said complex B', by ITP, in the presence of the MES ion and/or the glutamate ion, as in the step (2) in (g) of [2-6. (2) the separation method 2].

(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A' and the coexisting materials in the blood-derived sample are further separated by moving electrically by CZE or CGE, by applying a voltage onto said capillary for CZE/CGE.

(h) The case of using the blood-derived sample-containing solution, and (the mobility-changing analogue and the labeled CFS)-containing solution (1) 1) The solution containing the blood-derived sample including the analyte, and 2) the solution containing the mobility-changing analogue and one or more kinds of the labeled CFSs (the solution containing the complex A' of the mobility-changing analogue and the labeled CFSs) are introduced and arranged between the LB zone and the TB zone at the inside of the capillary for ITP, as in the step (1) in (h) of [2-6. (2) the separation method 2].

(2) Then, (i) said complex A" is separated from (ii) the free (c) labeled CFS not involved in formation of said complex A" and/or the complex B" and (iii) the coexisting materials in the blood-derived sample, while concentrating the complex A", at the downstream side of the TB zone, by forming said complex B" including (a) and (c), by contacting, electrophoretically, (a) said analyte and said complex A", by ITP, in the presence of the MES ion and/or the glutamate ion, as in the step (2) in (h) of [2-6. (2) the separation method 2].

(3) The zone including said complex A", the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A" and the coexisting materials in the blood-derived sample are further separated by moving electrically by CZE or CGE, by applying a voltage onto said capillary for CZE/CGE.

(i) The case of using (the blood-derived sample and the labeled CFS)-containing solution, and the solution containing the mobility-changing analogue (1) 1) The solution containing the blood-derived sample including the analyte and one or more kinds of the labeled CFSs (the solution containing the complex B" of the analyte and one or more kinds of the labeled CFSs), and 2) the solution containing the mobility-changing analogue are introduced and arranged between the LB zone and the TB zone at the inside of the capillary for ITP, as in the step (1) in (i) of [2-6. (2) the separation method 2].

(2) Then, (i) said complex A" is separated from (ii) the free (c) labeled CFS not involved in formation of said complex A" and/or the complex B", and (iii) the coexisting materials in the blood-derived sample, while concentrating the complex A", at the downstream side of the TB zone, by forming said complex A" including (a") and (c), by contacting, electrophoretically, (a") mobility-changing analogue, and said complex B", and/or by contacting, electrophoretically, (a") said mobility-changing analogue, and (c) one or more kinds of the labeled CFSs not involved in formation of the complex B", by ITP, in the presence of the MES ion and/or the glutamate ion, as in the step (2) in (i) of [2-6. (2) the separation method 2].

(3) The zone including said complex A", the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A" and the coexisting materials in the blood-derived sample are further separated by moving electrically by CZE or CGE, by applying a voltage onto said capillary for CZE/CGE.

4. The Measurement Method of the Present Invention

By measuring amount of the complex (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs) relevant to the present invention, and amount of the complex relevant to the present invention and the free labeling substance-containing molecule (the labeled CFS, the labeled analogue, and the analyte-labeled CFS complex), not involved in formation of said complex, which were separated by the separation method 1 or the separation method 2 (the step of condensation and separation) of the present invention, by a method corresponding to property of the labeling substances included therein, amount of the analyte existing in the sample can be determined simply and conveniently, and in high sensitivity in a short time.

In addition, in the case where the step of additional separation was carried out in the separation method of the present invention, by measuring amount of the separated complex (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs) relevant to the present invention, by a method corresponding to property of the labeling substances contained in said complex, amount of the analyte present in the sample can be determined simply and conveniently, and in high sensitivity in a short time.

Therefore, the measuring method of the present invention is a method for measuring the analyte, characterized by measuring [C-1] amount of said complex A or amount of the free labeled CFS not involved in formation of said complex A, [C-2] amount of said complex A' or amount of the free labeled CFS not involved in formation of said complex A', or [C-3] amount of said complex A" or amount of the free labeled CFS not involved in formation of said complex A", and/or the amount of the complex B" containing the analyte and the labeled CFS, which were separated by the separation method 1 or the separation method 2 (the step of condensation and separation) of the present invention, to determine amount of the analyte, based the result thereof (the step of measurement); or by measuring amount of complex A, amount of complex A', and amount of complex A", which were separated by carrying out further the step of additional separation, after carrying out the separation method 1 or 2 of the present invention, to determine amount of the analyte, based the result thereof (the step of measurement).

The measuring method of the present invention is one for measuring amount of the complex relevant to the present invention, and amount of the complex relevant to the present invention and the free labeling substance-containing molecule not involved in formation of said complex, separated by the separation method 1 or the separation method 2 (the step of condensation and separation) as above, to determine amount of the analyte, based the result thereof; and is one for measuring amount of complex A, amount of complex A', or amount of complex A", separated by carrying out further the step of additional separation, after carrying out the separation method 1 or 2 of the present invention, to determine amount of the analyte, based the result thereof.

(1) A Step of Measurement

In the step of measurement, the amount of a complex relevant to the present invention, the amount of a complex relevant to the present invention and a free labeling substance-containing molecule not involved in formation of said complex, which are separated, may be measured, for example, by a method corresponding to property of a labeling substance in said complex, or a labeling substance in a free labeling substance-containing molecule not involved in formation of said complex, and based on measurement results of said labeling substance. That is, in a non-competitive method, the amount of a complex A, or the amount of a labeling CFS not involved in formation of said complex A, which are separated, may be determined, for example, by a method corresponding to property of a labeling substance in said complex A, or labeling substance in labeling CFS not involved in formation of said complex, and based on the result of measurement of said labeling substance. In addition, in a competitive method using a labeled analogue, the amount of a complex A' or the amount of a labeled analogue not involved in formation of said complex A', which are separated, may be determined, by a method corresponding to property of a labeling substance in said complex A', or a labeling substance in a labeled analogue not involved in formation of said complex A', and based on the measurement result of said labeling substance. In addition, in a competitive method using a mobility-changing analogue, the amount of a complex A" or the amount of a complex B" and/or the amount of a labeling CFS not involved in formation of said complex A" and complex B", which are separated, may be determined, by a method corresponding to property of a labeling substance in said complex A" or a labeling substance in said complex B" and/or a labeling substance in a labeled CFS not involved in formation of said complex A" and complex B", and based on the measurement result of said labeling substance.

Measurement of the labeling substance may be carried out in accordance with each specified method corresponding to kind of the labeling substance. For example, when said property is enzyme activity, measurement of the labeling substance may be carried out in accordance with a common method such as EIA or a hybridization method [for example, a method described in "Enzyme immunoassay method, protein, nucleic acid, enzyme, separate vol., No. 31, Edited by T. Kitagawa, T. Nambara, A. Tsuji, pages 51 to 63, KYORITSU SHUPPAN Co., Ltd., published on Sep., 10, 1987", etc.]; when said property is fluorescence, measurement of the labeling substance may be carried out in accordance with a common method such as FIA or a hybridization method using measuring instrument such as a fluoro-spectrometer or a confocal laser scanning microscope [a method described in, for example, "Illustration Explanation, Fluorescent antibody, A. Kawao, $1^{st}$ Ed, published by Softscience Co., Ltd., 1983"; "Medical Chemistry Experimental Course, vol. 2, Chemistry of nucleic acid III, M. Saneyoshi, pages 299 to 318, published by TOKYO KAGAKU DOJIN Co., Ltd. on Dec., 15, 1977"]; when said property is luminescence, measurement of the labeling substance may be carried out in accordance with a common method using measuring instrument such as a photon-counter [for example, a method described in "Enzyme immunoassay method, protein, nucleic acid, enzyme, separate vol., No. 31, Edited by T. Kitagawa, T. Nambara, A. Tsuji, pages 252 to 263, KYORITSU SHUPPAN Co., Ltd., published on Sep., 10, 1987"]; further when said property is UV absorption, measurement of the labeling substance may be carried out in accordance with a common method using measuring instrument such as a spectrometer; when said property is color phenomenon, measurement of the labeling substance may be carried out in accordance with a common method using a measuring instrument such as a spectrometer or a microscope; when said property is spin, measurement of the labeling substance may be carried out in accordance with a common method using an electron spin resonance instrument [for example, a method described in "Enzyme immunoassay method, protein, nucleic acid, enzyme, separate vol., No. 31, Edited by T. Kitagawa, T. Nambara, A. Tsuji, pages 264 to 271, KYORITSU SHUPPAN Co., Ltd., published on Sep., 10, 1987", etc.].

In addition, determination of amount of the analyte existing in a sample, based on measured amount of the complex relevant to the present invention, or amount of the free labeling substance-containing molecule not involved in formation of said complex, namely, amount of the labeling substance in the complex relevant to the present invention, or amount of the labeling substance in the free labeling substance-containing molecule not involved in formation of said complex, may be carried out, for example, as follows:

In the non-competitive method, in order to determine amount of the analyte existing in the sample, based on amount of the complex A or amount of the labeled CFS not involved in formation of relevant complex A, which were measured, namely, amount of the labeling substance in the complex A or amount of the labeling substance in the labeled CFS not involved in formation of relevant complex A, obtained as above, amount of the objective analyte can be determined by preparing a calibration curve showing relation between amount of the analyte and amount of the labeling substance in the complex A or the amount of the labeling substance in the labeled CFS not involved in formation of relevant complex A, obtained by carrying out, for example, measurement by a similar method using samples having known concentration of the analyte, and by applying amount of the labeling substance, obtained by carrying out measurement using the sample including the analyte, to this calibration curve.

In a competitive method using a labeled analogue, Determination of the amount of an analyte existing in a sample based on the amount of a complex A' or the amount of a labeled analogue not involved in formation of said complex A', namely the amount of a labeling substance in a complex A' or the amount of a labeling substance in a labeled analogue not involved in formation of said complex A', obtained as above, can be carried out, for example, by preparing a calibration curve showing relation between the amount of an analyte and the amount of a labeling substance in a complex A' or the amount of a labeling substance in a labeled analogue not involved in formation of said complex A', obtained by measurement with a similar method using a sample containing a known concentration of an analyte, and by applying the amount of a labeling substance obtained by measurement of a sample containing an analyte to said calibration curve.

In a competitive method using a mobility-changing analogue, Determination of the amount of an analyte existing in a sample based on the amount of a complex A" or the amount of a complex B" and/or the amount of a labeled CFS not involved in formation of said complex A" and said complex B", namely the amount of a labeling substance in a complex A' or the amount of a labeling substance in a complex B' and/or the amount of a labeling substance in a labeled CFS not involved in formation of said complex A' and complex B', obtained as above, can be carried out, for example, by preparing a calibration curve showing relation between the amount of an analyte and the amount of a labeling substance in a complex A" or the amount of a labeling substance in a complex B" and/or the amount of a labeling substance in a labeled CFS not involved in formation of said complex A" and said complex B", obtained by measurement with a similar method using a sample containing a known concentration of an analyte, and by applying the amount of a labeling substance obtained by measurement of a sample containing an analyte to said calibration curve.

In addition, by the addition of a known concentration of a detectable substance as an internal standard into a sample, and by comparing the amount of said substance added as internal standard, with the amount of a complex relevant to the present invention, or the amount of a free labeling substance-containing molecule not involved in formation of said complex [namely, the amount of a labeling substance in a complex relevant to the present invention or the amount of a labeling substance in a free labeling substance-containing molecule not involved in formation of said complex], the relative amount of an analyte in a sample may be calculated. In addition, such calculation can also be correct an error among electrophoresis equipment (device). Furthermore, by using the mobility of a peak of an internal standard it is possible to also correct the mobility of an objective peak.

Such detectable substances (internal standards) include, for example, peptide, protein, nucleic acid (DNA, RNA), an amino acid, a fluorescent substance, sugar, a sugar chain, etc., labeled with the above described labeling substance; and a fluorescent substance, etc.

In addition, in the present invention, in the case where an enzyme is used as the labeling substance, etc., substrates of said enzyme, or other coupling enzymes may be required to measure activity of said enzyme. In such a case, for example, these substrates or other coupling enzymes may be arranged at the inside of the capillary at the downstream side of the solution including the complex relevant to the present invention, before carrying out at least the step of concentration and separation of the present invention, or before carrying out the step of additional separation. The measuring method of the present invention can be carried out preferably by arranging the solution including these substrates or other coupling enzymes, at the further downstream side of the solution arranged at the most downstream side, among the solution (zone) containing the analyte or the analogue thereof, and the solution (zone) including one or more kinds of the CFSs, in the introduction step of the present invention; or by arranging the solution including these substrates or other coupling enzymes, at the further downstream side of the solution arranged at the most downstream side, among the solution (zone) containing the analyte or the analogue thereof, and the solution (zone) including one or more kinds of the CFSs, in the re-introduction step of the present invention.

In addition, in the case where an intercalator dye is used as the labeling substance, in the introduction step or the re-introduction step of the present invention, said intercalator dye is not required to be introduced and arranged to the inside of the capillary, with the solution containing the analyte or the analogue thereof (the labeled analogue or the mobility-changing analogue), and the solution including one or more kinds of the CFSs (the labeled CFS and/or the mobility-changing CFS), and said intercalator dye may be contained in the LB and/or the TB.

(2) A Specific Measurement Method

A preferable embodiment of the measurement method of the present invention will be shown specifically below.

One embodiment in the separation method 1 will be shown below.

(2-1) The Separation Method 1 Based on the Non-Competitive Method

In this case, separation can be carried out, for example, as in the following [method A] or [method B].

[Method A]:
(1) The solution containing the complex A and the free (c) labeled CFS not involved in formation of relevant complex A is introduced and arranged between the LB zone and the TB zone at the inside of the capillary for ITP, as in the step (1) in the "2-6. (1-1) the non-competitive method".
(2) Then, (i) said complex A is separated from (ii) the free labeled CFS not involved in formation of said complex A and (iii) the coexisting materials in the blood-derived sample, while concentrating said complex A at the downstream side of the TB zone, by ITP, in the presence of the MES ion and/or the glutamate ion, as in the step (2) in the [2-6. (1-1) the non-competitive method].
(3) The zone including said complex A, the zone including the MES ion and/or the glutamate ion, and the zone including the coexisting materials in the blood-derived sample, which are positioned at the downstream side of the TB zone, are introduced between the two LB zones at the inside of the capillary for CZE/CGE.
(4) Said complex A and the coexisting materials in the blood-derived sample are further separated by moving electrically by CZE or CGE, by applying a voltage onto said capillary for CZE/CGE.
(5) Amount of the analyte in the sample is calculated by measuring amount of the labeling substance included in the complex A separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:

The above steps (1) to (4) are carried out by adding a detectable substance having known concentration, as an internal standard, into the solution of (1) of the above [method A], and using the solution including the internal standard. Amount of the analyte in the sample is calculated by measuring amount of the labeling substance included in the complex A separated, by a method corresponding to property (kind) of the labeling substance, and by comparing the measurement result (measurement value) with amount of said substance added as the internal standard.

(2-2) The Separation Method 1 Based on the Competitive Method

The case of using the labeled analogue

In this case, separation can be carried out, for example, as in the following [method A] or [method B].

[Method A]:

(1) The solution containing the complex A' including (a') and (b), and the complex B' including (a) and (b), the free (a') labeled analogue not involved in formation of relevant complex A' is introduced and arranged between the LB zone and the TB zone at the inside of the capillary for ITP, as in the step (1) in the [2-6. (1-2) the competitive method•the case of using the labeled analogue].

(2) Then, (i) said complex A' is separated from (ii) the free labeled analogue not involved in formation of said complex A' and (iii) the coexisting materials in the blood-derived sample, while concentrating said complex A' at the downstream side of the TB zone, by ITP, in the presence of the MES ion and/or the glutamate ion, as in the step (2) in [2-6. (1-2) the competitive method•the case of using the labeled analogue].

(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A' and the coexisting materials in the blood-derived sample are further separated by moving electrically by CZE or CGE, by applying a voltage onto said capillary for CZE/CGE.

(5) Amount of the analyte in the sample is calculated by measuring amount of the labeling substance included in the complex A' separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:

The above steps (1) to (4) are carried out by adding a detectable substance having known concentration, as an internal standard, into the solution of (1) of the above [method A], and using the solution including the internal standard. Amount of the analyte in the sample is calculated by measuring amount of the labeling substance included in the complex A' separated, by a method corresponding to property (kind) of the labeling substance, and by comparing the measurement result (measurement value) with amount of said substance added as the internal standard.

The case of using the mobility-changing analogue

In this case, separation can be carried out, for example, as in the following [method A] or [method B].

[Method A]:

(1) The solution containing the complex A" including (a') and (c), and the complex B" including these (a) and (c), and the free (c) labeled CFS not involved in formation of relevant complex A" is introduced and arranged between the LB zone and the TB zone at the inside of the capillary for ITP, as in the step (1) in the [2-6. (1-2) the competitive method•the case of using the mobility-changing analogue].

(2) Then, (i) said complex A" is separated from (ii) the free labeled CFS not involved in formation of said complex A" and/or said complex B" and (iii) the coexisting materials in the blood-derived sample, while concentrating said complex A" at the downstream side of the TB zone, by ITP, in the presence of the MES ion and/or the glutamate ion, as in the step (2) in [2-6. (1-2) the competitive method•the case of using the mobility-changing analogue].

(3) The zone including said complex A", the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A" and the coexisting materials in the blood-derived sample are further separated by moving electrically by CZE or CGE, by applying a voltage onto said capillary for CZE/CGE.

(5) Amount of the analyte in the sample is calculated by measuring amount of the labeling substance included in the complex A" separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:

The above steps (1) to (4) are carried out by adding a detectable substance having known concentration, as an internal standard, into the solution of (1) of the above [method A], and using the solution including the internal standard. Amount of the analyte in the sample is calculated by measuring amount of the labeling substance included in the complex A" separated, by a method corresponding to property (kind) of the labeling substance, and by comparing the measurement result (measurement value) with amount of said substance added as the internal standard.

One embodiment of the separation method 2 of the present invention will be shown below.

(2-3) The Separation Method 2 Based on the Non-Competitive Method (a) The case of using the blood-derived sample-containing solution, the mobility-changing CFS-containing solution, and the labeled CFS-containing solution In this case, separation can be carried out, for example, as in the following [method A] or [method B].

[Method A]:

(1) 1) The solution containing one or more kinds of the labeled CFSs, 2) the solution containing the blood-derived sample including the analyte and 3) the solution containing one or more kinds of the mobility-changing CFSs are introduced and arranged between the LB zone and the TB zone at the inside of the capillary for ITP, as in the step (1) in (a) of the [2-6. (2) the separation method 2].

(2) Then, (i) said complex A is separated from (ii) the free labeled CFS not involved in formation of said complex A and (iii) the coexisting materials in the blood-derived sample, while concentrating the complex A, at the downstream side of the TB zone, by forming said complex A including (a) to (c), by contacting, electrophoretically, (a) said analyte, (b) one or more kinds of the mobility-changing CFSs and (c) one or more kinds of the labeled CFSs, by ITP, in the presence of the MES ion and/or the glutamate ion, as in the step (2) in (a) of [2-6. (2) the separation method 2].

(3) The zone including said complex A, the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A and the coexisting materials in the blood-derived sample are further separated by moving electrically by CZE or CGE, by applying a voltage onto said capillary for CZE/CGE.

(5) Amount of the analyte in the sample is calculated by measuring amount of the labeling substance included in the complex A separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:

The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A separated, by a method corresponding to property (kind) of the labeling substance, and by comparing the measurement result (measurement value) with amount of said substance added as the internal standard.

(b) The case of using (the blood-derived sample and the labeled CFS)-containing solution, and the mobility-changing CFS-containing solution In this case, separation can be carried out, for example, as in the following [method A] or [method B].

[Method A]:

(1) 1) The solution containing the blood-derived sample including the analyte and one or more kinds of the labeled CFSs (the solution containing the complex of the analyte and the labeled CFSs), and 2) the solution containing one or more kinds of the mobility-changing CFSs are introduced and arranged between the LB zone and the TB zone at the inside of the capillary for ITP, as in the step (1) in (b) of [2-6. (2) the separation method 2].

(2) Then, (i) said complex A is separated from (ii) the free labeled CFS not involved in formation of said complex A and (iii) the coexisting materials in the blood-derived sample, while concentrating the complex A, at the downstream side of the TB zone, by forming said complex A including (a) to (c), by contacting, electrophoretically, (a) said analyte, (b) the complex including one or more kinds of the labeled CFSs and (c) one or more kinds of the mobility-changing CFSs, by ITP, in the presence of the MES ion and/or the glutamate ion, as in the step (2) in (b) of [2-6. (2) the separation method 2].

(3) The zone including said complex A, the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A and the coexisting materials in the blood-derived sample are further separated by moving electrically by CZE or CGE, by applying a voltage onto said capillary for CZE/CGE.

(5) Amount of the analyte in the sample is calculated by measuring amount of the labeling substance included in the complex A separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:

The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A separated, by a method corresponding to property (kind) of the labeling substance, and by comparing the measurement result (measurement value) with amount of said substance added as the internal standard.

(2-6-4) The Separation Method 2 Based on the Competitive Method (c) The case of using (the blood-derived sample and the labeled analogue)-containing solution, and the mobility-changing CFS-containing solution In this case, separation can be carried out, for example, as in the following [method A] or [method B].

[Method A]:

(1) 1) The solution containing the blood-derived sample including the analyte and the labeled analogue, and 2) the solution containing one or more kinds of the mobility-changing CFSs are introduced and arranged between the LB zone and the TB zone at the inside of the capillary for ITP, as in the step (1) in (c) of [2-6. (2) the separation method 2].

(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex A' including (a') and (b), by contacting, electrophoretically, (a') the labeled analogue, and (b) one or more kinds of the mobility-changing CFSs, and by forming said complex B' including (a) and (b), by contacting, electrophoretically, (a) said analyte, and (b) one or more kinds of the mobility-changing CFSs, by ITP, in the presence of the MES ion and/or the glutamate ion, as in the step (2) in (c) of [2-6. (2) the separation method 2].

(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A' and the coexisting materials in the blood-derived sample are further separated by moving electrically by CZE or CGE, by applying a voltage onto said capillary for CZE/CGE.
(5) Amount of the analyte in the sample is calculated by measuring amount of the labeling substance included in the complex A' separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:
The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A' separated, by a method corresponding to property (kind) of the labeling substance, and by comparing the measurement result (measurement value) with amount of said substance added as the internal standard.

(d) The case of using the blood-derived sample-containing solution, and (the labeled analogue and the mobility-changing CFS-containing solution In this case, separation can be carried out, for example, as in the following [method A] or [method B].

[Method A]:
(1) 1) The solution containing the blood-derived sample including the analyte, and 2) the solution containing (a') the labeled analogue and (b) one or more kinds of the mobility-changing CFSs (the solution containing the complex A' of the labeled analogue and one or more kinds of the mobility-changing CFSs) are introduced and arranged between the LB zone and the TB zone at the inside of the capillary for ITP, as in the step (1) in (d) of [2-6. (2) the separation method 2].
(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex B' including (a) and (b), by contacting, electrophoretically, (a) said analyte, and said complex A', by ITP, in the presence of the MES ion and/or the glutamate ion, as in the step (2) in (d) of [2-6. (2) the separation method 2].
(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.
(4) Said complex A' and the coexisting materials in the blood-derived sample are further separated by moving electrically by CZE or CGE, by applying a voltage onto said capillary for CZE/CGE.
(5) Amount of the analyte in the sample is calculated by measuring amount of the labeling substance included in the complex A' separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:
The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A' separated, by a method corresponding to property (kind) of the labeling substance, and by comparing the measurement result (measurement value) with amount of said substance added as the internal standard.

(e) The case of using the labeled analogue-containing solution, and (the blood-derived sample and the mobility-changing CFS)-containing solution In this case, separation can be carried out, for example, as in the following [method A] or [method B].

(1) 1) The solution containing the labeled analogue, and 2) the solution containing the blood-derived sample including the analyte and one or more kinds of the mobility-changing CFSs (the solution including the complex of the analyte and one or more kinds of the mobility-changing CFSs) are introduced and arranged between the LB zone and the TB zone at the inside of the capillary for ITP, as in the step (1) in (e) of [2-6. (2) the separation method 2].
(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex A' including (a') and (b), by contacting, electrophoretically, (a') said labeled analogue, and the complex B', and/or by contacting, electrophoretically, (a') said labeled analogue, and (b) one or more kinds of the mobility-changing CFSs not involved in formation of the complex B', by ITP, in the presence of the MES ion and/or the glutamate ion, as in the step (2) in (e) of [2-6. (2) the separation method 2].
(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.
(4) Said complex A' and the coexisting materials in the blood-derived sample are further separated by moving electrically by CZE or CGE, by applying a voltage onto said capillary for CZE/CGE.
(5) Amount of the analyte in the sample is calculated by measuring amount of the labeling substance included in the complex A' separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:
The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A' separated, by a method corresponding to property (kind) of the labeling substance, and by comparing the measurement result (measurement value) with amount of said substance added as the internal standard.

(f) The case of using the blood-derived sample-containing solution, the labeled analogue-containing solution, and the mobility-changing CFS-containing solution In this case, separation can be carried out, for example, as in the following [method A] or [method B].

[Method A]:
(1) 1) The solution containing the blood-derived sample including the analyte, 2) the solution containing the labeled analogue and 3) the solution containing one or more kinds of the mobility-changing CFSs are introduced and arranged between the LB zone and the TB zone at the inside of the capillary for ITP, as in the step (1) in (f) of [2-6. (2) the separation method 2].
(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex A' including (a') and (b), by contacting, electrophoretically, (a') the labeled analogue, and (b) one or more kinds of the mobility-changing CFSs, and by forming said complex B' including (a) and (b) by contacting, electrophoretically, (a) said analyte, and said complex A', by ITP, in the presence of the MES ion and/or the glutamate ion, as in the step (2) in (f) of [2-6. (2) the separation method 2].
(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.
(4) Said complex A' and the coexisting materials in the blood-derived sample are further separated by moving electrically by CZE or CGE, by applying a voltage onto said capillary for CZE/CGE.
(5) Amount of the analyte in the sample is calculated by measuring amount of the labeling substance included in the complex A' separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:
The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A' separated, by a method corresponding to property (kind) of the labeling substance, and by comparing the measurement result (measurement value) with amount of said substance added as the internal standard.

(g) The case of using the labeled analogue-containing solution, the blood-derived sample-containing solution, and the mobility-changing CFS-containing solution In this case, separation can be carried out, for example, as in the following [method A] or [method B].

[Method A]:
(1) 1) The solution containing the labeled analogue, 2) the solution containing the blood-derived sample including the analyte and 3) the solution containing one or more kinds of the mobility-changing CFSs are introduced and arranged between the LB zone and the TB zone at the inside of the capillary for ITP, as in the step (1) in (g) of [2-6. (2) the separation method 2].
(2) Then, (i) said complex A' is separated from (ii) the free (a') labeled analogue not involved in formation of said complex A' and (iii) the coexisting materials in the blood-derived sample, while concentrating the complex A', at the downstream side of the TB zone, by forming said complex B' including (a) and (b), by contacting, electrophoretically, (a) said analyte, and (b) one or more kinds of the mobility-changing CFSs, and by forming said complex A' including (a') and (b), by contacting, electrophoretically, (a') labeled analogue, and said complex B', and/or by contacting, electrophoretically, (a') said labeled analogue and (b) one or more kinds of the mobility-changing CFSs not involved in formation of said complex B', by ITP, in the presence of the MES ion and/or the glutamate ion, as in the step (2) in (g) of [2-6. (2) the separation method 2].
(3) The zone including said complex A', the zone including the MES ion and/or the glutamate ion, and the zone including the coexisting materials in the blood-derived sample, which are positioned at the downstream side of the TB zone, are introduced between the two LB zones at the inside of the capillary for CZE/CGE.
(4) Said complex A' and the coexisting materials in the blood-derived sample are further separated by moving electrically by CZE or CGE, by applying a voltage onto said capillary for CZE/CGE.
(5) Amount of the analyte in the sample is calculated by measuring amount of the labeling substance included in the complex A' separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:
The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A' separated, by a method corresponding to property (kind) of the labeling substance, and by comparing the measurement result (measurement value) with amount of said substance added as the internal standard.

(h) The case of using the blood-derived sample-containing solution, and (the mobility-changing analogue and the labeled CFS)-containing solution In this case, separation can be carried out, for example, as in the following [method A] or [method B].

[Method A]:
(1) 1) The solution containing the blood-derived sample including the analyte, and 2) the solution containing the mobility-changing analogue and one or more kinds of the labeled CFSs (the solution containing the complex A' of the mobility-changing analogue and the labeled CFSs) are introduced and arranged between the LB zone and the TB zone at the inside of the capillary for ITP, as in the step (1) in (h) of [2-6. (2) the separation method 2].
(2) Then, (i) said complex A" is separated from (ii) the free (c) labeled CFS not involved in formation of said complex A" and/or the complex B" and (iii) the coexisting materials in the blood-derived sample, while concentrating the complex A", at the downstream side of the TB zone, by forming said complex B" including (a) and (c), by contacting, electrophoretically, (a) said analyte, and said complex A", by ITP, in the presence of the MES ion and/or the glutamate ion, as in the step (2) in (h) of [2-6. (2) the separation method 2].

(3) The zone including said complex A", the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A" and the coexisting materials in the blood-derived sample are further separated by moving electrically by CZE or CGE, by applying a voltage onto said capillary for CZE/CGE.

(5) Amount of the analyte in the sample is calculated by measuring amount of the labeling substance included in the complex A" separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:

The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A" separated, by a method corresponding to property (kind) of the labeling substance, and by comparing the measurement result (measurement value) with amount of said substance added as the internal standard.

(i) The case of using (the blood-derived sample and the labeled CFS)-containing solution, and the solution containing the mobility-changing analogue In this case, separation can be carried out, for example, as in the following [method A] or [method B].

[Method A]:

(1) 1) The solution containing the blood-derived sample including the analyte and one or more kinds of the labeled CFSs (the solution containing the complex B" of the analyte and one or more kinds of the labeled CFSs), and 2) the solution containing the mobility-changing analogue are introduced and arranged between the LB zone and the TB zone at the inside of the capillary for ITP, as in the step (1) in (i) of [2-6. (2) the separation method 2].

(2) Then, (i) said complex A" is separated from (ii) the free (c) labeled CFS not involved in formation of said complex A" and/or the complex B", and (iii) the coexisting materials in the blood-derived sample, while concentrating the complex A", at the downstream side of the TB zone, by forming said complex A" including (a") and (c), by contacting, electrophoretically, (a") mobility-changing analogue, and said complex B", and/or by contacting, electrophoretically, (a") said mobility-changing analogue, and (c) one or more kinds of the labeled CFSs not involved in formation of the complex B", by ITP, in the presence of the MES ion and/or the glutamate ion, as in the step (2) in (i) of [2-6. (2) the separation method 2].

(3) The zone including said complex A", the zone including the MES ion and/or the glutamate ion, and the zone including the coexisting materials in the blood-derived sample, which are positioned at the downstream side of the TB zone, are introduced between the two LB zones at the inside of the capillary for CZE/CGE.

(4) Said complex A" and the coexisting materials in the blood-derived sample are further separated by moving electrically by CZE or CGE, by applying a voltage onto said capillary for CZE/CGE.

(5) Amount of the analyte in the sample is calculated by measuring amount of the labeling substance included in the complex A" separated, by a method in response to property (kind) of the labeling substance, and by applying the measurement result (measurement value) to a calibration curve showing relation between amount of the analyte and amount of the labeling substance, obtained by carrying out measurement by a similar method, using samples having known concentration of the analyte.

[Method B]:

The above steps (1) to (4) are carried out by adding a detectable substance having known concentration, as an internal standard, into the at least one kind of solution of (1) of the above [method A], and using the solution including the internal standard. Amount of the analyte in the sample is calculated by measuring amount of the labeling substance included in the complex A" separated, by a method corresponding to property (kind) of the labeling substance, and by comparing the measurement result (measurement value) with amount of said substance added as the internal standard.

The measurement method of the present invention may be carried out according to the above methods known themselves, except the utilization of the separation method of the present invention, and reagents etc. to be used may be selected, as appropriate, according to these methods known themselves.

5. Characteristics of the Present Invention

The present invention has characteristics that separation of the complex (the complex A including the analyte, one or more kinds of mobility-changing CFSs and one or more kinds of the labeled CFSs, the complex A' including the labeled analogue and one or more kinds of the mobility-changing CFSs, and the complex A" including the mobility-changing analog and one or more kinds of the labeled CFSs) relevant to the present invention and the coexisting materials in the blood-derived sample can be carried out efficiently by carrying out ITP, in the presence of the MES ion and/or the glutamate ion.

However, a problem itself has not been known at all up to now, that, in the case of separating the complex and the coexisting materials in the blood-derived sample while concentrating said complex including the analyte in said blood-derived sample or the analogue thereof, the CFS, the mobility-changing substances and the labelling substances, by ITP using the blood-derived sample as a sample, said complex and the coexisting materials (in particular, bilirubin, a metabolite of bilirubin, or a complex of bilirubin and protein, etc.) exhibiting fluorescence in the blood-derived sample have the same degree of electrophoretic mobility as that of the objective complex relevant to the present invention (in other words, it moves to the vicinity of moving time of said complex by ITP, and the peak of the coexisting materials appears at the vicinity of the peak of said complex in an electropherogram by ITP), which thus deteriorates separation precision.

And also, it has not been known at all up to now, that only the MES ion and/or the glutamate ion are capable of separating said complex and the coexisting materials in the blood-derived sample (in other words, in such a case, only the MES ion and/or the glutamate ion can be the spacer molecule between said complex and the coexisting materials in the blood-derived sample).

In particular, it has been recognized for the first time that bilirubin, a metabolite thereof, or a complex of bilirubin and protein, give adverse effect on analysis as above as the coexisting materials, and it has been found for the first time that the separation method of the present invention is particularly effective in separating the coexisting materials (in particular, bilirubin, a metabolite thereof, or a complex of bilirubin and protein, etc.) and the complex relevant to the present invention, namely, by the separation method of the present invention, the coexisting materials (in particular, bilirubin, a metabolite thereof, or a complex of bilirubin and protei, etc.) in the blood-derived sample, and the complex relevant to the present invention can be separated.

In addition, it has not been known at all up to now, that by controlling electrophoretic mobility of the complex using the mobility-changing CFS (the mobility-changing substance), as a result, there may be the case where electrophoretic mobility of the complex relevant to the present invention becomes the same degree as that of the coexisting materials (in particular, bilirubin) in the blood-derived sample [electrophoretic mobility of the complex relevant to the present invention moves to the vicinity of moving time of the coexisting materials (in particular, bilirubin, a metabolite thereof, or a complex of bilirubin and protein, etc.) by ITP; the peak of the complex relevant to the present invention appears at the vicinity of the peak of the coexisting materials (in particular, bilirubin) in an electropherogram by ITP; and peaks of both overlap], and in such a case, also a problem itself of deterioration of separation precision.

And also, it has not been known at all that the separation method of the present invention is useful in such a case, in other words, it is particularly useful in the case of using one which is capable of changing electrophoretic mobility of the complex relevant to the present invention to the vicinity of that of the coexisting materials (in particular, bilirubin, a metabolite thereof, or a complex of bilirubin and protein etc.) in the blood-derived sample, as the mobility-changing CFS (the mobility-changing substance).

In particular, it has been found for the first time that the separation method of the present invention is particularly effective, in the case where the mobility-changing substance is a nucleic acid chain, in using the nucleic acid chain having a length of usually from 50 by to 2000 bp, preferably from 100 by to 1000 bp, more preferably from 120 by to 700 bp, and particularly preferably from 150 by to 500 bp.

Explanation will be given below in detail on the present invention with reference to Examples and Comparative Examples, however, the scope of the present invention should not be limited thereto.

EXAMPLES

Example 1

Separation of Serum-Coexisting Materials and AFP in ITP)

[Analyte (Antigen)]
α-fetoprotein (AFP) (manufactured by Wako Pure Chemical Industries, Ltd.)
[A Mobility-Changing Binding Substance (a DNA Labeled Antibody)]
An anti AFP antibody Fab' fragment bound with DNA was prepared according to the procedure shown in FIG. 1.

That is, a 250 by DNA fragment introduced with an $NH_2$ group at the 5' terminal by a common method, was purified firstly, and then, the $NH_2$ group introduced to this DNA fragment was reacted with sulfosuccinimidyl 4-(p-maleidophenyl)butyrate (sulfo-SMPB) linker (linker having a succinimide group and a maleimido group; manufactured by Pierce Chemical Co., Ltd.), by a common method, followed by carrying out gel filtration treatment and removing un-reacted linkers to obtain the 250 by DNA fragment bound with the linker. The resultant 250 by DNA fragment bound with the linker was reacted with an anti AFP antibody WA1 Fab' fragment, prepared in advance according to a common method, using the anti AFP antibody WA1 (manufactured by Wako Pure Chemical Industries, Ltd.). The resultant reactants were each purified using a DEAE column to prepare an anti AFP antibody WA1 Fab' fragment bound with the 250 by DNA fragment (the 250 by DNA labeled antibody).

[A Label Binding Substance (a Fluorescence Labeled Antibody)]
An anti-AFP antibody WA2 (manufactured by Wako Pure Chemical Industries, Ltd.) which recognizes an epitope of AFP different from a WA1 antibody, was treated by a common method to prepare an anti-AFP antibody WA2 Fab' fragment, and a fluorescent substance HiLyte 647 (manufactured by AnaSpec Co., Ltd.) was introduced to an amino group of said fragment by a common method to prepare an HiLyte 647 labeled anti-AFP antibody WA2 Fab' fragment (a fluorescence labeled antibody).

[A Capillary Chip]
The capillary chip having a layout shown in FIG. 2 was prepared according to a method described in "Technology and application of microchemistry chip", T. Kitamori et al., published in 2004 (Maruzen Co., Ltd.) as follows:

That is, a photo resist film was formed on Si film which was formed on a quartz substrate. This photo resist was exposed using a mask having a capillary design (layout) shown in FIG. 2 and developed. Si at the part, where a photo resist was removed by development, was removed by sputtering, and then wet etching was carried out using a solution of hydrogen fluoride to produce a capillary channel groove (capillary) at the quartz substrate. After removing a photo resist and a Si film remained on the quartz substrate, said quartz substrate and a cover plate having a hole (well) for a fluid reservoir were adhered together by an HF bonding technique to produce a capillary chip.

In this connection, in FIG. 2, TB shows a well for introducing the trailing buffer, LB1 and LB2 show wells for introducing the leading buffer, S shows a well for introducing an electrophoresis sample, R1 shows a well for introducing a reagent solution (a solution containing a 250 by DNA labeled antibody), and W1, W2 and W3 show represent a well for drain, respectively.

[Electrophoresis]
(1) An Electrophoresis Sample
[An electrophoresis Sample A]
As a specimen, 1 μL of PBS [50 mM phosphate buffer (pH6) including 0.1% bovine serum albumin (BSA) and 150 mM NaCl]; 1 μL of 1 μM fluorescence labeled antibody; and 8 μL of sample buffer [75 mM Tris-HCl (pH7.5) containing 0.6% (w/v) polydimethyl acrylamide (pDMA), 3% (w/v) glycerol, 75 mM NaCl, 0.01% BSA; not including the MES ion] were mixed in a 0.5 mL tube to prepare 10 μL of mixed solution. The mixed solution was stood still on ice for about 30 minutes. In this connection, final concentration of the fluorescence labeled antibody was 100 nM.

The resultant mixed solution was used as the electrophoresis sample A.

[An electrophoresis Sample B]
As a specimen, 1 μL of PBS including about 2 nM AFP (PBS added with AFP), 1 μL of 1 μM fluorescence labeled antibody and 8 μL of sample buffer [75 mM Tris-HCl (pH7.5) containing 0.6% (w/v) pDMA, 3% (w/v) glycerol, 75 mM NaCl, 0.01% BSA; not including the MES ion] were mixed in a 0.5 mL tube to prepare 10 μL of reaction solution. The reaction solution was stood still on ice to be subjected to an antigen-antibody reaction for about 30 minutes to form an immune complex of fluorescence labeled antibody-AFP. In this connection, final concentration of the fluorescence labeled antibody was 100 nM.

The resultant immune complex-containing reaction solution was used as the electrophoresis sample B.

[An Electrophoresis Sample C]

As a specimen, 1 μL of serum including about 30 μM AFP (serum inhered with AFP), 1 μL of 1 μM fluorescence labeled antibody and 8 μL of sample buffer [75 mM Tris-HCl (pH7.5) containing 0.6% (w/v) pDMA, 3% (w/v) glycerol, 75 mM NaCl, 0.01% BSA; not including the MES ion] were mixed in a 0.5 mL tube to prepare 10 μL of reaction solution. The reaction solution was stood still on ice to be subjected to an antigen-antibody reaction for about 30 minutes to form an immune complex of fluorescence labeled antibody-AFP. In this connection, final concentration of the fluorescence labeled antibody was 100 nM.

The resultant immune complex-containing reaction solution was used as the electrophoresis sample C.

[An Electrophoresis Sample D]

As a specimen, 1 μL of serum including 100 μM AFP (serum added with AFP), 1 μL of 1 μM fluorescence labeled antibody and 8 μL of sample buffer [75 mM Tris-HCl (pH7.5) containing 0.6% (w/v) pDMA, 3% (w/v) glycerol, 75 mM NaCl, 0.01% BSA; not including the MES ion] were mixed in a 0.5 mL tube to prepare 10 μL of reaction solution. The reaction solution was stood still on ice to be subjected to an antigen-antibody reaction for about 30 minutes to form an immune complex of fluorescence labeled antibody-AFP. In this connection, final concentration of the fluorescence labeled antibody was 100 nM.

The resultant immune complex-containing reaction solution was used as the electrophoresis sample D.

[An Electrophoresis Sample E]

As a specimen, 1 μL of serum including 100 μM AFP and 20 mg/dL bilirubin (serum added with AFP and bilirubin), 1 μL of 1 μM fluorescence labeled antibody and 8 μL of sample buffer [75 mM Tris-HCl (pH7.5) containing 0.6% (w/v) pDMA, 3% (w/v) glycerol, 75 mM NaCl, 0.01% BSA; not including the MES ion] were mixed in a 0.5 mL tube to prepare 10 μL of reaction solution. The reaction solution was stood still on ice to be subjected to an antigen-antibody reaction for about 30 minutes to form an immune complex of fluorescence labeled antibody-AFP. In this connection, final concentration of the fluorescence labeled antibody was 100 nM.

The resultant immune complex-containing reaction solution was used as the electrophoresis sample E.

[An Electrophoresis Sample F]

As a specimen, 1 μL of serum including about 30 μM AFP (serum inhered with AFP), 1 μL of 1 μM fluorescence labeled antibody and 8 μL of sample buffer [75 mM Tris-HCl (pH7.5) containing 0.6% (w/v) pDMA, 3% (w/v) glycerol, 75 mM NaCl, 0.01% BSA] containing 3.6 mM MES (2-(N-morpholino) ethane sulfonate-mono-hydrate: manufactured by Dojindo Laboratories) were mixed in a 0.5 mL tube to prepare 10 μL of reaction solution. The reaction solution was stood still on ice to be subjected to an antigen-antibody reaction for about 30 minutes to form an immune complex of fluorescence labeled antibody-AFP. In this connection, final concentration of the fluorescence labeled antibody was 100 nM.

The resultant immune complex-containing reaction solution was used as the electrophoresis sample F.

[An Electrophoresis Sample G]

As a specimen, 1 μL of serum including 100 μM AFP and 20 mg/dL bilirubin (serum added with AFP and bilirubin), 1 μL of 1 μM fluorescence labeled antibody, and 8 μL of sample buffer [75 mM Tris-HCl (pH7.5) containing 0.6% (w/v) polydimethyl acrylamide (pDMA), 3% (w/v) glycerol, 75 mM NaCl, 0.01% BSA] containing 3.6 mM MES were mixed in a 0.5 mL tube to prepare 10 μL of reaction solution. The reaction solution was stood still on ice to be subjected to an antigen-antibody reaction for about 30 minutes to form an immune complex of fluorescence labeled antibody-AFP. In this connection, final concentration of the fluorescence labeled antibody was 100 nM.

The resultant immune complex-containing reaction solution was used as the electrophoresis sample G.

(2) A Reagent Solution (a 250 by DNA Labeled Antibody-Containing Solution)

A leading buffer [75 mM Tris-HCl (pH 7.5) containing 0.6% (w/v) pDMA, 3% (w/v) glycerol, 75 mM NaCl, 0.01% BSA] containing 100 nM 250 by DNA labeled antibody was used as the reagent solution.

(3) Procedures of Electrophoresis a) Introduction of the Electrophoresis Sample and the Reagent Solution Into the Swell (a well for introducing the electrophoresis sample) shown in FIG. 2, 10 μL of the electrophoresis sample was delivered by drops, 10 μL of the reagent solution was delivered by drops into the R1 well (a well for introducing the reagent solution), 10 μL, of the leading buffer was delivered by drops into the LB1 and LB2 wells, and 10 μL, of the trailing buffer [75 mM Tris containing 0.6% (w/v) pDMA, 3% (w/v) glycerol, 0.01% BSA, 125 mM 2-[4-(2-hydroxyethyl)-1-piperazinyl]ethane sulfonic acid (HEPES)] was delivered by drops into the TB well, and by application of a pressure of −5 psi for 30 seconds between the W1 (a well for drain)—the W2 (a well for drain)—the W3 (a well for drain), the electrophoresis sample, the reagent solution, the leading buffer, and the trailing buffer were introduced into the channel. Arrangement relation of the electrophoresis sample and the reagent solution in the capillary was schematically shown in FIG. 3. In this connection, in FIG. 3, a shaded area shows an arrangement part of the electrophoresis sample, and a dotted area shows an arrangement part of the reagent solution.

b) ITP (Reaction, Concentration and Separation)•Detection

By applying a voltage of 3000 V between the TB well and the LB1 well of FIG. 3, and making the 250 by DNA labeled antibody in the reagent solution contacted with [the fluorescence labeling antibody-AFP] immune complex in the electrophoresis sample, at 30° C., an immune complex of a fluorescence labeled antibody-AFP-250 bp DNA labeled antibody was formed, which was concentrated.

In this connection, reaction time was about 100 seconds (as a time for the 250 by DNA labeled antibody to pass through a zone of the electrophoresis sample).

Further, ITP was carried out till a peak of the immune complex of the fluorescence labeled antibody-AFP-250 bp DNA labeled antibody was detected at a detection part (the capillary part at 2 cm apart from a crossing part of an LB2 channel).

In this connection, the detection was carried out by measuring fluorescence intensity at the capillary part at 2 cm apart from the crossing part of an LB2 channel, by 635 nm laser excitation, with time, using a fluorescence microscope (BX-50; manufactured by KS Olympus Co., Ltd.).

In Table 1, combinations and compositions etc. of the electrophoresis samples and the reagent solution subjected to reaction are shown.

TABLE 1

| | | Electrophoresis samples | | | | | | Reagent solution |
|---|---|---|---|---|---|---|---|---|
| Exp. No. | Samp. No. | Specimen | | | | Fluorecsent antibody | MES | DNA antibody |
| | | Serum | PBS | AFP | Bilirubin | | | |
| 1-1 | A | — | 1 μL | — | — | 100 nM | — | 100 nM |
| 1-2 | B | — | 1 μL | about 2 nM (added) | — | 100 nM | — | 100 nM |
| 1-3 | C | 1 μL | — | about 30 pM (inherent) | — | 100 nM | — | 100 nM |
| 1-4 | D | 1 μL | — | 100 pM (added) | — | 100 nM | — | 100 nM |
| 1-5 | E | 1 μL | — | 100 pM (added) | 20 mg/dL (added) | 100 nM | — | 100 nM |
| 1-6 | F | 1 μL | — | about 30 pM (inherent) | — | 100 nM | 3.6 mM | 100 nM |
| 1-7 | G | 1 μL | — | 100 pM (added) | 20 mg/dL (added) | 100 nM | 3.6 mM | 100 nM |

[Results]

FIG. 4 shows an electrophoresis image (an electropherogram) in the case of using an electrophoresis sample A (a serum free sample) [Experiment No. 1-1], and an electrophoresis image (an electropherogram) in the case of using an electrophoresis sample B (a sample added with AFP) [Experiment No. 1-2].

Figure 5:
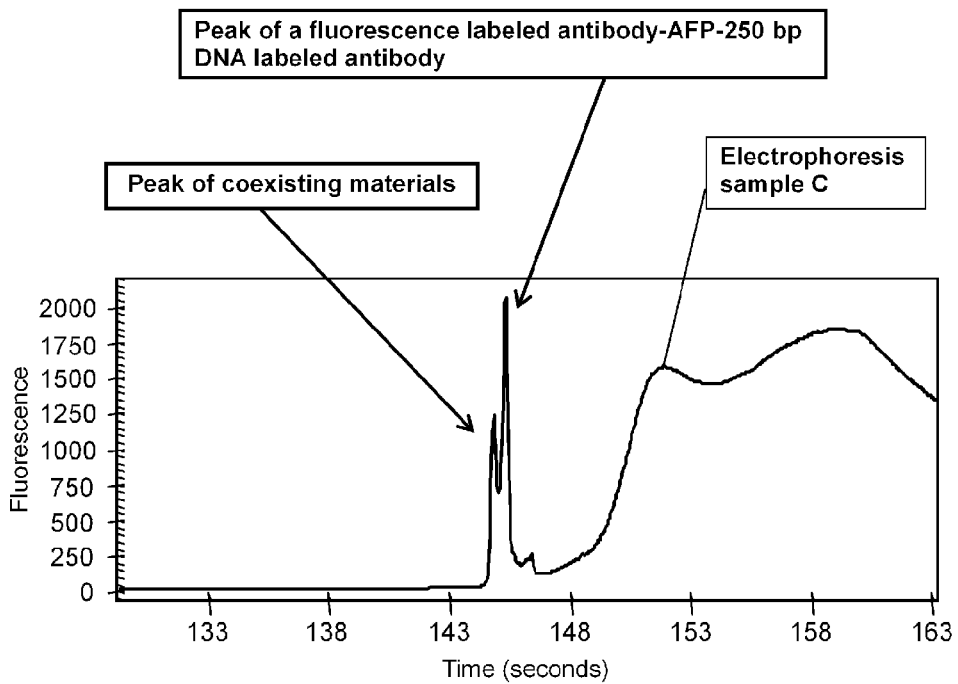
FIG. 5 shows an electropherogram in the case of using an electrophoresis sample C (a sample added with serum) [Experiment No. 1-3] (ITP), obtained in Example 1.

FIG. 5 shows an electrophoresis image (an electropherogram) in the case of using an electrophoresis sample C (a sample added with serum) [Experiment No. 1-3].

Figure 6:
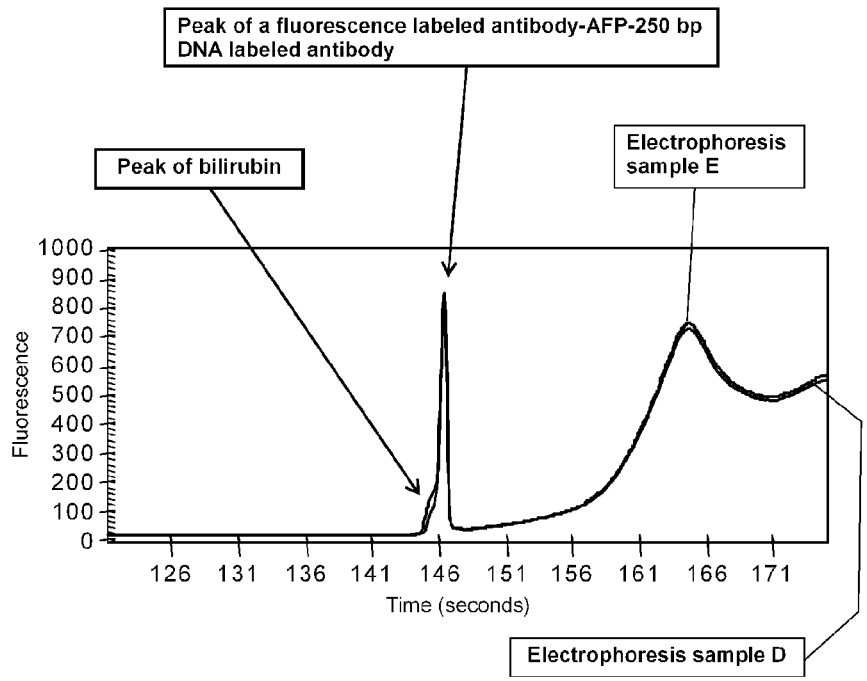
FIG. 6 shows an electropherogram in the case of using an electrophoresis sample E (a (serum and bilirubin)-containing sample) [Experiment No. 1-5] (ITP), and in the case of using an electrophoresis sample D (a sample added with serum: bilirubin free) [Experiment No. 1-4] (ITP), obtained in Example 1.

FIG. 6 shows an electrophoresis image (an electropherogram) in the case of using an electrophoresis sample E (a (serum and bilirubin)-containing sample) [Experiment No. 1-5], and an electrophoresis image (an electropherogram) in the case of using an electrophoresis sample D (a serum-containing sample: bilirubin free) [Experiment No. 1-4].

Figure 7:
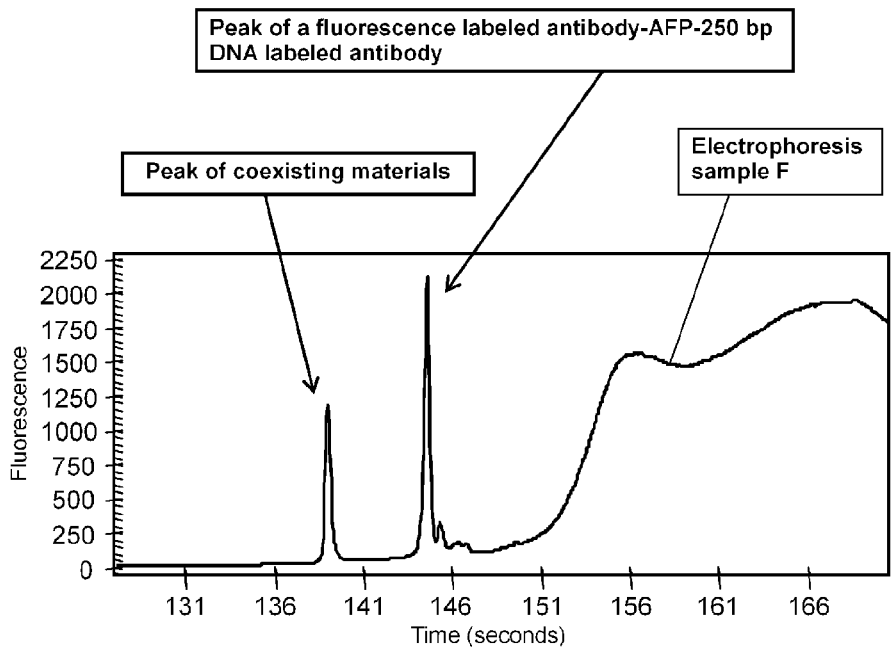
FIG. 7 shows an electropherogram in the case of using an electrophoresis sample F (a (serum and the MES ion)-containing sample) [Experiment No. 1-6] (ITP), obtained in Example 1.

FIG. 7 shows an electrophoresis image (an electropherogram) in the case of using an electrophoresis sample F (a (serum and the MES ion)-containing sample) [Experiment No. 1-6].

Figure 8:
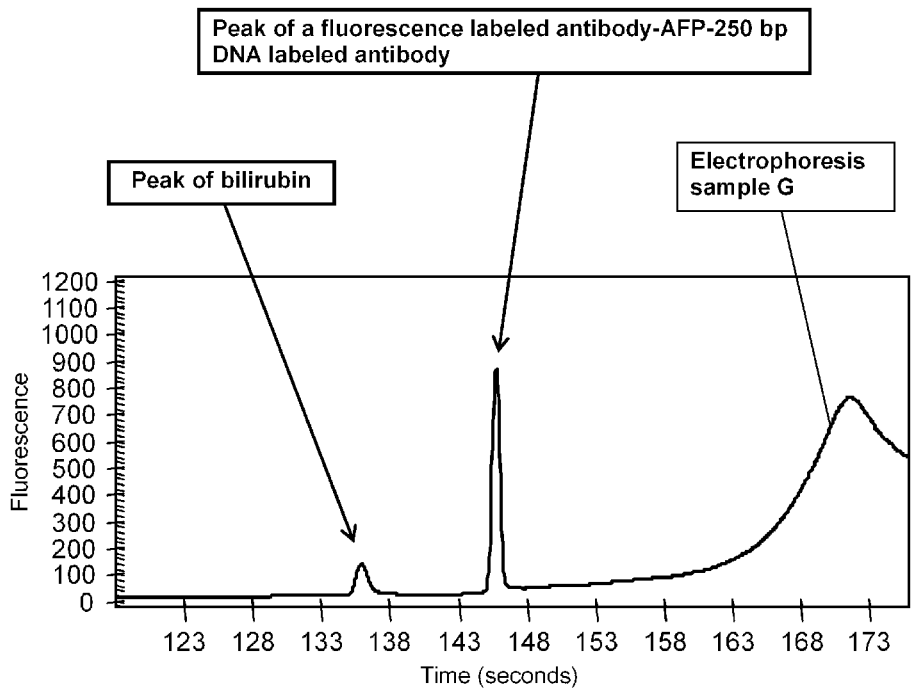
FIG. 8 shows an electropherogram in the case of using an electrophoresis sample G (a (serum, bilirubin and the MES ion)-containing sample) [Experiment No. 1-7] (ITP), obtained in Example 1.

FIG. 8 shows an electrophoresis image (an electropherogram) in the case of using an electrophoresis sample G (a (serum, bilirubin and the MES ion)-containing sample) [Experiment No. 1-7].

In this connection, in FIG. 4 to FIG. 8, the Y axis and the X axis represent peak intensity and retention time, respectively.

From the results of FIG. 4, it is understood that a peak at the vicinity of 146 seconds is a peak of the objective immune complex of the fluorescence labeled antibody-AFP-250 bp DNA labeled antibody. That is, in the case of using the electrophoresis sample A (the serum free sample) [experiment No. 1-1], because the DNA labeled antibody is not present, said immune complex is not formed (the peak does not appear). On the other hand, in the case of using the electrophoresis sample B (the sample added with AFP) [experiment No. 1-2], said immune complex is formed, and the peak appears at the vicinity of 146 seconds. In this connection, the peak at the vicinity of 146 seconds, in the case of using the electrophoresis sample A (the serum free sample) [experiment No. 1-1], is considered to be a peak of a reagent noise (a peak of a not-binding labeling substance).

From the result of the case where the electrophoresis sample B (the sample not containing serum) [experiment No. 1-2] in FIG. 4 was used, and from the result of the case where the electrophoresis sample C (the sample added with serum) [experiment No. 1-3] in FIG. 5 was used, it is found that a peak (a peak at the vicinity of 144.5 seconds) derived from the coexisting materials in the serum appears before the peak (a peak at the vicinity of 145 seconds) of the objective immune complex of the fluorescence labeled antibody-AFP-250 bp DNA labeled antibody. In addition, from the result of the case where the electrophoresis sample E (the (serum and bilirubin)-containing sample) [experiment No. 1-5] in FIG. 6 was used, and from the result of the case where the electrophoresis sample D (the serum-containing sample bilirubin free) [experiment No. 1-4] in FIG. 6 was used, it is found that in the case of using the serum sample added with bilirubin, the peak at the vicinity of 145 seconds increases, as compared with the case of using the serum sample not added with bilirubin. From this, it is found that in the peak (the peak at the vicinity of 144.5 seconds) derived from the coexisting materials in serum in FIG. 5, the peak derived from at least bilirubin is included.

From the result of the case where the electrophoresis sample C (the sample not including the MES ion) [experiment No. 1-3] in FIG. 5 was used, and from the result of the case where the electrophoresis sample F (the MES ion-containing sample) [experiment No. 1-6] in FIG. 7 was used, it is found that separation of the peak (the peak at the vicinity of 145 seconds) of the immune complex and the peak (the peak at the vicinity of 144.5 seconds) derived from the coexisting materials is insufficient, in the case where the MES ion is not present, whereas, the peak (the peak at the vicinity of 145 seconds) of the immune complex, and the peak (the peak at the vicinity of 139 seconds) derived from the coexisting materials are sufficiently separated by making the MES ion existed.

In addition, similarly, from the result of the case where the electrophoresis sample E (the (serum and bilirubin)-containing sample) [experiment No. 1-5] in FIG. 6 was used, and from the result of the case where the electrophoresis sample G (the (serum, bilirubin and the MES ion)-containing sample) [experiment No. 1-7] in FIG. 8 was used, it is found that the peak (the peak at the vicinity of 146 seconds) of the immune complex and the peak (the peak at the vicinity of 145 seconds) derived from bilirubin are little separated, in the case where the MES ion is not present, whereas, the peak (the peak at the vicinity of 146 seconds) of the immune complex, and the peak (the peak at the vicinity of 136 seconds) derived from bilirubin are sufficiently separated by making the MES ion existed.

As is clear from the above results, it is found that, by carrying out ITP, in the presence of the MES ion, the objective complex and the coexisting materials can be separated well.

Example 2

Separation of the Serum Coexisting Materials and AFP in ITP-CZE

[An Analyte (an Antigen)]
The same one as in Example 1 was used.
[A Mobility-Changing Binding Substance (a DNA Labeled Antibody)]
The same one as in Example 1 was used.
[A Label Binding Substance (a Fluorescence Labeled Antibody)]
The same one as in Example 1 was used.
[A Microchip]
The same one as in Example 1 was used.
[Electrophoresis]
(1) An Electrophoresis Sample
The same electrophoresis samples A to F as in Example 1 were used.
(2) Reagent Solution (a Solution Including the 250 by DNA Labeled Antibody)
The same one as in Example 1 was used.
(3) Procedures of Electrophoresis
a) Introduction of the Electrophoresis Sample and the Reagent Solution
It was carried out similarly as in Example 1.
b) ITP (Reaction, Concentration and Separation)
By applying a voltage of 3000 V between the TB well and the LB1 well of FIG. 3, and making the 250 by DNA labeled antibody in the reagent solution contacted with [the fluorescence labeling antibody-AFP] immune complex in the electrophoresis sample, at 30° C., an immune complex of a fluorescence labeled antibody-AFP-250 bp DNA labeled antibody was formed, which was concentrated.

In this connection, reaction time was about 100 seconds (as a time for the 250 by DNA labeled antibody to pass through a zone of the electrophoresis sample).
c) CZE (Separation and Detection)
Separation and detection of the immune complex were carried out by applying a voltage of 1300 V onto the LB2 well and 300 V onto the LB1 well for 60 seconds, when said immune complex of the fluorescence labeled antibody-AFP-250 bp DNA labeled antibody passed through a crossing part of the LB2 channel and the main channel.

In this connection, the detection was carried out by measuring fluorescence intensity at the capillary part at 2 cm apart from the crossing part of an LB2 channel, by 635 nm laser excitation, with time, using a fluorescence microscope (BX-50; manufactured by KS Olympus Co., Ltd.).

In Table 2, combinations and compositions of the electrophoresis samples and the reagent solution subjected to reaction are shown.

TABLE 2

| Exp. No. | Samp. No. | Specimen Serum | PBS | AFP | Bilirubin | Fluorecsent antibody | MES | Reagent solution DNA antibody |
|---|---|---|---|---|---|---|---|---|
| 2-1 | A | — | 1 µL | — | — | 100 nM | — | 100 nM |
| 2-2 | B | — | 1 µL | about 2 nM (added) | — | 100 nM | — | 100 nM |
| 2-3 | C | 1 µL | — | about 30 pM (inherent) | — | 100 nM | — | 100 nM |
| 2-4 | D | 1 µL | — | 100 pM (added) | — | 100 nM | — | 100 nM |
| 2-5 | E | 1 µL | — | 100 pM (added) | 20 mg/dL (added) | 100 nM | — | 100 nM |
| 2-6 | F | 1 µL | — | about 30 pM (inherent) | — | 100 nM | 3.6 mM | 100 nM |
| 2-7 | G | 1 µL | — | 100 pM (added) | 20 mg/dL (added) | 100 nM | 3.6 mM | 100 nM |

Figure 9:
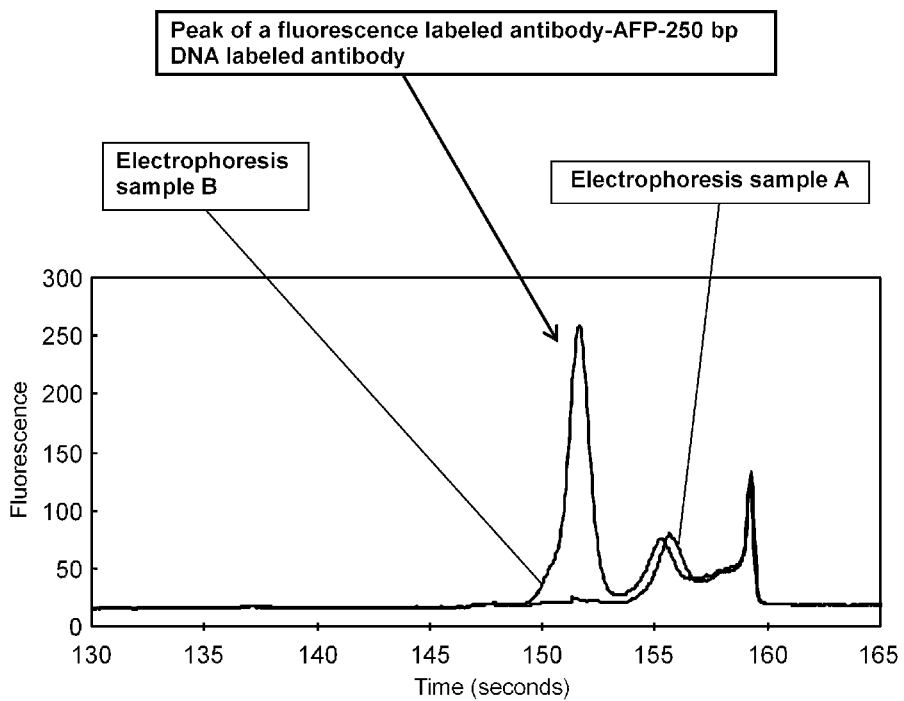
FIG. 9 shows an electropherogram in the case of using an electrophoresis sample A (a serum free sample) [Experiment No. 2-1] (ITP-CE), and in the case of using an electrophoresis sample B (a sample added with AFP) [Experiment No. 2-2] (ITP-CE), obtained in Example 2.

[Results]
FIG. 9 shows an electrophoresis image (an electropherogram) in the case of using an electrophoresis sample A (a serum free sample) [Experiment No. 2-1], and an electrophoresis image (an electropherogram) in the case of using an electrophoresis sample B (a sample added with AFP) [Experiment No. 2-2].

Figure 10:
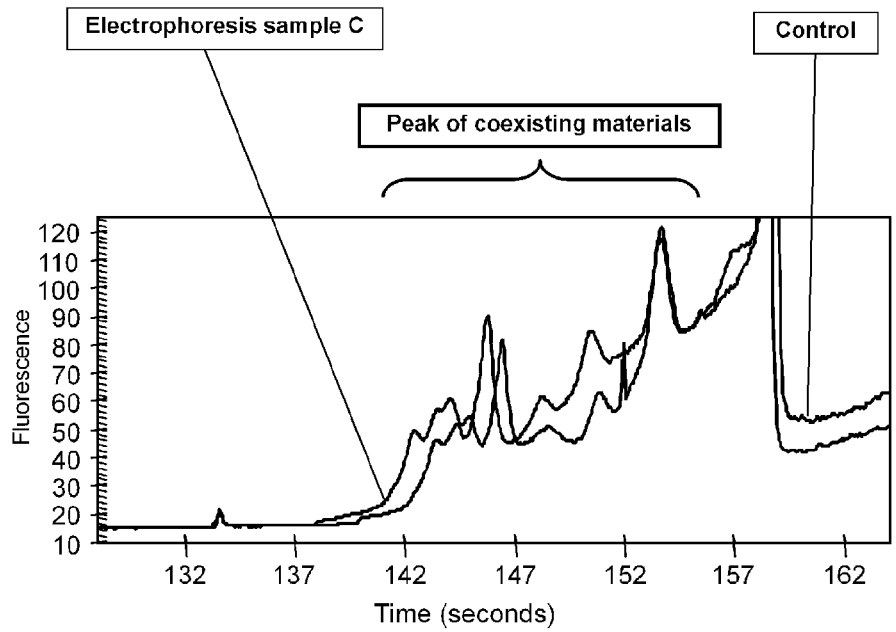
FIG. 10 shows an electropherogram in the case of using an electrophoresis sample C (a sample added with serum) [Experiment No. 2-3] (ITP-CE), obtained in Example 2.

FIG. 10 shows an electrophoresis image (an electropherogram) in the case of using an electrophoresis sample C (a sample added with serum) [Experiment No. 2-3]. In this connection, the case of not using the reagent solution (a DNA labeled antibody-containing solution) (result using only the electrophoresis sample) is also shown as a control.

Figure 11:
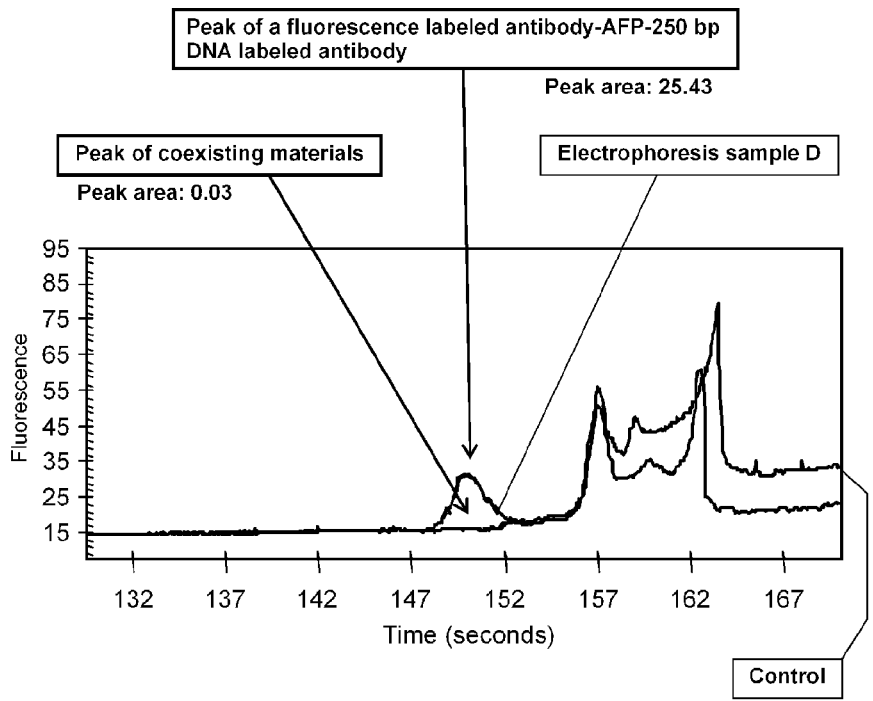
FIG. 11 shows an electropherogram in the case of using an electrophoresis sample D (a sample added with serum) [Experiment No. 2-4] (ITP-CE), obtained in Example 2.

FIG. 11 shows an electrophoresis image (an electropherogram) in the case of using an electrophoresis sample D (a sample added with serum) [Experiment No. 2-4]. In this connection, the case of not using the reagent solution (a DNA labeled antibody-containing solution) (result using only the electrophoresis sample) is also shown as a control. In addition, peak area in the Figure was determined by a common method.

Figure 12:
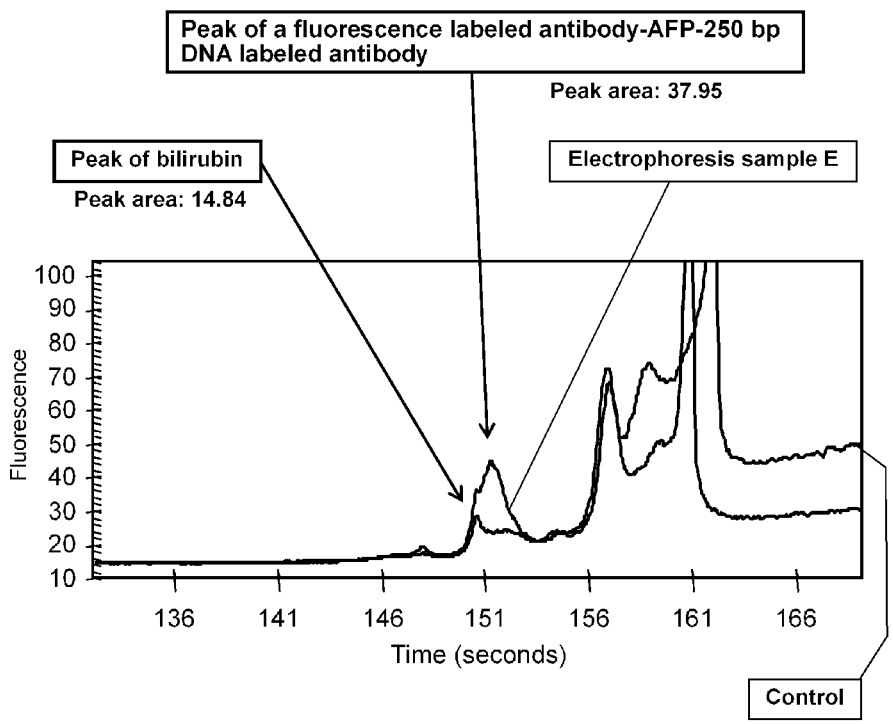
FIG. 12 shows an electropherogram in the case of using an electrophoresis sample E (a (serum and bilirubin)-containing sample) [Experiment No. 2-5] (ITP-CE), obtained in Example 2.

FIG. 12 shows an electrophoresis image (an electropherogram) in the case of using an electrophoresis sample E (a (serum and bilirubin)-containing sample) [Experiment No. 2-5]. In this connection, the case of not using the reagent solution (a DNA labeled antibody-containing solution) (result using only the electrophoresis sample) is also shown as a control. In addition, peak area in the Figure was determined by a common method.

Figure 13:
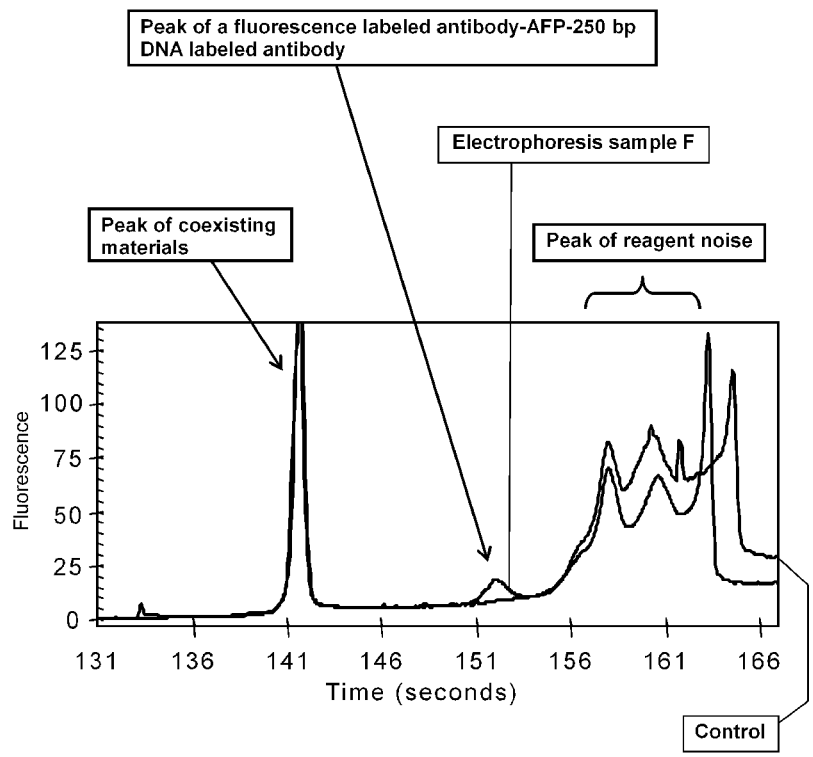
FIG. 13 shows an electropherogram in the case of using an electrophoresis sample F (a (serum and the MES ion)-containing sample) [Experiment No. 2-6] (ITP-CE), obtained in Example 2.

FIG. 13 shows an electrophoresis image (an electropherogram) in the case of using an electrophoresis sample F (a (serum and the MES ion)-containing sample) [Experiment No. 2-6]. In this connection, the case of not using the reagent solution (a DNA labeled antibody-containing solution) (result using only the electrophoresis sample) is also shown as a control.

Figure 14:
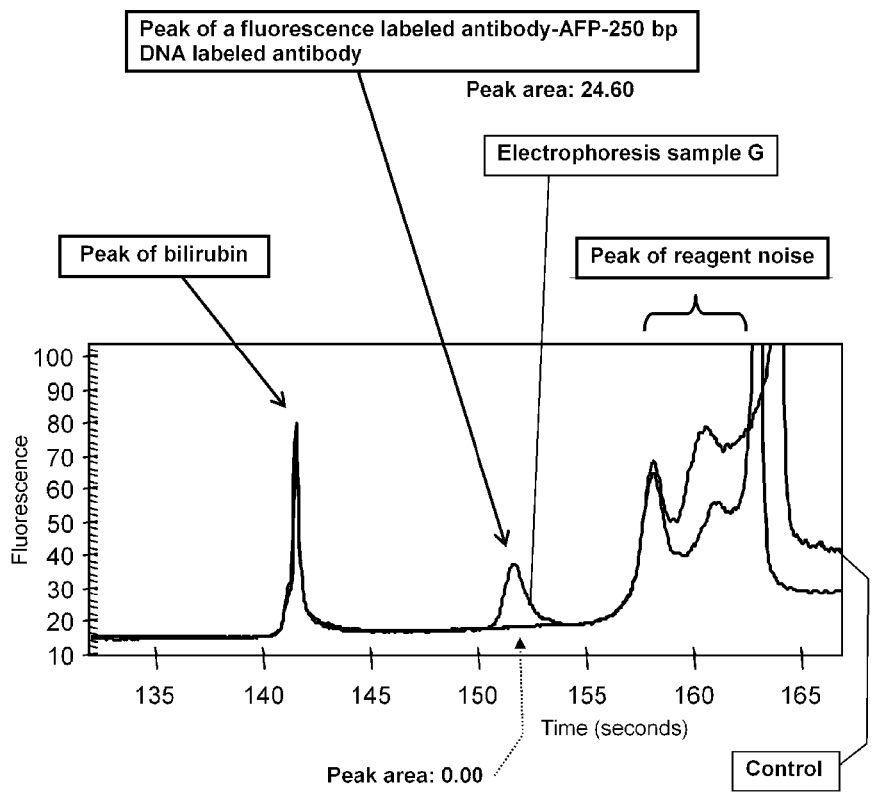
FIG. 14 shows an electropherogram in the case of using an electrophoresis sample G (a (serum, bilirubin and the MES ion)-containing sample) [Experiment No. 2-7] (ITP-CE), obtained in Example 2.

FIG. 14 shows an electrophoresis image (an electropherogram) in the case of using an electrophoresis sample G (a (serum, bilirubin and the MES ion)-containing sample) [Experiment No. 2-7]. In this connection, the case of not using the reagent solution (a DNA labeled antibody-containing solution) (result using only the electrophoresis sample) is also shown as a control. In addition, peak area in the Figure was determined by a common method.

In this connection, in FIG. 9 to FIG. 14, the Y axis and the X axis represent peak intensity and retention time, respectively From the results of FIG. 9, it is found that a peak at the vicinity of 152 seconds is a peak of the objective immune complex of the fluorescence labeled antibody-AFP-250 bp DNA labeled antibody. That is, in the case of using the electrophoresis sample A (the serum free sample) [experiment No. 2-1], because the DNA labeled antibody is not present, said immune complex is not formed (the peak does not appear). On the other hand, in the case of using the electrophoresis sample B (the sample added with AFP) [experiment No. 2-2], said immune complex is formed, and the peak appears at the vicinity of 152 seconds.

From the result of the case where the electrophoresis sample A (the serum free sample) [experiment No. 2-1] in FIG. 9 was used, and from the result of the case where the electrophoresis sample B (the sample not including serum) [experiment No. 2-2] was used, and from the result of the case where the electrophoresis sample C (the sample added with serum) [experiment No. 2-3] in FIG. 10 was used, it is found that a peak derived from the coexisting materials in the serum appears between 140 seconds and 155 seconds including the peak (a peak at the vicinity of 152 seconds) of the objective immune complex of the fluorescence labeled antibody-AFP-250 bp DNA labeled antibody.

From the result (in particular result of the control) of the case where the electrophoresis sample D (the serum-containing sample: not including bilirubin) [experiment No. 2-4] in FIG. 11 was used, and from the result (in particular result of the control) of the case where the electrophoresis sample E (the (serum and bilirubin)-containing sample) [experiment No. 2-5] in FIG. 12 was used, it is found that a peak at the vicinity of 150 seconds increases, in the case of using the electrophoresis sample E (the (serum and bilirubin)-containing sample) [experiment No. 2-5], as compared with the case of using the serum sample not added with bilirubin. From this, it is found that in the peak derived from the coexisting materials in serum in FIG. 10, the peak derived from at least bilirubin is included.

From the result of the case where the electrophoresis sample C (the sample not including the MES ion) [experiment No. 2-3] in FIG. 10 was used, and from the result of the case where the electrophoresis sample F (the sample including the MES ion) [experiment No. 2-6] in FIG. 13 was used, it is found that the peak (the peak at the vicinity of 152 seconds) of the immune complex, is buried under the peak (the peak between 140 seconds and 155 seconds) derived from the coexisting materials, even when CZE is further carried out after carrying out ITP in the absence of the MES ion, and the both peaks are not separated, whereas, the peak (the peak at the vicinity of 152 seconds) of the immune complex, and the peak (the peak at the vicinity of 142 seconds) derived from the coexisting materials are efficiently separated in the case where CZE is further carried out in the presence of the MES ion (namely, in the case of using the electrophoresis sample F) after carrying out ITP in the presence of the MES ion.

In addition, similarly, from the result of the case where the electrophoresis sample E (the (serum and bilirubin)-containing sample) [experiment No. 2-5] in FIG. 12 was used, and from the result of the case where the electrophoresis sample G (the (serum, bilirubin and the MES ion)-containing sample) [experiment No. 2-7] in FIG. 14 was used, it is found that the peak (the peak at the vicinity of 152 seconds) of the immune complex, and the peak (the peak at the vicinity of 150 seconds) derived from bilirubin are not separated, in the case where the MES ion is not present, whereas, the peak (the peak at the vicinity of 152 seconds) of the immune complex, and the peak (the peak at the vicinity of 142 seconds) derived from bilirubin are sufficiently separated by making the MES ion existed.

As is clear from the above, it is found that the objective complex and the coexisting materials can be separated more efficiently, by carrying out CZE further, in the presence of the MES ion and/or the glutamate ion, after carrying out ITP.

From FIGS. 11, 12 and 14, peak area of the immune complex in each electrophoresis sample, and area of a peak corresponding to a peak of said immune complex in the control are determined respectively.

In addition, from an electrophoretic image (electropherogram) (not shown particularly) obtained by carrying out ITP-CZE using the following comparative sample, peak area was determined similarly.

Further, difference (difference value) between the obtained peak area in the electrophoresis sample and peak area in the control, and ratio [area ratio (%)] of the difference value in each electrophoresis sample to the difference value in the comparative sample are each shown in Table 3.

[Comparative Test Samples]

As a specimen, 1 µL of PBS including 100 pM AFP(PBS added with AFP), 1 µL of 1 µM fluorescence labeled antibody, and 8 µL of sample buffer [75 mM Tris-HCl (pH7.5) containing 0.6% (w/v) pDMA, 3% (w/v) glycerol, 75 mM NaCl, 0.01% BSA: not including the MES ion] were mixed in a 0.5 mL tube to prepare 10 µL of reaction solution. The reaction solution was stood still on ice to be subjected to an antigen-antibody reaction for about 30 minutes to obtain an immune complex of the fluorescence labeled antibody-AFP. In this connection, final concentration of the fluorescence labeled antibody was 100 nM.

TABLE 3

| | | Electrophoresis samples | | | | | Peak area of immune complex | | | |
|---|---|---|---|---|---|---|---|---|---|---|
| Exp. No. | Samp. No. | Specimen | | | | | Electro- Phoresis samples | Cont. | Differ. value | Area ratio |
| | | Serum | PBS | AFP | Bilirubin | MES | | | | |
| — | Comp. | — | ○ | ○ | — | — | 24.24 | 0.00 | 24.24 | — |
| 2-4 | D | ○ | — | ○ | — | — | 25.43 | 0.03 | 25.40 | 104.79% |
| 2-5 | E | ○ | — | ○ | ○ | — | 37.95 | 14.84 | 23.11 | 95.34% |
| 2-7 | G | ○ | — | ○ | ○ | ○ | 24.60 | 0.00 | 24.60 | 101.49% |

As is clear from Table 3, the difference value in the electrophoresis sample G including the MES ion [experiment No. 2-7] (FIG. 14) was 24.60, and the ratio (area ratio) to the difference value (24.24) in the sample not including serum (comparative sample) was 101.49%. That is, it is found that in the electrophoresis sample G including the MES ion [Experiment No. 2-7], the objective complex can be measured in good precision little receiving influence of the coexisting material (bilirubin).

On the other hand, the difference value in the electrophoresis sample D not including the MES ion [experiment No. 2-4] (FIG. 11) was 25.40, and the ratio (area ratio) to the difference value (24.24) in the sample not including serum (comparative sample) was 104.79%. In addition, the difference value in the electrophoresis sample E not including the MES ion [experiment No. 2-5] (FIG. 12) was 23.11, and the ratio (area ratio) to the difference value (24.24) in the sample not including serum (comparative sample) was 95.34%. That is, it is found that the case of using the electrophoresis sample not including the MES ion results in receiving influence of the coexisting materials (in particular, bilirubin).

Example 3

Study on Ion Species

[An Analyte (an Antigen)]]
PIVKAII (protein induced by vitamin K absence or antagonist): It was prepared in accordance with a method described in Poser J W, Price P A. J Biol. Chem. 1979 Jan. 25; 254(2): 431-6.
[A Mobility-Changing Binding Substance (a DNA Labeled Antibody)]
Using an anti PIVKAII antibody (manufactured by Wako Pure Chemical Industries, Ltd.), instead of an anti AFP antibody WA1 (manufactured by Wako Pure Chemical Industries, Ltd.), an anti PIVKAII antibody Fab' fragment (a 250 by DNA labeled antibody) bound with a 250 by DNA fragment was prepared according to the procedure of Example 1.
[A Label Binding Substance (a Fluorescence Labeled Antibody)]
Using an anti prothrombin antibody (manufactured by Wako Pure Chemical Industries, Ltd.), instead of a WA2 antibody, a HiLyte 647 labeled anti prothrombin antibody Fab' fragment (a fluorescence labeled antibody) was prepared according to the procedure of Example 1.
[A Microchip]
The same one as in Example 1 was used.
[Electrophoresis]
(1) An Electrophoresis Sample
[An Electrophoresis Sample H]
As a specimen, 2 µL of PBS [50 mM phosphate buffer (pH6) including 0.1% BSA and 150 mM NaCl]; 1 µL of 1 µM fluorescence labeled antibody; and 7 µL of sample buffer [75 mM Tris-HCl (pH7.5) containing 0.6% (w/v) pDMA, 3% (w/v) glycerol, 75 mM NaCl, 0.01% BSA] were mixed in a 0.5 mL tube to prepare 10 µL of mixed solution. The mixed solution was stood still on ice for about 30 minutes. In this connection, final concentration of the fluorescence labeled antibody was 100 nM.

The resultant mixed solution was used as the electrophoresis sample H.
[An Electrophoresis Sample I]
As a specimen, 2 µL of PBS including 1 nM PIVKAII (PBS added with PIVKAII), 1 µL of 1 µM fluorescence labeled antibody and 7 µL of sample buffer [75 mM Tris-HCl (pH7.5) containing 0.6% (w/v) pDMA, 3% (w/v) glycerol, 75 mM NaCl, 0.01% BSA] were mixed in a 0.5 mL tube to prepare 10 µL of reaction solution. The reaction solution was stood still on ice to be subjected to an antigen-antibody reaction for about 30 minutes to form a [fluorescence labeled antibody-PIVKAII] immune complex. In this connection, final concentration of the fluorescence labeled antibody was 100 nM.

The resultant mixed solution was used as the electrophoresis sample I.
[An Electrophoresis Sample J]
As a specimen, 2 µL of serum including 100 µM PIVKAII (serum added with PIVKAII), 1 µL of 1 µM fluorescence labeled antibody and 7 µL of sample buffer [75 mM Tris-HCl (pH7.5) including 0.6% (w/v) pDMA, 3% (w/v) glycerol, 75 mM NaCl, 0.01% BSA: not including ion spieces] were mixed in a 0.5 mL tube to prepare 10 µL of reaction solution. The reaction solution was stood still on ice to be subjected to an antigen-antibody reaction for about 30 minutes to form a [fluorescence labeled antibody-PIVKAII] immune complex. In this connection, final concentration of the fluorescence labeled antibody was 100 nM.

The resultant immune complex-containing reaction solution was used as the electrophoresis sample J.
[An Electrophoresis Sample K]
As a specimen, 2 µL of serum including 100 µM PIVKAII and 20 mg/dL bilirubin (serum added with PIVKAII and bilirubin), 1 µL of 1 µM fluorescence labeled antibody and 7 µL of sample buffer [75 mM Tris-HCl (pH7.5) including 0.6% (w/v) pDMA, 3% (w/v) glycerol, 75 mM NaCl, 0.01% BSA: not including ion species] were mixed in a 0.5 mL tube to prepare 10 µL of reaction solution. The reaction solution was stood still on ice to be subjected to an antigen-antibody reaction for about 30 minutes to form a [fluorescence labeled antibody-PIVKAII] immune complex. In this connection, final concentration of the fluorescence labeled antibody was 100 nM.

The resultant immune complex-containing reaction solution was used as the electrophoresis sample K.

[An Electrophoresis Sample L]

As a specimen, 2 μL of serum including 100 μM PIVKAII and 20 mg/dL bilirubin (serum added with PIVKAII and bilirubin), 1 μL of 1 μM fluorescence labeled antibody and 7 μL of sample buffer [75 mM Tris-HCl (pH7.5) including 0.6% (w/v) pDMA, 3% (w/v) glycerol, 75 mM NaCl, 0.01% BSA] including the MES ion were mixed in a 0.5 mL tube to prepare 10 μL of reaction solution. The reaction solution was stood still on ice to be subjected to an antigen-antibody reaction for about 30 minutes to form a [fluorescence labeled antibody-PIVKAII] immune complex. In this connection, final concentration of the fluorescence labeled antibody was 100 nM.

The resultant immune complex-containing reaction solution was used as the electrophoresis sample L.

[An Electrophoresis Sample M]

As a specimen, 2 μL of serum including 1 nM PIVKAII (serum added with PIVKAII), 1 μL of 1 μM fluorescence labeled antibody and 7 μL of sample buffer [75 mM Tris-HCl (pH7.5) including 0.6% (w/v) pDMA, 3% (w/v) glycerol, 75 mM NaCl, 0.01% BSA: not including ion species] were mixed in a 0.5 mL tube to prepare 10 μL of reaction solution. The reaction solution was stood still on ice to be subjected to an antigen-antibody reaction for about 30 minutes to form a [fluorescence labeled antibody-PIVKAII] immune complex. In this connection, final concentration of the fluorescence labeled antibody was 100 nM.

The resultant immune complex-containing reaction solution was used as the electrophoresis sample M.

[An Electrophoresis Samples N to U]

As a specimen, 2 μL of serum including 1 nM PIVKAII (serum added with PIVKAII), 1 μL of 1 μM fluorescence labeled antibody and 7 μL of sample buffer [75 mM Tris-HCl (pH7.5) including 0.6% (w/v) pDMA, 3% (w/v) glycerol, 75 mM NaCl, 0.01% BSA] including 5 mM a predetermined ion species were mixed in a 0.5 mL tube to prepare 10 μL of reaction solution. The reaction solution was stood still on ice to be subjected to an antigen-antibody reaction for about 30 minutes to form a [fluorescence labeled antibody-PIVKAII] immune complex. In this connection, final concentration of the fluorescence labeled antibody was 100 nM.

The resultant immune complex-containing reaction solution was used as the electrophoresis samples N to U.

(2) Ion Species

The following ion species were used.

MES ion: 2-(N-morpholino)ethane sulfonic acid-monohydrate [manufactured by Dojindo Laboratories]

MOPS ion: 3-morpholinopropane sulfonic acid [manufactured by Dojindo Laboratories]

MOPSO ion: 2-hydroxy-3-morpholinopropane sulfonic acid [manufactured by Dojindo Laboratories]

Taurine ion: taurine [manufactured by Wako Pure Chemical Industries, Ltd.]

Glutamate ion: L(+)-sodium hydrogen glutamate-monohydrate [manufactured by Wako Pure Chemical Industries, Ltd.]

Phosphate ion: disodium hydrogen phosphate [manufactured by Wako Pure Chemical Industries, Ltd.]

Citrate ion: trisodium citrate [manufactured by Wako Pure Chemical Industries, Ltd.]

Threonine ion: L-threonine [manufactured by Ajinomoto Co., Inc.]

(3) Reagent Solution (a 250 by DNA Labeled Antibody-Containing Solution)

The leading buffer [75 mM Tris-HCl (pH7.5) including 0.6% (w/v) pDMA, 3% (w/v) glycerol, 75 mM NaCl, 0.01% BSA] containing 100 nM 250 by DNA labeled antibody was used as the reagent solution.

(4) Procedures of Electrophoresis a) Introduction of the Electrophoresis Sample and the Reagent Solution It was carried out similarly as in Example 2.

b) ITP (Reaction, Concentration and Separation)

It was carried out similarly as in Example 2.

c) CZE (Separation and Detection)

It was carried out similarly as in Example 2.

In Table 4, combinations and compositions of the electrophoresis samples and the reagent solution reacted are shown.

TABLE 4

| Exp. No. | Samp. No. | Electrophoresis samples | | | | | | Reagent solution |
|---|---|---|---|---|---|---|---|---|
| | | Specimen | | | | Fluorecsent antibody | Ion sp. (5 mM) | DNA antibody |
| | | Serum | PBS | PIVKAII | Bilirubin | | | |
| 3-1 | H | — | 2 μL | — | — | 100 nM | — | 100 nM |
| 3-2 | I | — | 2 μL | 1 nM (added) | — | 100 nM | — | 100 nM |
| 3-3 | J | 2 μL | — | 100 pM (added) | — | 100 nM | — | 100 nM |
| 3-4 | K | 2 μL | — | 100 pM (added) | 20 mg/dL (added) | 100 nM | — | 100 nM |
| 3-5 | L | 2 μL | — | 100 pM (added) | 20 mg/dL (added) | 100 nM | MES | 100 nM |
| 3-6 | M | 2 μL | — | 1 nM (added) | — | 100 nM | — | 100 nM |
| 3-7 | N | 2 μL | — | 1 nM (added) | — | 100 nM | MES | 100 nM |
| 3-8 | O | 2 μL | — | 1 nM (added) | — | 100 nM | MOPS | 100 nM |
| 3-9 | P | 2 μL | — | 1 nM (added) | — | 100 nM | MOPSO | 100 nM |
| 3-10 | Q | 2 μL | — | 1 nM (added) | — | 100 nM | taurine | 100 nM |
| 3-11 | R | 2 μL | — | 1 nM (added) | — | 100 nM | Glutamic acid | 100 nM |

TABLE 4-continued

| Exp. No. | Samp. No. | Electrophoresis samples ||||| Reagent solution |
| | | Specimen ||| | Fluorecsent | Ion sp. | DNA |
| | | Serum | PBS | PIVKAII | Bilirubin | antibody | (5 mM) | antibody |
|---|---|---|---|---|---|---|---|---|
| 3-12 | S | 2 µL | — | 1 nM (added) | — | 100 nM | Phosphoric acid | — 100 nM |
| 3-13 | T | 2 µL | — | 1 nM (added) | — | 100 nM | Citric acid | — 100 nM |
| 3-14 | U | 2 µL | — | 1 nM (added) | — | 100 nM | threonine | — 100 nM |

[Results]

Figure 15:
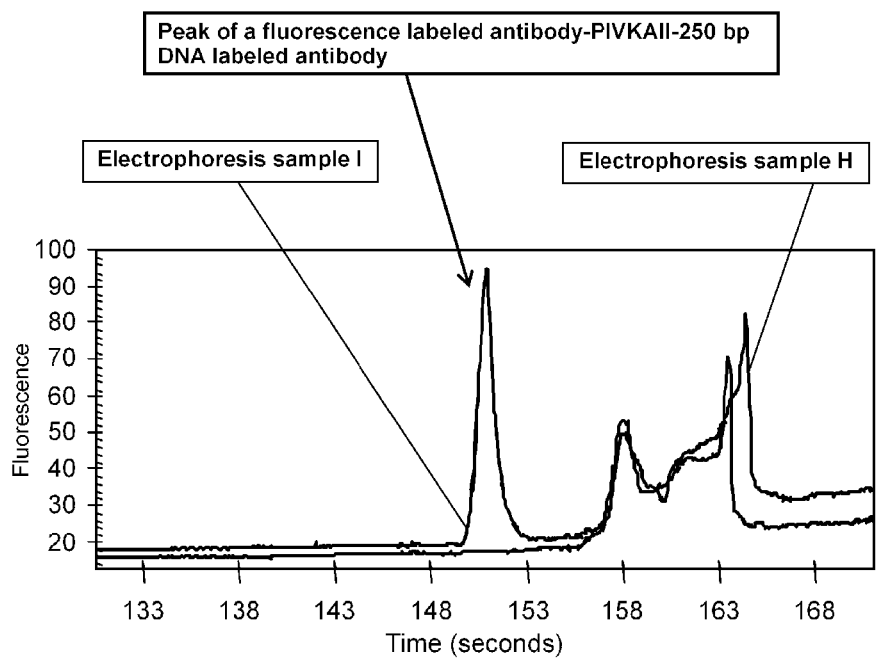
FIG. 15 shows an electropherogram in the case of using an electrophoresis sample H (a serum free sample) [Experiment No. 3-1] (ITP-CE), and in the case of using an electrophoresis sample I (a PIVKAII-containing sample) [Experiment No. 3-2] (ITP-CE), obtained in Example 3.

FIG. 15 shows an electrophoresis image (an electropherogram) in the case of using an electrophoresis sample H (a serum free sample) [Experiment No. 3-1], and an electrophoresis image (an electropherogram) in the case of using an electrophoresis sample I (a sample added with PIVKAII) [Experiment No. 3-2].

Figure 16:
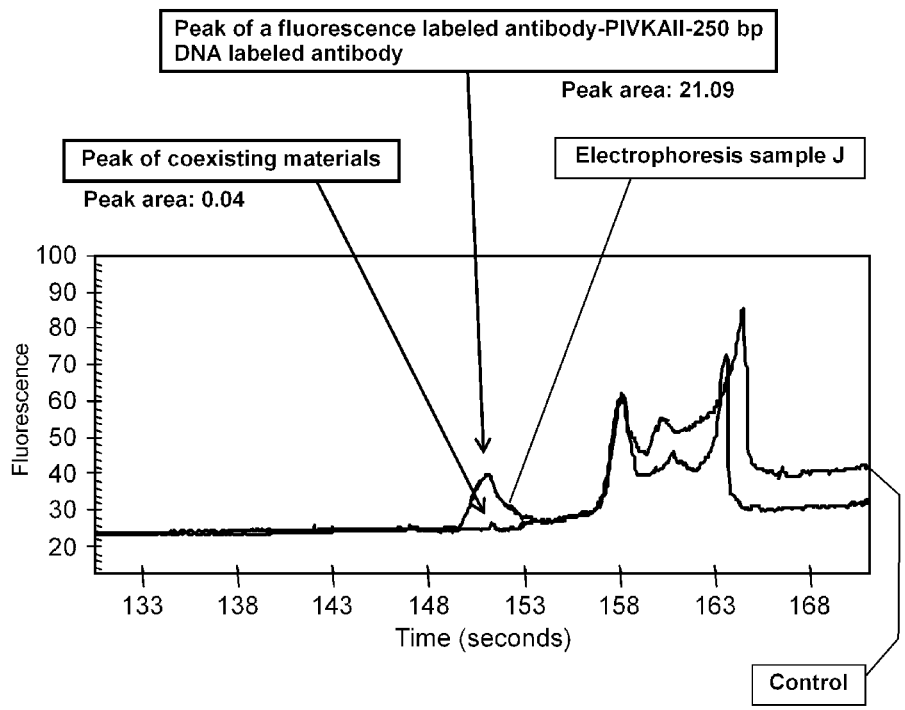
FIG. 16 shows an electropherogram in the case of using an electrophoresis sample J (a sample added with serum) [Experiment No. 3-3] (ITP-CE), obtained in Example 3.

FIG. 16 shows an electrophoresis image (an electropherogram) in the case of using an electrophoresis sample J (a sample added with serum) [Experiment No. 3-3]. In this connection, the case of not using the reagent solution (a DNA labeled antibody-containing solution) (result using only the electrophoresis sample) is also shown as a control. In addition, peak area in the Figure was determined by a common method.

Figure 17:
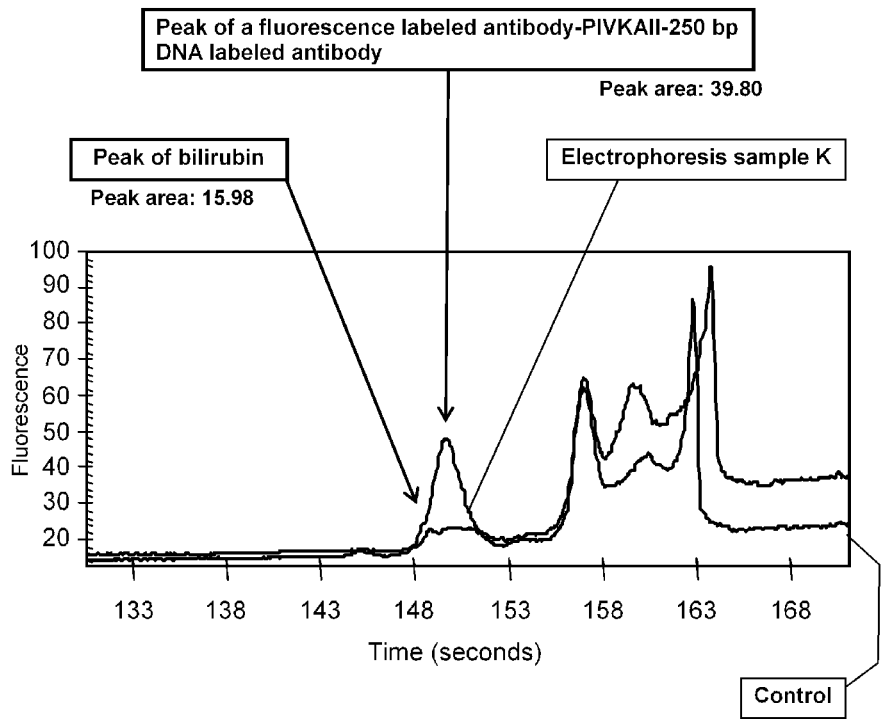
FIG. 17 shows an electropherogram in the case of using an electrophoresis sample K (a (serum and bilirubin)-containing sample) [Experiment No. 3-4] (ITP-CE), obtained in Example 3.

FIG. 17 shows an electrophoresis image (an electropherogram) in the case of using an electrophoresis sample K (a (serum and bilirubin)-containing sample) [Experiment No. 3-4]. In this connection, the case of not using the reagent solution (a DNA labeled antibody-containing solution) (result using only the electrophoresis sample) is also shown as a control. In addition, peak area in the Figure was determined by a common method.

Figure 18:
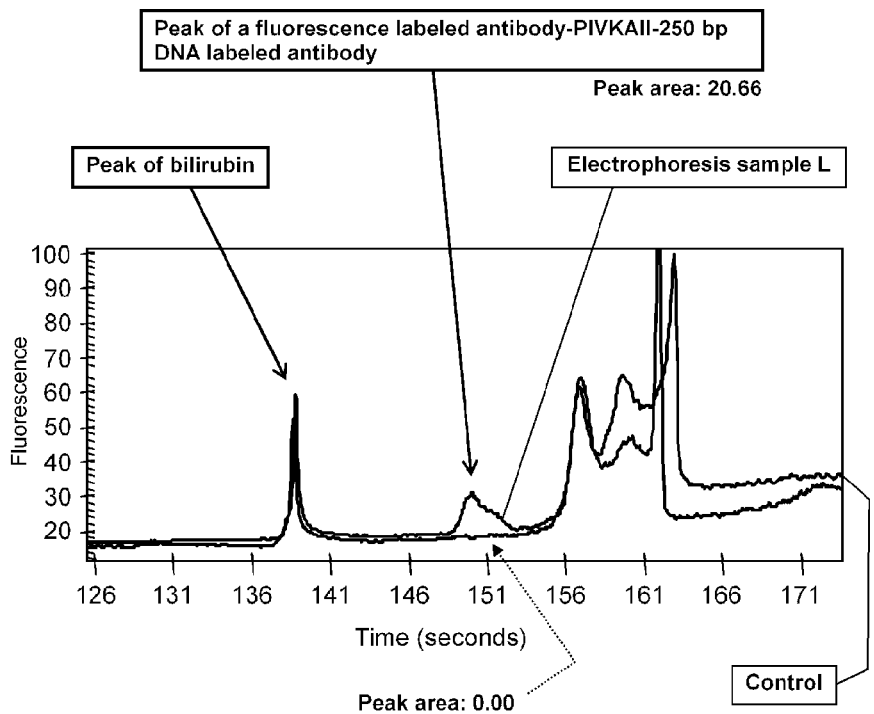
FIG. 18 shows an electropherogram in the case of using an electrophoresis sample L including the MES ion as an ion species and including serum and bilirubin [Experiment No. 3-5] (ITP-CE), obtained in Example 3.

FIG. 18 shows an electrophoresis image (an electropherogram) in the case of using an electrophoresis sample L including the MES ion as an ion species and including serum and bilirubin [Experiment No. 3-5]. In this connection, the case of not using the reagent solution (a DNA labeled antibody-containing solution) (result using only the electrophoresis sample) is also shown as a control.

Figure 19:
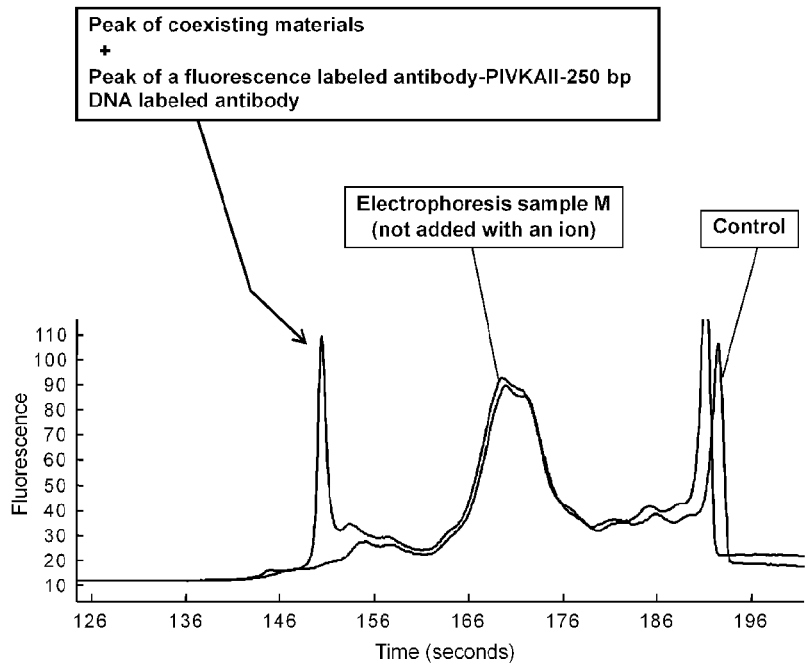
FIG. 19 shows an electropherogram in the case of using an electrophoresis sample M not including an ion species [Experiment No. 3-6] (ITP-CE), obtained in Example 3.

FIG. 19 shows an electrophoresis image (an electropherogram) in the case of using an electrophoresis sample M not including an ion species [Experiment No. 3-6]. In this connection, the case of not using the reagent solution (a DNA labeled antibody-containing solution) (result using only the electrophoresis sample) is also shown as a control.

Figure 20:
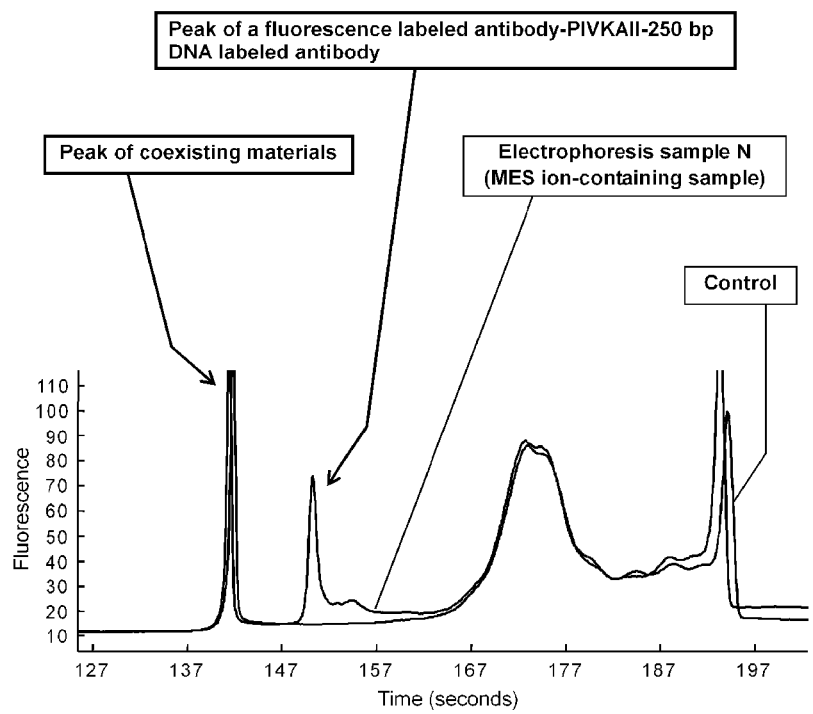
FIG. 20 shows an electropherogram in the case of using an electrophoresis sample N including the MES ion as an ion species [Experiment No. 3-7] (ITP-CE), obtained in Example 3.

FIG. 20 shows an electrophoresis image (an electropherogram) in the case of using an electrophoresis sample N including the MES ion as an ion species [Experiment No. 3-7]. In this connection, the case of not using the reagent solution (a DNA labeled antibody-containing solution) (result using only the electrophoresis sample) is also shown as a control.

Figure 21:
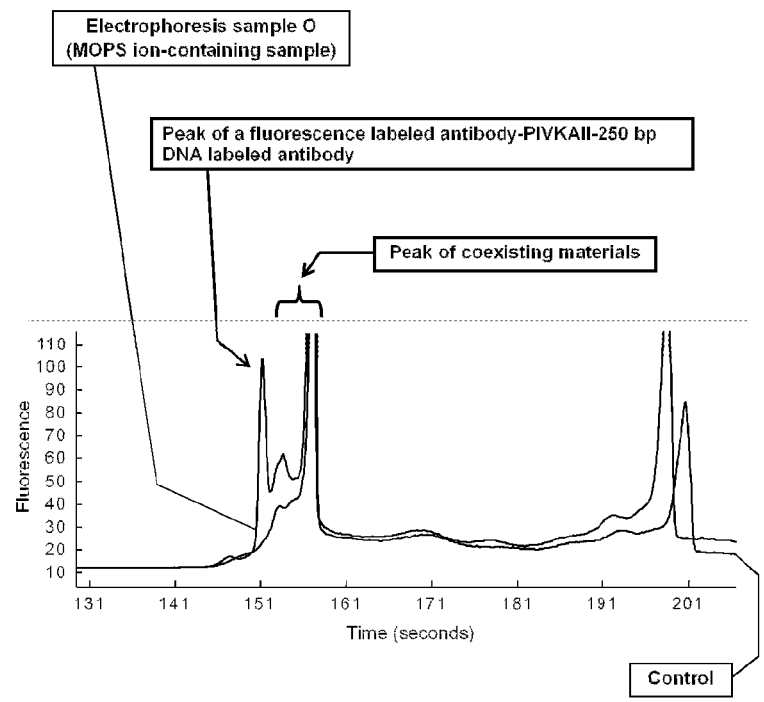
FIG. 21 shows an electropherogram in the case of using an electrophoresis sample O including an MOPS as an ion species [Experiment No. 3-8], obtained in Example 3.

FIG. 21 shows an electrophoresis image (an electropherogram) in the case of using an electrophoresis sample O including the MOPS as an ion species [Experiment No. 3-8]. In this connection, the case of not using the reagent solution (a DNA labeled antibody-containing solution) (result using only the electrophoresis sample) is also shown as a control.

Figure 22:
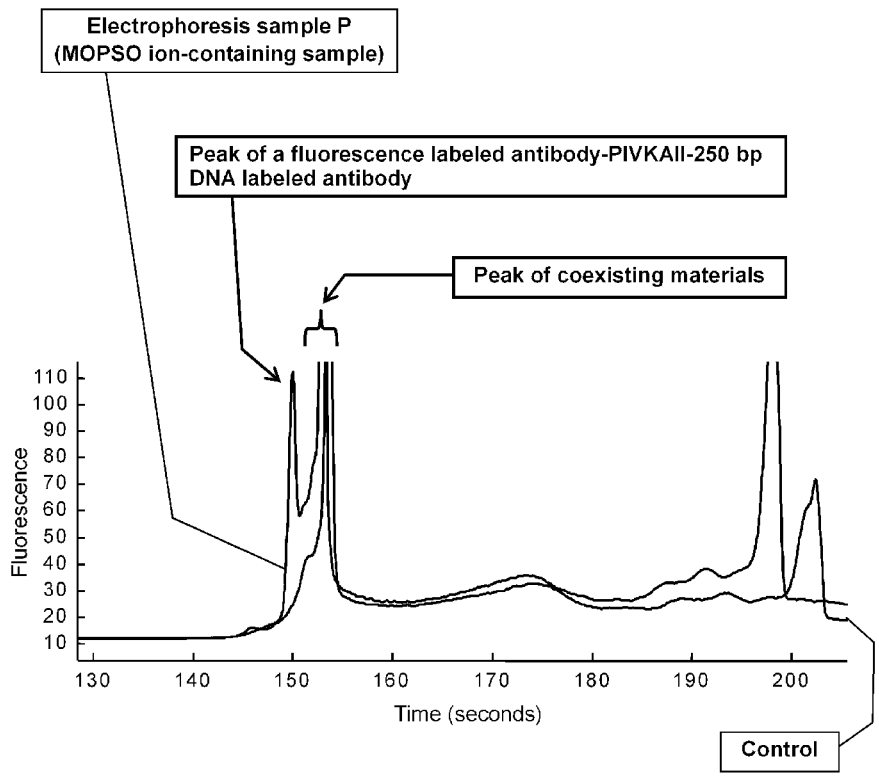
FIG. 22 shows an electropherogram in the case of using an electrophoresis sample P including MOPSO as an ion species [Experiment No. 3-9] (ITP-CE), obtained in Example 3.

FIG. 22 shows an electrophoresis image (an electropherogram) in the case of using an electrophoresis sample P including the MOPSO as an ion species [Experiment No. 3-9]. In this connection, the case of not using the reagent solution (a DNA labeled antibody-containing solution) (result using only the electrophoresis sample) is also shown as a control.

Figure 23:
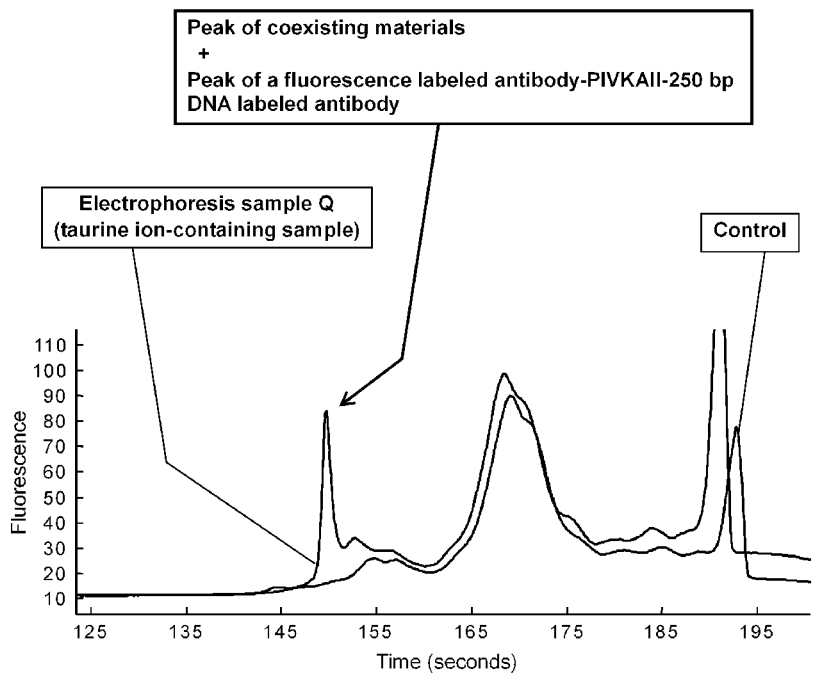
FIG. 23 shows an electropherogram in the case of using an electrophoresis sample Q including taurine as an ion species [Experiment No. 3-10] (ITP-CE), obtained in Example 3.

FIG. 23 shows an electrophoresis image (an electropherogram) in the case of using an electrophoresis sample Q including taurine as an ion species [Experiment No. 3-10]. In this connection, the case of not using the reagent solution (a DNA labeled antibody-containing solution) (result using only the electrophoresis sample) is also shown as a control.

Figure 24:
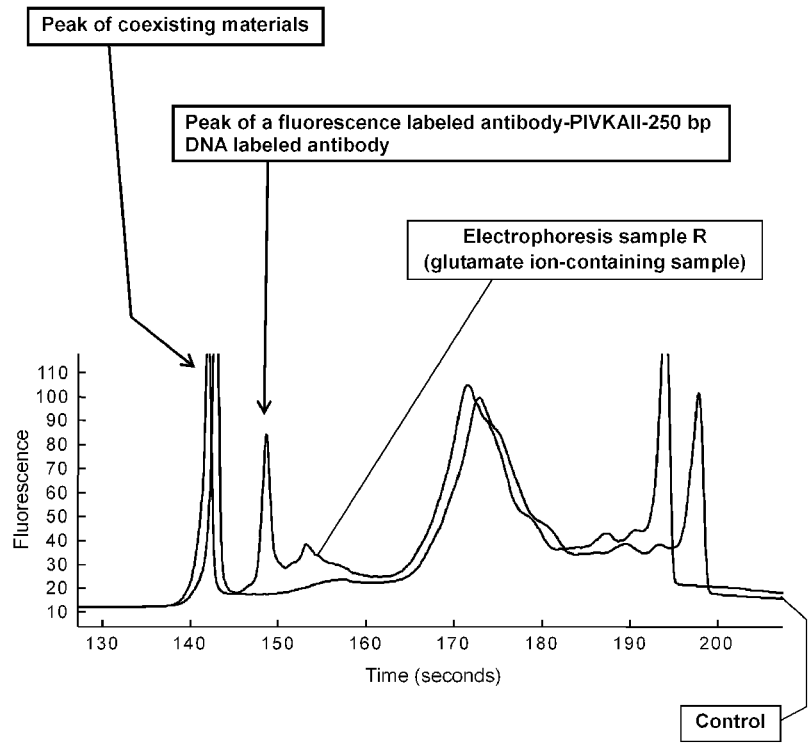
FIG. 24 shows an electropherogram in the case of using an electrophoresis sample R including the glutamate ion as an ion species [Experiment No. 3-11] (ITP-CE), obtained in Example 3.

FIG. 24 shows an electrophoresis image (an electropherogram) in the case of using an electrophoresis sample R including the glutamate ion as an ion species [Experiment No. 3-11]. In this connection, the case of not using the reagent solution (a DNA labeled antibody-containing solution) (result using only the electrophoresis sample) is also shown as a control.

In this connection, in FIG. 15 to FIG. 24, the Y axis and the X axis represent peak intensity and retention time, respectively From the results of FIG. 15, it is found that a peak at the vicinity of 151 seconds is a peak of the objective immune complex of the fluorescence labeled antibody-PIVKAII-250 bp DNA labeled antibody. That is, in the case of using the electrophoresis sample H (the serum free sample) [experiment No. 3-1], because the DNA labeled antibody is not present, said immune complex is not formed (the peak does not appear). On the other hand, in the case of using the electrophoresis sample I (the sample added with PIVKAII) [experiment No. 3-2], said immune complex is formed, and the peak appears at the vicinity of 151 seconds.

From the result of the case where the electrophoresis sample H (the serum free sample) [experiment No. 3-1] in FIG. 15 was used, and from the result of the case where the electrophoresis sample I (the sample not including serum) [experiment No. 3-2] was used, and from the result of the case where the electrophoresis sample J (the sample added with serum) [experiment No. 3-3] in FIG. 16 was used, it is found that a peak (at the vicinity of 150 to 152 seconds) derived from the coexisting materials in the serum appears at the vicinity of the peak of the objective immune complex of the fluorescence labeled antibody-PIVKAII-250 bp DNA labeled antibody.

From the result (in particular, result of the control) of the case where the electrophoresis sample J (the serum-containing sample: not including bilirubin) [experiment No. 3-3] in FIG. 16 was used, and from the result (in particular, result of the control) of the case where in the case of using the electrophoresis sample K (the (serum and bilirubin)-containing sample) [experiment No. 3-4] in FIG. 17 was used, it is found that the peak at the vicinity of 149 to 152 seconds increases, in the case of using the electrophoresis sample K (the (serum and bilirubin)-containing sample) [experiment No. 3-4], as compared with the case of using the serum sample not added with bilirubin. From this, it is found that in the peak derived from the coexisting materials in serum in FIG. 16, the peak derived from at least bilirubin is included.

From the result of the case where the electrophoresis sample K (the sample not including the MES ion) [experiment No. 3-4] in FIG. 17 was used, and from the result of the case where the electrophoresis sample L (the sample including the MES ion) [experiment No. 3-5] in FIG. 18 was used, it is found that the peak (the peak at the vicinity of 150 seconds) of the immune complex, and the peak (the peak between 149 seconds and 152 seconds) derived from the coexisting materials overlap, even when CZE is carried out after carrying out ITP in the absence of the MES ion, and the both peaks are not separated, whereas, the peak (the peak at the vicinity of 150 seconds) of the immune complex, and the peak (the peak at the vicinity of 139 seconds) derived from the coexisting materials are efficiently separated in the case where CZE is further carried out in the presence of the MES ion, after carrying out ITP in the presence of the MES ion.

From FIGS. 16, 17 and 18, peak area of the immune complex in each electrophoresis sample, and area of a peak corresponding to a peak of said immune complex in the control are each determined. The results are shown in Table 5.

In addition, from an electrophoretic image (electropherogram) (not shown particularly), obtained by carrying out ITP-CZE using the following comparative sample, peak area was determined similarly.

Further, difference (difference value) between the resultant peak area in the electrophoresis sample and peak area in the control, and ratio [area ratio (%)] of the difference value in each electrophoresis sample to the difference value in the comparative sample are each shown in Table 5.

[Comparative Test Samples]

As a specimen, 2 µL of PBS including 100 µM PIVKAII (PBS added with PIVKAII), 1 µL of 1 µM fluorescence labeled antibody, and 7 µL of sample buffer [75 mM Tris-HCl (pH7.5) including 0.6% (w/v) pDMA, 3% (w/v) glycerol, 75 mM NaCl, 0.01% BSA: not including an ion species] were mixed in a 0.5-mL tube to prepare 10-µL of reaction solution. The reaction solution was stood still on ice to be subjected to an antigen-antibody reaction for about 30 minutes to obtain a [fluorescence labeled antibody-PIVKAII] immune complex. In this connection, final concentration of the fluorescence labeled antibody was 100 nM that the case of using the electrophoresis sample not including the MES ion results in receiving influence of the coexisting materials (in particular, bilirubin).

From the results of FIG. 19 to FIG. 24, it is found that, in the case where the electrophoresis sample K including the MES ion (the MES ion-containing sample) (FIG. 20) was used, and in the case where the electrophoresis sample O including the glutamate ion (the glutamate ion-containing sample) (FIG. 24) was used, the peak (concentrated peak) of the objective immune complex of the fluorescence labeled antibody-PIV-KAII-250 bp DNA labeled antibody, and the peak (noise peak) of the coexisting materials are efficiently separated.

On the other hand, in any of the case where the electrophoresis sample L including the MOPS ion (FIG. 21) was used, in the case where the electrophoresis sample M including the MOPSO ion (FIG. 22) was used, and in the case where the electrophoresis sample N including the taurine ion (FIG. 23) was used, it is found that the peak (concentrated peak) of the objective immune complex of the fluorescence labeled antibody-PIVKAII-250 bp DNA labeled antibody, and the peak (noise peak) of the coexisting materials cannot be separated well. In this connection, it was confirmed that in the case where the electrophoresis sample S including the phosphate ion was used, in the case where the electrophoresis sample T including the citrate ion was used, and in the case where the electrophoresis sample U including the threonine ion was used, although electrophoresis images (electropherograms) are not shown in particular, the peak (concentrated peak) of the objective immune complex of the fluorescence labeled antibody-PIVKAII-250 bp DNA labeled antibody, and the peak (noise peak) of the coexisting materials cannot be separated well.

As is clear from the above, it is found that only the MES ion and the glutamate ion, among these various kinds of ion species, are capable of separating the objective complex and the coexisting materials well.

TABLE 5

| Exp. No. | Samp. No. | Electrophoresis samples | | | | | Peak area of immune complex | | | |
|---|---|---|---|---|---|---|---|---|---|---|
| | | Specimen | | | | | Electrophoresis samples | Cont. | Differ. value | Area ratio |
| | | Serum | PBS | PIVKAII | Bilirubin | MES | | | | |
| — | Comp. | — | ○ | ○ | — | — | 20.19 | 0.00 | 20.19 | — |
| 3-3 | J | ○ | — | ○ | — | — | 21.09 | 0.04 | 21.05 | 104.26% |
| 3-4 | K | ○ | — | ○ | ○ | — | 39.80 | 15.98 | 23.82 | 117.98% |
| 3-5 | L | ○ | — | ○ | ○ | ○ | 20.66 | 0.00 | 20.66 | 102.33% |

As is clear from Table 5, the difference value in the electrophoresis sample L including the MES ion [experiment No. 3-5] (FIG. 18) was 20.66, and the ratio (area ratio) to the difference value (20.19) in the sample not including serum (comparative sample) was 102.33%. That is, it is found that in the electrophoresis sample L including the MES ion [Experiment No. 3-5], the objective complex can be measured in good precision little receiving influence of the coexisting material (bilirubin).

On the other hand, the difference value in the electrophoresis sample J not including the MES ion [experiment No. 3-3] (FIG. 16) was 21.05, and the ratio (area ratio) to the difference value (20.19) in the sample not including serum (comparative sample) was 104.26%. In addition, the difference value in the electrophoresis sample K not including the MES ion [experiment No. 3-4] (FIG. 17) was 23.82, and the ratio (area ratio) to the difference value (20.19) in the sample not including serum (comparative sample) was 117.98%. That is, it is found In this connection, it is known that these ion species (the MES ion, the MOPS ion, the MOPSO ion, the taurine ion, the glutamate ion, the phosphate ion, the citrate ion and the threonine ion) have nearly the same degree of electrophoretic mobility as a spacer ion. However, it was a surprising finding that only the MES ion and the glutamate ion, among these ion species having the same degree of electrophoretic mobility, exhibit effect in separation of the coexisting materials in the blood-derived sample and the objective complex.

Example 4

Effect of the Negatively-Charged Polymer

[An Analyte (an Antigen)]
The same one as in Example 1 was used.
[A Mobility-Changing Binding Substance (a DNA Labeled Antibody)]
The same one as in Example 1 was used.

[A Label Binding Substance (a Fluorescence Labeled Antibody)]
The same one as in Example 1 was used.
[A Microchip]
The same one as in Example 1 was used.
[Electrophoresis]
(1) An Electrophoresis Sample (Sample Including the MES Ion)
[The Electrophoresis Sample V]
As a specimen, 1 μL of serum including 100 μM AFP and 20 mg/dL bilirubin (serum added with AFP and bilirubin), 1 μL of 1 μM fluorescence labeled antibody and 8 μL of sample buffer [75 mM Tris-HCl (pH7.5) including 0.6% (w/v) pDMA, 3% (w/v) glycerol, 75 mM NaCl, 0.01% BSA] including 3.6 mM MES, were mixed in a 0.5 mL tube to prepare 10 μL of reaction solution. The reaction solution was stood still on ice to be subjected to an antigen-antibody reaction for about 30 minutes to form an immune complex of fluorescence labeled antibody-AFP. In this connection, final concentration of the fluorescence labeled antibody was 100 nM.

The resultant reaction solution including the immune complex was used as the electrophoresis sample V.

(2) Reagent Solution (a 250 by DNA Labeled Antibody-Containing Solution)

The leading buffer [75 mM Tris-HCl (pH7.5) including 0.6% (w/v) pDMA, 3% (w/v) glycerol, 75 mM NaCl, 0.01% BSA] including 100 nM 250 bp DNA labeled antibody was used as the reagent solution.

(3) Procedures of Electrophoresis a) Introduction of the Electrophoresis Sample and the Reagent Solution The introduction was carried out similarly as in Example 2, except that, as the leading buffer to be introduced from the LB1 well and the LB2 well into the channel, each leading buffer [75 mM Tris-HCl (pH7.5) including 0.6% (w/v) pDMA, 3% (w/v) glycerol, 75 mM NaCl, 0.01% BSA] including 0% (w/v), 0.5% (w/v) or 2% (w/v) heparin [heparin Li: a molecular weight of 3000 to 30000, an average molecular weight of 15000 (manufactured by KRAEBER GMBH&CO)] was used.

b) ITP (Reaction, Concentration and Separation)
It was carried out similarly as in Example 2.

c) CZE (Separation and Detection)
It was carried out similarly as in Example 2.

In Table 6, combinations and compositions of the electrophoresis samples, the reagent solution and the leading buffer (the LB1 and the LB2) reacted are shown.

Figure 25:
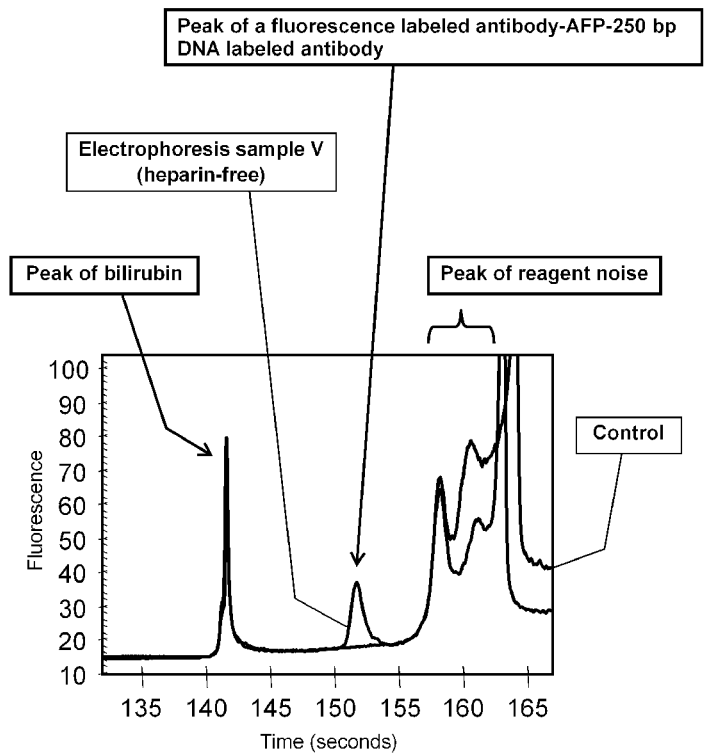
FIG. 25 shows an electropherogram in the case of using reagent solution not containing heparin (heparin 0% (w/v)) [Experiment No. 4-1] (ITP-CE), obtained in Example 4.

[Results]
FIG. 25 shows an electrophoresis image (an electropherogram) in the case of using the leading buffers (LB1, LB2) with 0% heparin (the leading buffers not including heparin) [Experiment No. 4-1] (the same one as FIG. 14). In this connection, the case of not using the reagent solution (a DNA labeled antibody-containing solution) (result using only the electrophoresis sample) is also shown as a control.

Figure 26:
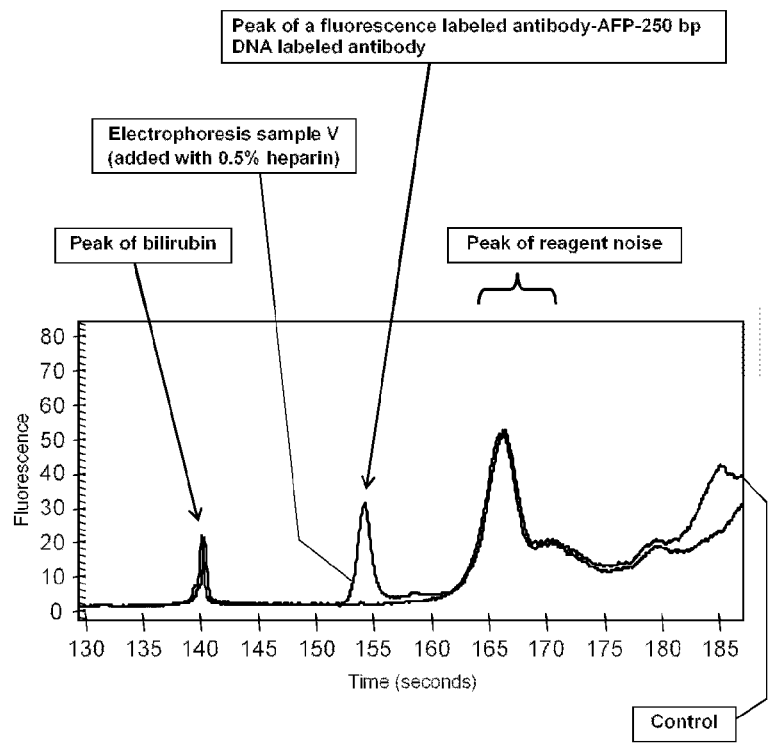
FIG. 26 shows an electropherogram in the case of using reagent solution containing 0.5% (w/v) heparin [Experiment No. 4-2] (ITP-CE), obtained in Example 4.

FIG. 26 shows an electrophoresis image (an electropherogram) in the case of using the leading buffers (LB1, LB2) including 0.5% (w/v) heparin [Experiment No. 4-2]. In this connection, the case of not using the reagent solution (a DNA labeled antibody-containing solution) (result using only the electrophoresis sample) is also shown as a control.

Figure 27:
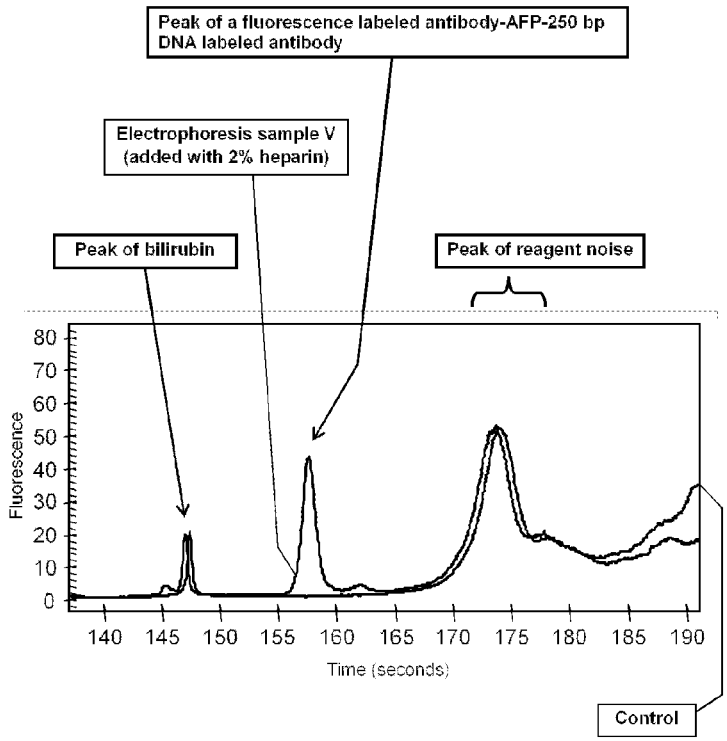
FIG. 27 shows an electropherogram in the case of using reagent solution containing 2% (w/v) heparin [Experiment No. 4-3] (ITP-CE), obtained in Example 4.

FIG. 27 shows an electrophoresis image (an electropherogram) in the case of using the leading buffers (LB1, LB2) including 2% (w/v) heparin [Experiment No. 4-3]. In this connection, the case of not using the reagent solution (a DNA labeled antibody-containing solution) (result using only the electrophoresis sample) is also shown as a control.

In this connection, in FIG. 25 to FIG. 27, the Y axis and the X axis represent peak intensity and retention time, respectively From the results of FIGS. 26 and 27, it is found that by carrying out CZE, in the presence of the MES ion and heparin, after carrying out ITP, in the presence of the MES ion, not only the peak (concentrated peak: the peak at the vicinity of 154 seconds of FIG. 26, and the peak at the vicinity of 158 seconds of FIG. 27) of the objective immune complex of the fluorescence labeled antibody-AFP-250 bp DNA labeled antibody, and the peak (noise peak: the peak at the vicinity of 140 seconds of FIG. 26, and the peak at the vicinity of 147 seconds of FIG. 27) of the coexisting materials (bilirubin) can be separated but also further the peak of reagent noise (non-bound labeling substances) (the peak at the vicinity of 163 to 175 seconds of FIG. 26, the peak at the vicinity of 172 to 183 seconds of FIG. 27) can be separated well.

On the other hand, from the results of FIG. 25, it is found that in the absence of heparin, although there are separated the peak (concentrated peak: the peak at the vicinity of 152 seconds of FIG. 25) of the objective immune complex of the fluorescence labeled antibody-AFP-250 bp DNA labeled antibody, the peak (noise peak: the peak at the vicinity of 142 seconds of FIG. 25) of the coexisting materials (bilirubin), and the peak of the reagent noise (non-bound labeling substances) (the peak at the vicinity of 157 to 162 seconds of FIG. 25), degree of the separation is low as compared with the case where heparin is present.

As is clear from the above, it is found that by carrying out CZE, in the presence of the negatively charged polymer such as heparin, the objective complex, can be separated well from the coexisting materials and reagent noise (non-bound labeling substances).

TABLE 6

| Exp. No. | Samp. No. | Electrophoresis samples | | | | | Reagent solution | LB |
| | | Serum | AFP | Bilirubin | Fluorecsent antibody | MES | DNA antibody | (LB1, LB2) heparin |
|---|---|---|---|---|---|---|---|---|
| 4-1 | V | 1 μL | 100 pM (added) | 20 mg/dL (added) | 100 nM | 3.6 mM | — 100 nM | 0% |
| 4-2 | V | 1 μL | 100 pM (added) | 20 mg/dL (added) | 100 nM | 3.6 mM | — 100 nM | 0.50% |
| 4-3 | V | 1 μL | 100 pM (added) | 20 mg/dL (added) | 100 nM | 3.6 mM | — 100 nM | 2% |

The invention claimed is:
1. A method for separating a complex, the method comprising:
(1) introducing in a capillary, between a leading buffer zone and a trailing buffer zone, wherein neither the leading buffer nor the trailing buffer comprises an ion selected from a 2-(N-morpholino)ethane sulfonate ion and a glutamate ion: (a) a blood-derived sample suspected of containing an analyte, (b) one or more mobility-changing complex forming substances (CFS) and (c) one or more labeled CFSs;

(2) contacting the analyte, the one or more mobility-changing CFSs, and the one or more labeled CFSs, wherein a complex is formed comprising the analyte, at least one of the one or more mobility-changing CFSs, and at least one of the one or more labeled CFCs; and (3) separating the complex from the labeled CFS not part of said complex and coexisting substances in the blood-derived sample by performing isotachophoresis in the presence of a 2-(N-morpholino)ethane sulfonate ion and/or a glutamate ion between the leading buffer zone and the trailing buffer zone.

2. The method of claim 1, wherein introducing said blood-derived sample, said one or more mobility-changing CFSs, and said one or more labeled CFSs between the leading buffer zone and the trailing buffer zone comprises introducing a solution comprising the blood-derived sample, the one or more mobility-changing CFSs, the one or more labeled CFSs and 2-(N-morpholino)ethane sulfonate ion and/or glutamate ion as a zone.

3. The method of claim 1, wherein introducing said blood-derived sample, said one or more mobility-changing CFSs, and said one or more labeled CFSs between the leading buffer zone and the trailing buffer zone comprises introducing (i) a solution of the blood-derived sample and one or more labeled CFSs, and (ii) a solution of the one or more mobility-changing CFSs, as separate zones, and wherein at least one solution introduced between the leading buffer zone and the trailing buffer zone further comprises 2-(N-morpholino)ethane sulfonate ion and/or glutamate ion.

4. The method of claim 1, wherein introducing said blood-derived sample, said one or more mobility-changing CFSs, and said one or more labeled CFSs between the leading buffer zone and the trailing buffer zone comprises introducing (i) a solution of the blood-derived sample, (ii) a solution of the one or more mobility-changing CFSs, and (iii) a solution of the one or more labeled CFSs, as separate zones, and wherein at least one solution introduced between the leading buffer zone and the trailing buffer zone further comprises 2-(N-morpholino)ethane sulfonate ion and/or glutamate ion.

5. The method of claim 3 or 4, wherein at the least solution comprising the blood-derived sample further comprises 2-(N-morpholino)ethane sulfonate ion and/or glutamate ion.

6. The method of claim 1, wherein the blood-derived sample further comprises bilirubin, a metabolite of bilirubin, or a complex of bilirubin and protein.

7. The method of claim 1, wherein the one or more mobility-changing CFSs are anionic.

8. The method of claim 7, wherein the anionic mobility-changing CFSs independently comprise a polynucleotide, a protein, a polypeptide, or a polyamino acid.

9. The method of claim 7, wherein the anionic mobility-changing CFSs comprise a DNA polynucleotide.

10. The method of claim 7, wherein the anionic mobility-changing CFSs comprise a double-stranded DNA polynucleotide.

11. The method of claim 1, wherein the leading buffer comprises chloride as a leading ion.

12. The method of claim 1, wherein the trailing buffer comprises a trailing ion selected from HEPES, TAPS, MOPS, glycin, and threonine.

13. The method of claim 1, further comprising after performing isotachophoresis:

(4) subjecting the complex to capillary zone electrophoresis or capillary gel electrophoresis in the presence of 2-(N-morpholino)ethane sulfonate ion and/or glutamate ion.

14. The method of claim 13, wherein the complex and the coexisting substances in the blood-derived sample are subjected to capillary zone electrophoresis or capillary gel electrophoresis in the presence of 2-(N-motpholino)ethane sulfonate ion.

15. The method of claim 13, wherein capillary zone electrophoresis or capillary gel electrophoresis is carried out in the presence of a negatively-charged polymer.

16. The method of claim 15, wherein the negatively-charged polymer is a polyanionic polysaccharide and/or a polyanionic synthetic polymer.

17. The method of claim 15, wherein the negatively-charged polymer is selected from heparin, heparan sulfate, chondroitin sulfate, dextran sulfate, polytungstic acid, tungstophosphoric acid, hyaluronic acid, dermatan sulfate, and polyanethole sulfate, and salts thereof.

18. The method of claim 15, wherein the negatively-charged polymer is heparin or a salt thereof.

19. The method of claim 15, wherein the negatively-charged polymer is initially present in the leading buffer zone and/or the trailing buffer zone.

20. A method for separating a complex, the method comprising:

(1) arranging in a capillary, between a leading buffer zone and a trailing buffer zone, wherein neither the leading buffer nor the trailing buffer comprises an ion selected from a 2-(N-morpholino)ethane sulfonate ion and a glutamate ion:

(a) three zones comprising (i) a solution of a blood-derived sample suspected of containing an analyte and 2-(N-morpholino)ethane sulfonate ion and/or glutamate ion, (ii) a solution of one or more mobility-changing CFSs, and (iii) a solution of one or more labeled CFSs, as separate zones; or (b) two zones comprising (i) a solution of a blood-derived sample suspected of containing an analyte, one or more labeled CFSs, and 2-(N-morpholino)ethane sulfonate ion and/or glutamate ion, and (ii) a solution of one or more mobility-changing CFSs, as separate zones;

(2) contacting the blood-derived sample suspected of containing an analyte, the one or more mobility-changing CFSs, and the one or more labeled CFSs, wherein a complex is formed comprising the analyte, at least one of the one or more mobility-changing CFSs, and at least one of the one or more labeled CFCs;

(3) separating the complex from the labeled CFS not part of said complex and coexisting substances in the blood-derived sample by performing isotachophoresis in the presence of the 2-(N-morpholino)ethane sulfonate ion and/or a glutamate ion; and (4) separating the complex and coexisting substances in the blood-derived sample by performing capillary zone electrophoresis or capillary gel electrophoresis in the presence of a negatively-charged polymer;

wherein the negatively-charged polymer is initially present in at least one of the leading buffer zone, the trailing buffer zone, the solution of one or more mobility-changing CFSs, and the solution of one or more labeled CFSs.

21. The method of claim 20, wherein the leading buffer comprises chloride as a leading ion.

22. The method of claim 20, wherein the trailing buffer comprises a trailing ion selected from HEPES, TAPS, MOPS, glycin, and threonine.

23. The method of claim 20, wherein the method further comprises quantifying the amount of analyte by detecting the labeled CFS present in the complex and/or the labeled CFS not part of said complex.

24. The method of claim 20, wherein the negatively-charged polymer is a polyanionic polysaccharide and/or a polyanionic synthetic polymer.

25. The method of claim 20, wherein the negatively-charged polymer is selected from heparin, heparan sulfate, chondroitin sulfate, dextran sulfate, polytungstic acid, tungstophosphoric acid, hyaluronic acid, dermatan sulfate, and polyanethole sulfate, and salts thereof.

26. The method of claim 20, wherein the negatively-charged polymer is heparin or a salt thereof.

27. A method for separating a complex, the method comprising:
(1) introducing in a capillary, between a leading buffer zone and a trailing buffer zone: (a) a blood-derived sample suspected of containing an analyte, (b) one or more mobility-changing complex forming substances (CFS) and (c) one or more labeled CFSs;
(2) contacting the analyte, the one or more mobility-changing CFSs, and the one or more labeled CFSs, wherein a complex is formed comprising the analyte, at least one of the one or more mobility-changing CFSs, and at least one of the one or more labeled CFCs; and
(3) separating the complex from the labeled CFS not part of said complex and coexisting substances in the blood-derived sample by performing isotachophoresis in the presence of a glutamate ion between the leading buffer zone and the trailing buffer zone.

28. The method of claim 27, further comprising after performing isotachophoresis:
(4) subjecting the complex to capillary zone electrophoresis or capillary gel electrophoresis in the presence of a glutamate ion.

\* \* \* \* \*